United States Patent
Nakamura

(10) Patent No.: US 7,977,491 B2
(45) Date of Patent: Jul. 12, 2011

(54) DENDRON AND DENDRIMER, METHOD OF PRODUCING THE SAME, AND METHOD OF PRODUCING A THIOACETAL COMPOUND

(75) Inventor: Koki Nakamura, Minami-ashigara (JP)

(73) Assignee: Fujifilm Corporation, Minato-Ku, Tokyo (JP)

( * ) Notice: Subject to any disclaimer, the term of this patent is extended or adjusted under 35 U.S.C. 154(b) by 1324 days.

(21) Appl. No.: 10/594,430

(22) PCT Filed: Mar. 28, 2005

(86) PCT No.: PCT/JP2005/006545
§ 371 (c)(1),
(2), (4) Date: Sep. 26, 2006

(87) PCT Pub. No.: WO2005/092847
PCT Pub. Date: Oct. 6, 2005

(65) Prior Publication Data
US 2008/0262238 A1 Oct. 23, 2008

(30) Foreign Application Priority Data

Mar. 29, 2004 (JP) ................................. 2004-095408
Mar. 29, 2004 (JP) ................................. 2004-096073
Mar. 29, 2004 (JP) ................................. 2004-096080

(51) Int. Cl.
C07D 498/00 (2006.01)
C07C 255/00 (2006.01)
C07C 321/00 (2006.01)
(52) U.S. Cl. ........................ 548/218; 560/17; 558/423
(58) Field of Classification Search .................... None
See application file for complete search history.

(56) References Cited

U.S. PATENT DOCUMENTS

| | | | |
|---|---|---|---|
| 2002/0072583 A1 | 6/2002 | Miki et al. | |
| 2003/0171507 A1 | 9/2003 | Miki et al. | |

FOREIGN PATENT DOCUMENTS

| | | | |
|---|---|---|---|
| JP | 2001-163971 A | 6/2001 | |
| JP | 2001-187751 A | 7/2001 | |
| JP | 2002-220468 A | 8/2002 | |
| JP | 2002-338535 A | 11/2002 | |
| JP | 2004-189664 A | 7/2004 | |
| JP | 2005-281172 A | 10/2005 | |
| JP | 2005-281444 A | 10/2005 | |
| WO | WO 2004/029018 A1 | 4/2004 | |
| WO | WO 2005/092847 A1 | 10/2005 | |

OTHER PUBLICATIONS

Malenfant, Chemical Materials, Dendrimer-Supported Oligothiophene Synthesis: Aliphatic Ether Dendrimers in the Preparation of Oligothiophenes with Minimal Substitution, 1999, 11 pp. 3420-3422.*
N. Gabriel Lemcoff et al., "Toward Novel Polyacetals by Transacetalation Techniques: Dendrimeric Diacetals", Organic Letter, 2002, vol. 4, No. 5, pp. 731-734, American Chemical Society.
Hideharu Mori et al., "Hyperbranched (Meth)Acrylates in Solution, Melt, and Grafted From Surfaces", Top. Curr. Chem., 2003, vol. 228, pp. 1-37.
"Science and Function of Dendrimer", edited by Kanehiko Okada, published by IPC Ltd., pp. 15-34.
Scott M. Grayson et al., "Convergent Dendrons and Dendrimers: From Synthesis to Applications", Chemical Review, 2001, vol. 101, pp. 3819-3867.
Brindaban C. Ranu et al., "Highly Efficient Transthioacetalization of O,O-Acetals Catalyzed by Indium(III) Chloride", Synlett, 2002, No. 5, pp. 727-730.
J.S. Yadav et al., "Indium(III) Chloride Catalyzed Efficient Conversion of Carbonyl Compounds to 1,3-Dithioacetals", Synthetic Communications, 2002, vol. 32, No. 5, pp. 715-719.
Ahmed Kamal et al., "Scandium Triflate as a Recyclable Catalyst for Chemoselective Thioacetalization", Tetrahedron Letters, 2002, vol. 43, pp. 1347-1350, Elsevier Science Ltd.
International Search Report dated Jul. 26, 2005.

* cited by examiner

*Primary Examiner* — Paul A Zucker
(74) *Attorney, Agent, or Firm* — Buchanan Ingersoll & Rooney PC

(57) ABSTRACT

A dendron or dendrimer, which has, as a recurring unit of each branch, a structure of formula (I):

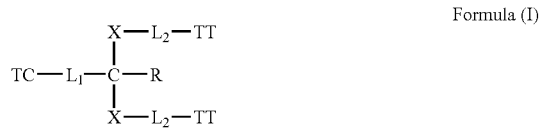

Formula (I)

wherein TC designates a linkage to a former generation in the direction to a focal point of the dendron or a core of the dendrimer; TT designates a linkage to a next generation in the direction to a terminal; X is a divalent group comprised of at least one heteroatom; $L_1$ and $L_2$ each are a divalent linking group; R is a hydrogen atom or a substituent; and a method of producing a dendron or a dendrimer; and a method of producing a thioacetal compound.

21 Claims, No Drawings

DENDRON AND DENDRIMER, METHOD OF PRODUCING THE SAME, AND METHOD OF PRODUCING A THIOACETAL COMPOUND

TECHNICAL FIELD

The present invention relates to a novel dendrimer or dendron, which can be applied, for example, to nanotechnology material, electronic material, and drug delivery system. Further, the present invention relates to a method of producing a dendrimer or dendron. Further, the present invention relates to a method of synthesizing a thioacetal, which is an important functional group in organic synthesis.

BACKGROUND ART

A dendrimer is a dendritic macromolecule whose structure is highly regulated, and it is a nano-size molecule having a substantially spherical shape and having a great number of functionalized terminals. Since the dendrimer has an isolated space of a nanometer scale, new functions or physical properties that conventional materials do not possess have been expected, and research thereon has been made in various fields, such as nanotechnology and biochemistry. In recent years, it has been reported that dendrimers or dendrons may be useful in a very wide field, including drug delivery, gene introduction, energy-trapping optically-active molecules, catalysts, molecular mass/molecular size standard materials, sensor/nano-scale science, and others. Thus, attention has been paid thereto.

In general, a compound that well-regulated branch structures extend three-dimensionally from the center, as seen in one of the schematic structure views illustrated below, is called a dendrimer; and a compound wherein the same structures extend only in one direction (that is, a sector or fan-shaped compound), as seen in the other view, is called a dendron.

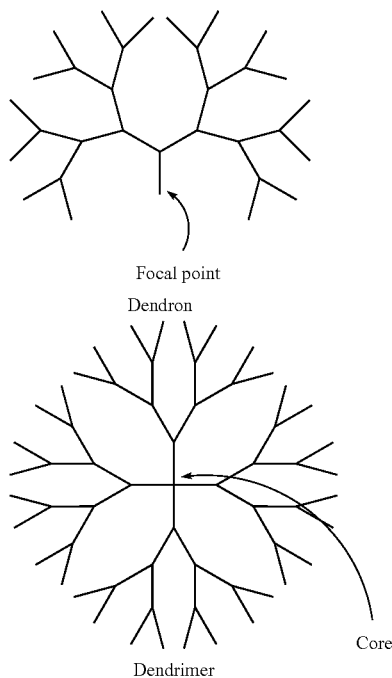

The center of a dendrimer is called a core, and that of a dendron is called a focal point. In the dendrimer, a specific chemical bond recurs between its branches. The number of the recurrences of the specific chemical bond is represented by the wording "the number of generations (or generation number)." As the generation number becomes larger, the dendrimer becomes larger, so that the shape thereof gets closer to a sphere. Recently, books on dendrimers have been published in succession (see, for example, "Topics in Current Chemistry," vol. 228, Dendrimer V, edited by C. A. Schalley and F. Vogtle, published by Springer, 2003; and "Science and Function of Dendrimer," edited by Kanehiko Okada, published by IPC Ltd.). This fact demonstrates the high interest in this field.

Nowadays, the method of synthesizing a dendrimer is being considerably established. There are many reports on a divergent method, wherein the synthesis of a dendrimer is advanced outward from a core; a convergent method, wherein the synthesis thereof is advanced inward from a terminal functional group; combination of the two methods, and the like (see, for example, JP-A-2002-338535 ("JP-A" means unexamined published Japanese patent application), Chemical Review, vol. 101, 3819-3867 (2001)). Thus, the methodology thereof is being established. However, it cannot be said that a problem peculiar when high-molecular-mass compounds are handled; that is, a problem that the purification of a dendrimer is very difficult, has been sufficiently solved already.

In the divergent method, there is adopted a method of forming a branch structure onto the surface of a dendrimer (or dendron) containing a core, thereby making the number of generations of the dendrimer (or dendron) large. However, when a portion where the branch structure is not completely formed remains, it is very difficult to remove this byproduct. This difficulty increasingly becomes larger as the number of generations becomes larger.

It is said that the convergent method may become a method that avoids the difficulty of purification, which is a drawback of the divergent method. Specifically, there is adopted a method of bonding, to a focal point, plural (usually two or three) dendron molecules, whose generation number is lower by one (hereinafter referred to as the starting dendron molecules), so as to form a branch structure; therefore, the molecule species that need to be removed at the time of purification in the convergent method are the focal point moiety, the starting dendron molecules, and incomplete dendron molecules wherein a branch structure is not completely formed (hereinafter referred to as incomplete dendron molecules). According to conventional methods, incomplete dendron molecules are not easily removed; therefore, in many cases, an excess amount of the starting dendron molecules is used for the focal point moiety, thereby decreasing the incomplete dendron molecules.

However, this method has the following drawbacks: As the number of the generation becomes higher, more steps are necessary, so that the starting dendron molecules, which are valuable, are used in a more excessive amount (in vain); and further, it also becomes more difficult to remove the excessive amount of the starting dendron molecules for purification, as the number of the generation becomes higher. For this reason, there has been a strong need for development of a method that enables synthesizing a dendron effectively and purifying the dendron easily.

A thioacetal structure is generally very stable against strong acidity and strong basicity, and it can be used for being converted to a carbonyl group or as an acyl anion equivalent, or alternately, it can be reduced to methylene also. Accordingly, a thioacetal structure is used for the synthesis of various compounds. Thus, this structure is very important for organic synthesis.

As described above, usefulness of thioacetal has been recognized in a wide field for a long time. However, as to the method of the synthesis thereof, many points to be improved remain from the viewpoint of rapid, highly-effective, and widely-usable reaction. In recent years, many synthesis methods thereof have been reported (see, for example, Synlett, No. 5, pp. 727-730 (2002); Synthetic Communications, vol. 32, No. 5, pp. 715-719; and Tetrahydron Letters, vol. 43, pp. 1347-1350).

Other and further features and advantages of the invention will appear more fully from the following description.

DISCLOSURE OF INVENTION

The present invention resides in a dendron, which has, as a recurring unit of each branch, a structure represented by formula (I):

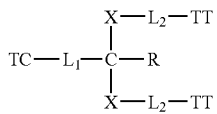

Formula (I)

wherein TC designates a linkage to a former (or previous) generation in the direction to a focal point of the dendron; TT's each designate a linkage to a next generation in the direction to a terminal of the dendron; X represents a divalent group comprised of at least one heteroatom; $L_1$ and $L_2$'s each independently represent a divalent linking group; R represents a hydrogen atom or a substituent; and in the recurring units, X's may be the same or different, R's may be the same or different, $L_1$'s may be the same or different, and $L_2$'s may be the same or different.

Further, the present invention resides in a dendrimer, which has, as a recurring unit of each branch, a structure represented by formula (I):

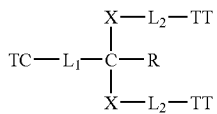

Formula (I)

wherein TC designates a linkage to a former generation in the direction to a core of the dendrimer; TT's each designate a linkage to a next generation in the direction to a terminal of the dendrimer; X represents a divalent group comprised of at least one heteroatom; $L_1$ and $L_2$'s each independently represent a divalent linking group; R represents a hydrogen atom or a substituent; and in the recurring units, X's may be the same or different, R's may be the same or different, $L_1$'s may be the same or different, and $L_2$'s may be the same or different.

Further, the present invention resides in a method of producing a dendron, which is a convergent method in which n branches, i.e. the number of branches is n, are formed from a gth generation, so as to form a (g+1)th generation, in which n is an integer of 2 to 5 and g is an integer of 1 or more, and which method comprises the step of:
carrying out a reaction, to form the branches, the reaction satisfying a relationship of:

$k_1 < k_m$ wherein m is an integer of 2 or more but less than n; $k_1$ represents a rate of growth reaction from the gth generation to the (g+1)th generation, in which only one branch has grown from the gth generation; and $k_m$ represents a rate of reaction from a structure in which (m−1) branches out of the n branches have grown to a structure in which m branches have grown.

Further, the present invention resides in a method of producing a dendron or a dendrimer, which method comprises:
subjecting a thiol to a reaction with a carbonyl compound or an equivalent thereof, to form a thioacetal, thereby forming a branch structure of said dendron or said dendrimer.

Further, the present invention resides in a method of producing a thioacetal compound, which method comprises:
subjecting a thiol compound having in the molecule thereof a thioacetal structure, to a reaction with a carbonyl compound or an equivalent thereof in the presence of a catalyst, in a reaction solvent selected from ethers, esters, amides, sulfoxides, alcohols, nitriles, and sulfones, thereby to form a thioacetal structure.

BEST MODE FOR CARRYING OUT INVENTION

According to the present invention, there are provided the following means:

(1) A dendron, having, as a recurring unit of each branch, a structure represented by formula (I):

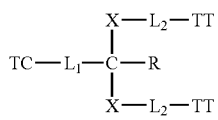

Formula (I)

wherein TC designates a linkage to a former generation in the direction to a focal point of the dendron; TT's each designate a linkage to a next generation in the direction to a terminal of the dendron; X represents a divalent group comprised of at least one heteroatom; $L_1$ and $L_2$'s each independently represent a divalent linking group; R represents a hydrogen atom or a substituent; and in the recurring units, X's may be the same or different, R's may be the same or different, $L_1$'s may be the same or different, and $L_2$'s may be the same or different.

(2) The dendron according to the above item (1), wherein the divalent group represented by X in the formula (I) is —S—, —SO—, or —SO$_2$—.

(3) The dendron according to the above item (1), wherein the divalent group represented by X in the formula (I) is —S—.

(4) A dendrimer, having, as a recurring unit of each branch, a structure represented by formula (I):

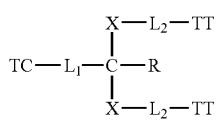

Formula (I)

wherein TC designates a linkage to a former generation in the direction to a core of the dendrimer; TT's each designate a linkage to a next generation in the direction to a terminal of the dendrimer; X represents a divalent group comprised of at least one heteroatom; $L_1$ and $L_2$'s each independently represent a divalent linking group; R represents a hydrogen atom or a substituent; and in the recurring units, X's may be the same or different, R's may be the same or different, $L_1$'s may be the same or different, and $L_2$'s may be the same or different.

(5) The dendrimer according to the above item (4), wherein the divalent group represented by X in the formula (I) is —S—, —SO—, or —$SO_2$—.

(6) The dendrimer according to the above item (4), wherein the divalent group represented by X in the formula (I) is —S—.

(Hereinafter, a first embodiment of the present invention means to include the dendrons or dendrimers described in the items (1) to (6) above.)

(7) A method of producing a dendron, which is a convergent method in which n branches are formed from a gth generation, so as to form a (g+1)th generation, in which n is an integer of 2 to 5 and g is an integer of 1 or more, which comprises the step of:
carrying out a reaction, to form the branches,
the reaction satisfying a relationship of:

$$k_1 < k_m$$

wherein m is an integer of 2 or more but less than n; $k_1$ represents a rate of growth reaction from the gth generation to the (g+1)th generation, in which only one branch has grown from the gth generation; and $k_m$ represents a rate of reaction from a structure in which (m−1) branches out of the n branches have grown to a structure in which m branches have grown.

(8) The method of producing a dendron according to the above item (7), wherein the reaction rate $k_m$ further satisfy a relationship of:

$$k_{m-1} < k_m < k_n$$

wherein $k_{m-1}$ represents a rate of reaction from a structure in which (m−2) branches out of the n branches have grown to a structure in which (m−1) branches have grown, and $k_n$ represents a rate of reaction from a structure in which (n−1) branches out of the n branches have grown to a structure in which n branches have grown.

(9) The method of producing a dendron according to the above item (7) or (8), wherein the step of forming branches is carried out repeatedly.

(10) A method of producing a dendron or a dendrimer, comprising:
subjecting a thiol to a reaction with a carbonyl compound or an equivalent thereof, to form a thioacetal, thereby forming a branch structure of said dendron or said dendrimer.

(Hereinafter, a second embodiment of the present invention means to include the methods described in the items (7) to (10) above)

(11) A method of producing a thioacetal compound, comprising:
subjecting a thiol compound having in the molecule thereof a thioacetal structure, to a reaction with a carbonyl compound or an equivalent thereof, in the presence of a catalyst, in a reaction solvent selected from ethers, esters, amides, sulfoxides, alcohols, nitriles, and sulfones, thereby to form a thioacetal structure.

(12) The method of producing a thioacetal compound according to the above item (11), wherein the solvent is a cyclic ether.

(13) A method of producing a dendrimer, comprising the step of:
producing a thioacetal structure by the method of producing a thioacetal compound according to the above item (11) or (12).

(14) A method of producing a dendron, comprising the step of:
producing a thioacetal structure by the method of producing a thioacetal compound according to the above item (11) or (12).

(Hereinafter, a third embodiment of the present invention means to include the methods described in the items (11) to (14) above)

Herein, the present invention means to include all of the above first, second, and third embodiments, unless otherwise specified.

The present invention is described in detail below.

First, the first embodiment of the present invention is described below.

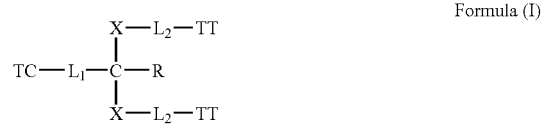

Formula (I)

The compound of the present invention, represented by formula (I), i.e. the compound having the structure of formula (I) as a recurring unit of a certain generation, has a structural feature that the compound has a structure in which two or more heteroatom substituents (—X-$L_2$-TT) are bonded to a geminal carbon (represented by the "C" in formula (I)), a typical example of the structure being acetal. In the present invention, the heteroatom substituents may be the same or different from each other, and they are preferably the same. The present invention is based on a finding that these structures have a great advantage for constructing a branch structure characteristic for a dendrimer or a dendron. As known for a long time, in general, an acetal structure can easily be synthesized by subjecting a carbonyl compound, such as a ketone or an aldehyde, with an alcohol or a thiol, to dehydration reaction. It is known that the synthesis of a large amount thereof is also very easy.

A compound of the present invention wherein X in formula (I) is, for example, an oxygen atom, can be produced by using, as a carbonyl compound equivalent, a compound having two leaving groups on its geminal carbon, and subjecting, to nucleophilic substitution reaction, this compound and a compound having an alcoholic hydroxyl group as a group which contains an oxygen atom (preferably, an alcohol or a phenol or a derivative thereof, more preferably a phenol or a derivative thereof).

In the present invention, TC in formula (I) designates a linkage to a former generation at the focal point side of the dendron, in the case of dendron; and it designates a linkage to a former generation at the core side of the dendrimer, in the case of dendrimer. TT designates a linkage to a next generation at the terminal side of the dendron or dendrimer. In other words, in a dendron, TC means that the moiety in interest is linked, at "TC," to a moiety, which is a recurring unit of the former generation, adjacent thereto in the direction toward a focal point of the dendron, and TT means that said moiety is linked, at "TT," to a moiety, which is a recurring unit of the next generation, adjacent thereto in the direction toward a terminal of the dendron; and, in a dendrimer, TC means that the moiety in interest is linked, at "TC," to a moiety, which is a recurring unit of the former generation, adjacent thereto in the direction toward a core of the dendrimer, TT means that said moiety is linked, at "TT," to a moiety, which is a recurring unit of the next generation, adjacent thereto in the direction toward a terminal of the dendrimer. From the viewpoint of synthesis, the number of generations of the dendron or dendrimer is increased from the TC side to the TT side according to the divergent method, and the number of generations is increased from the TT side to the TC side according to the convergent method. In order to obtain the compound of the present invention, it is most effective to use acetalization reaction, in the reaction to increase the generation number.

X represents a divalent group comprised of at least one heteroatom. Examples of the heteroatom include an oxygen atom, a sulfur atom, a selenium atom, and a tellurium atom. X is preferably a divalent group containing a sulfur atom(s), from the viewpoint of the stability of the molecule, and it is particularly preferably a divalent group selected from —S—, —SO— and —SO$_2$—.

$L_1$ and $L_2$'s, which may be the same or different, each represent a mere single bond or a divalent linking group. $L_1$ and $L_2$'s each may be any divalent linking group. Preferable examples thereof include an alkylene group, an alkenylene group, an alkynylene group, a cycloalkylene group, an arylene group, a heteroarylene group, —O—, —S—, —P=O($R_1$)—, —N(R)—, —CO—, —SO—, —SO$_2$—, —Si($R_1$)($R_2$)—, and combination thereof, each of which may have a substituent, in which $R_1$ and $R_2$ each independently represent a hydrogen atom or a substituent. Preferable examples of the substituent include an alkyl group, an aryl group, a heteroaryl group, and an alkoxy group, each of which may be substituted.

Specific and preferable examples of the linking groups $L_1$ and $L_2$ include —CH$_2$—, —CH$_2$CH$_2$—, —CH$_2$CH$_2$CH$_2$—, 1,2-phenylene, 1,3-phenylene, 1,4-phenylene, α,2-tolylene, α,3-tolylene, α,4-tolylene, o-xylylene, m-xylylene, p-xylylene, and a divalent group wherein any one of these divalent groups is combined with —O—, —S—, —P=O($R_1$)—, —N($R_1$)—, —CO—, —SO—, —SO$_2$— or —Si($R_1$)($R_2$)—.

R represents a hydrogen atom or a substituent. Examples of the substituent include an alkyl group, an aryl group, a heteroaryl group, and —X-$L_2$-TT, each of which may have a substituent. In the case that R is a group other than a hydrogen atom or —X-$L_2$-TT, that is, R is an alkyl, aryl or heteroaryl group or some other group, the chemical formula mass thereof is preferably from 1 to 500, more preferably from 1 to 200, most preferably from 1 to 120. Specific examples of this substituent R include a methyl group, an ethyl group, a n-propyl group, an isopropyl group, a phenyl group, a 4-methoxyphenyl group, a cyclopropyl group, and a 4-pyridyl group.

In the dendron or dendrimer of the present invention, the generation number is 2 or more, preferably from 2 to 500, more preferably from 2 to 100, and most preferably from 2 to 20.

In the compound of the present invention, represented by formula (I), when X is S, the compound may be oxidized with an oxidizing agent, such as a peroxide, hydrogen peroxide, potassium permanganate, or an N-oxide, thereby a dendron or dendrimer converted to a sulfoxide or sulfone can easily be synthesized. The resultant compound is as useful as the compound represented by formula (I).

The dendrimer and dendron of the present invention having, as their branch structure, a thioacetal structure, as well as any sulfoxide compound or sulfone compound, each of which may be obtained by oxidizing the moiety of X in the dendrimer or dendron into a —SO— or —SO$_2$— group, are novel compounds, which have not been known hitherto.

The dendron or dendrimer of the present invention can be applied to compounds having various focal points or cores. From the viewpoint of the synthesis thereof also, the present invention has high usability in wide ranges. In other words, the synthesis of a dendron of each generation is performed via a stage when a compound having, as its focal point, a mercapto group high in reactivity is present as a synthesis intermediate of the dendron; therefore, the intermediate can be bonded to a wide variety of substances, using this mercapto group. For example, the following methods can be used: A method of subjecting the intermediate to condensation-reaction with a carbonyl compound, such as an aldehyde or ketone, or an equivalent thereof, to form a thioacetal; a method of subjecting the intermediate to nucleophilic substitution reaction with a compound active to nucleophilic substitution reaction, such as a halide or sulfonate, to form a thioether; a method of subjecting the intermediate to reaction (e.g. addition reaction or addition/elimination reaction) with a conjugated addition-acceptable compound, such as an α,β-unsaturated ester, to form a thioether; a method of subjecting the intermediate to reaction with a metal capable of being bonded to a thiol, such as gold or silver, so as to bond the intermediate to the surface of the metal; or a method of subjecting the intermediate to reaction with a metal salt, such as a silver halide, to cause the intermediate to be chemically adsorbed on a surface; or a method to form a salt of a metal ion.

The above-mentioned focal point or core is described in detail hereinafter. The focal point or core as shown schematically above, means the TC (moiety) bonded to the branch structure farthest from a terminal among the recurring units represented by formula (I) according to the present invention. The focal point of the dendron is a monovalent group; and the core of the dendrimer is a divalent group or a higher-valent group, preferably 2 valent (i.e. divalent) to 50 valent, more preferably 2 to 20 valent, and most preferably 2 to 16 valent. The focal point or core each may have a substituent, and it is preferably a chain or cyclic saturated hydrocarbon, a chain or cyclic unsaturated hydrocarbon, an aromatic hydrocarbon, a non-aromatic heteroring, an aromatic heteroring, or the like. Examples of the substituent include a mercapto group, a hydroxyl group; a cyano group, a nitro group, a halogen atom (e.g. fluorine, chlorine, bromine, or iodine), a hydrazino group, an azo group, an isocyanato group, an isothiocyanato group, a thiocyanato group, a carboxyl group, a sulfo group, an acyl group, a formyl group, an alkoxycarbonyl group, a carbamoyl group, a sulfamoyl group, an alkoxysulfonyl group, a sulfonyl group, an amino group, an acylamino group, a sulfonylamino group, a sulfenyl group, a sulfinyl group, an alkoxy group, an alkyl group, an alkenyl group, an alkynyl group, an aryl group, a silyl group, a silyloxy group, and a heterocyclic group.

Specific examples of the compound of the present invention are shown below, but the scope of the invention is not limited to the specific examples.

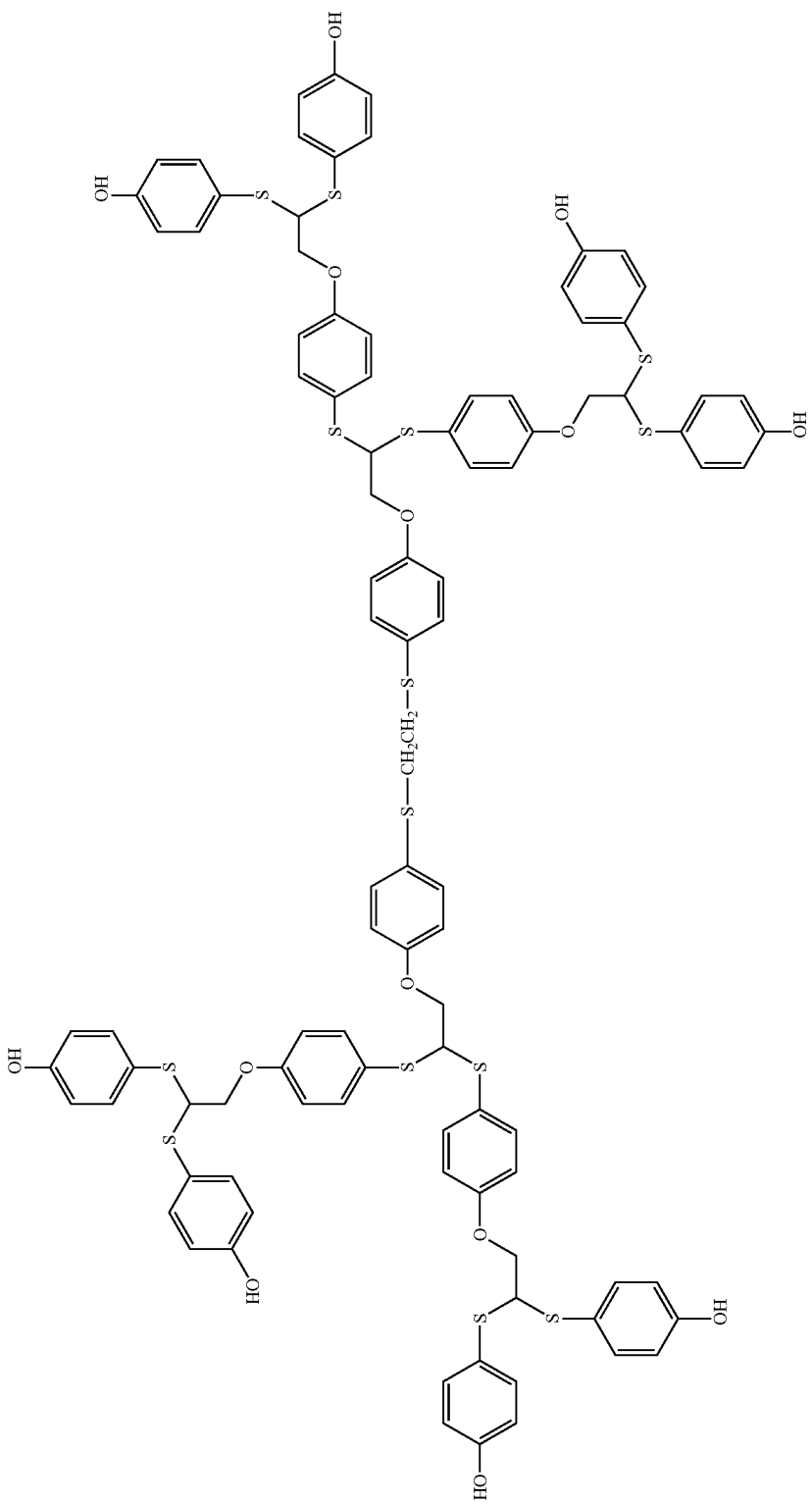
(1)

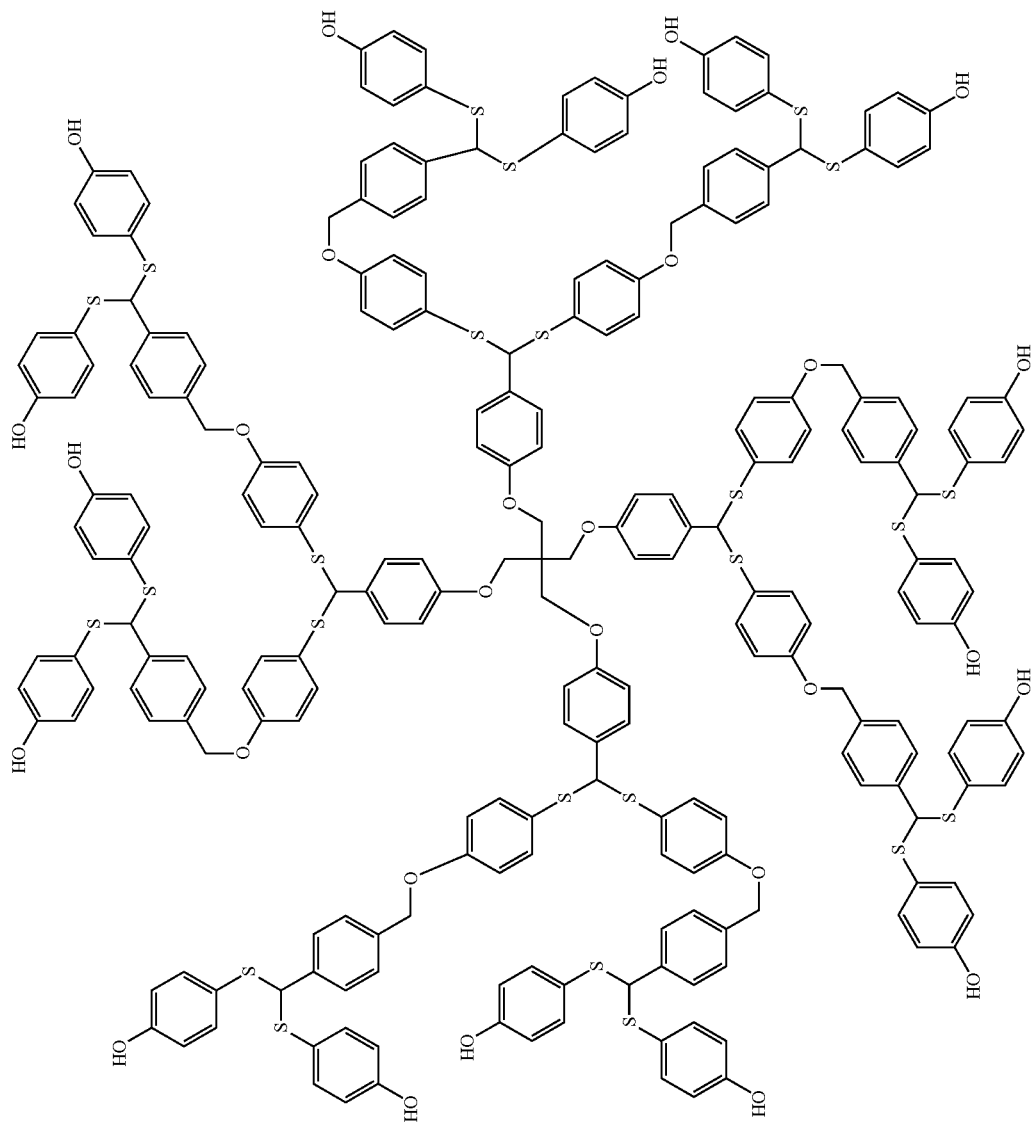
(2)

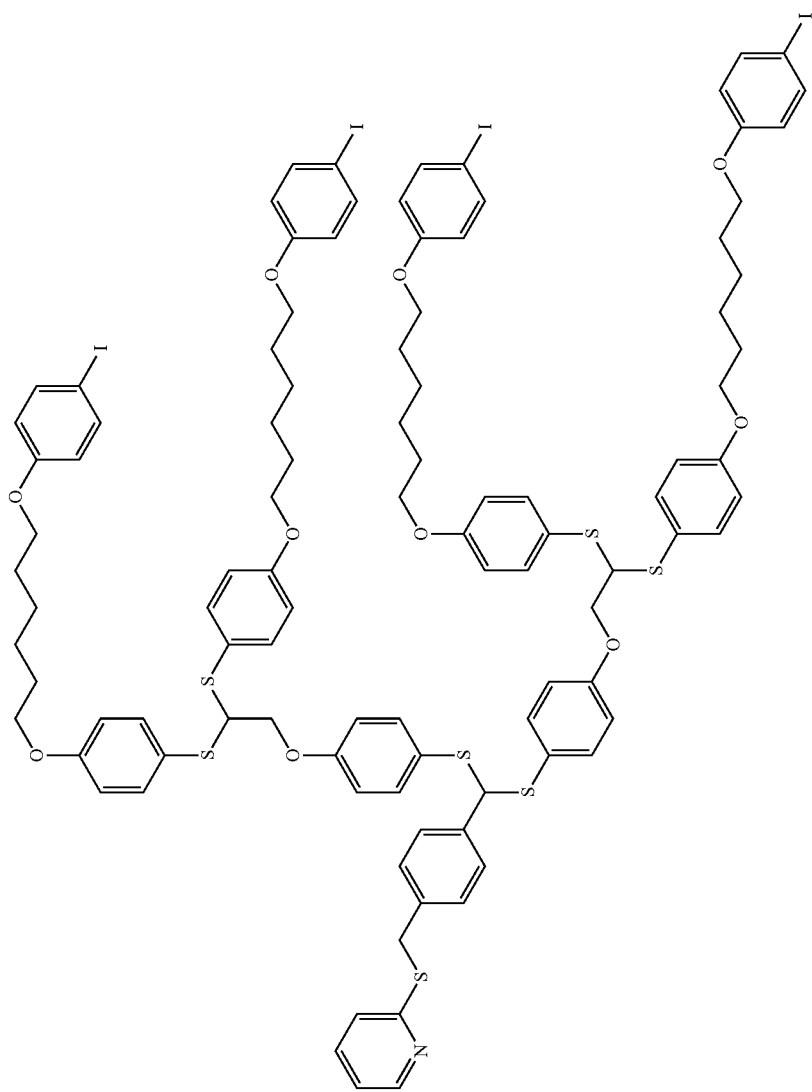
(3)

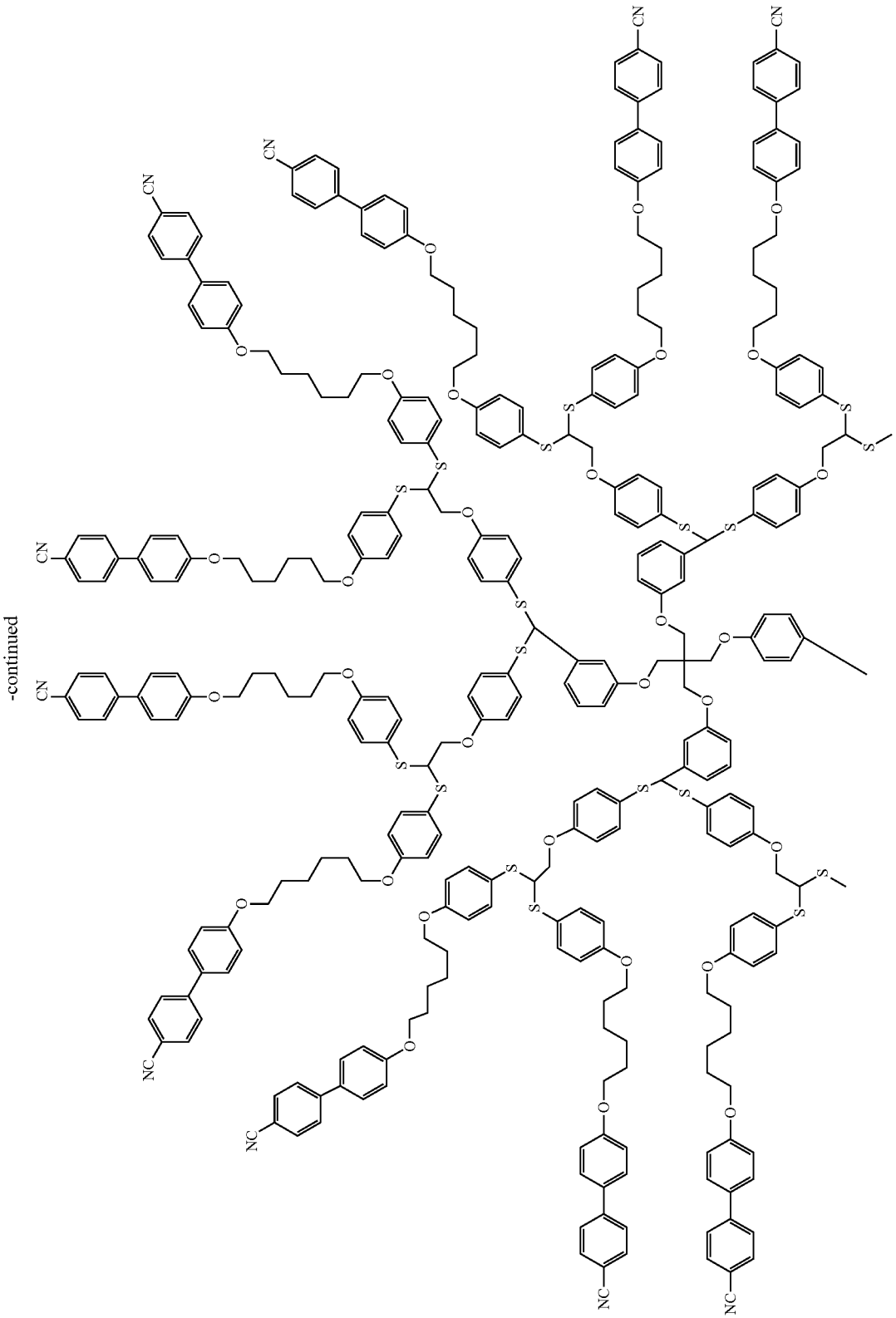
(4)

-continued
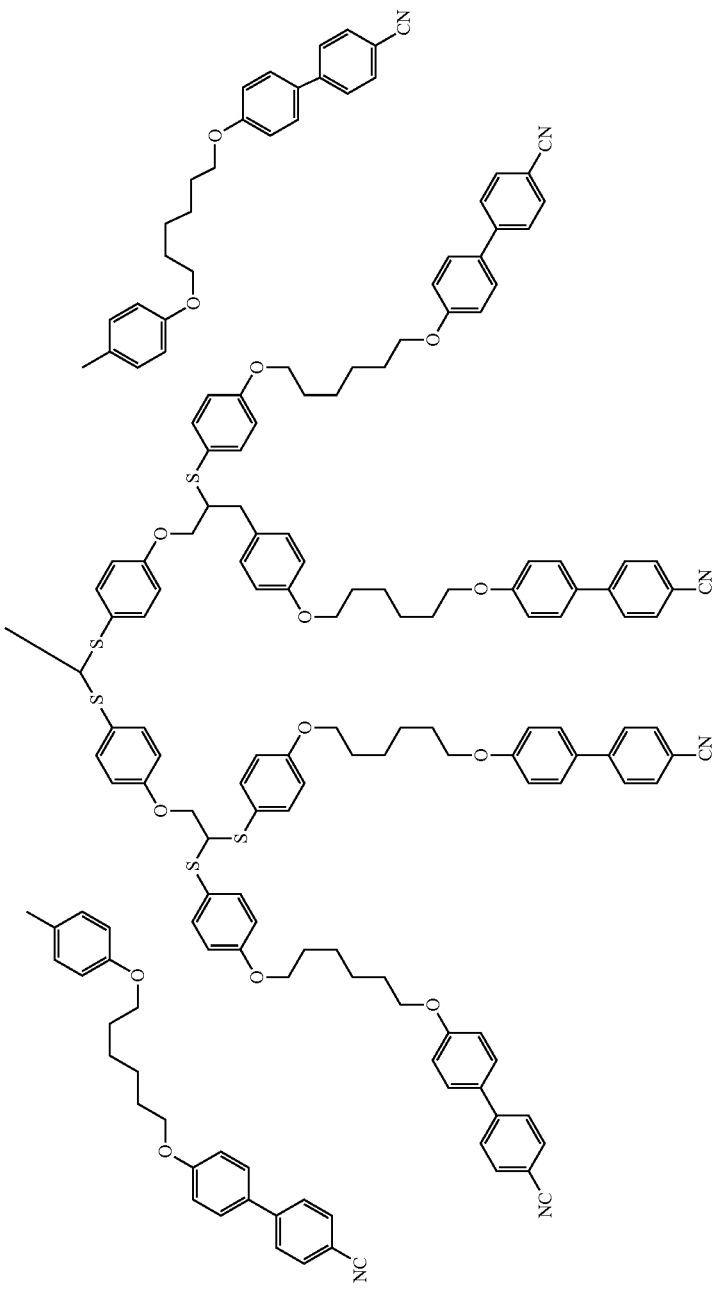

-continued
(5)
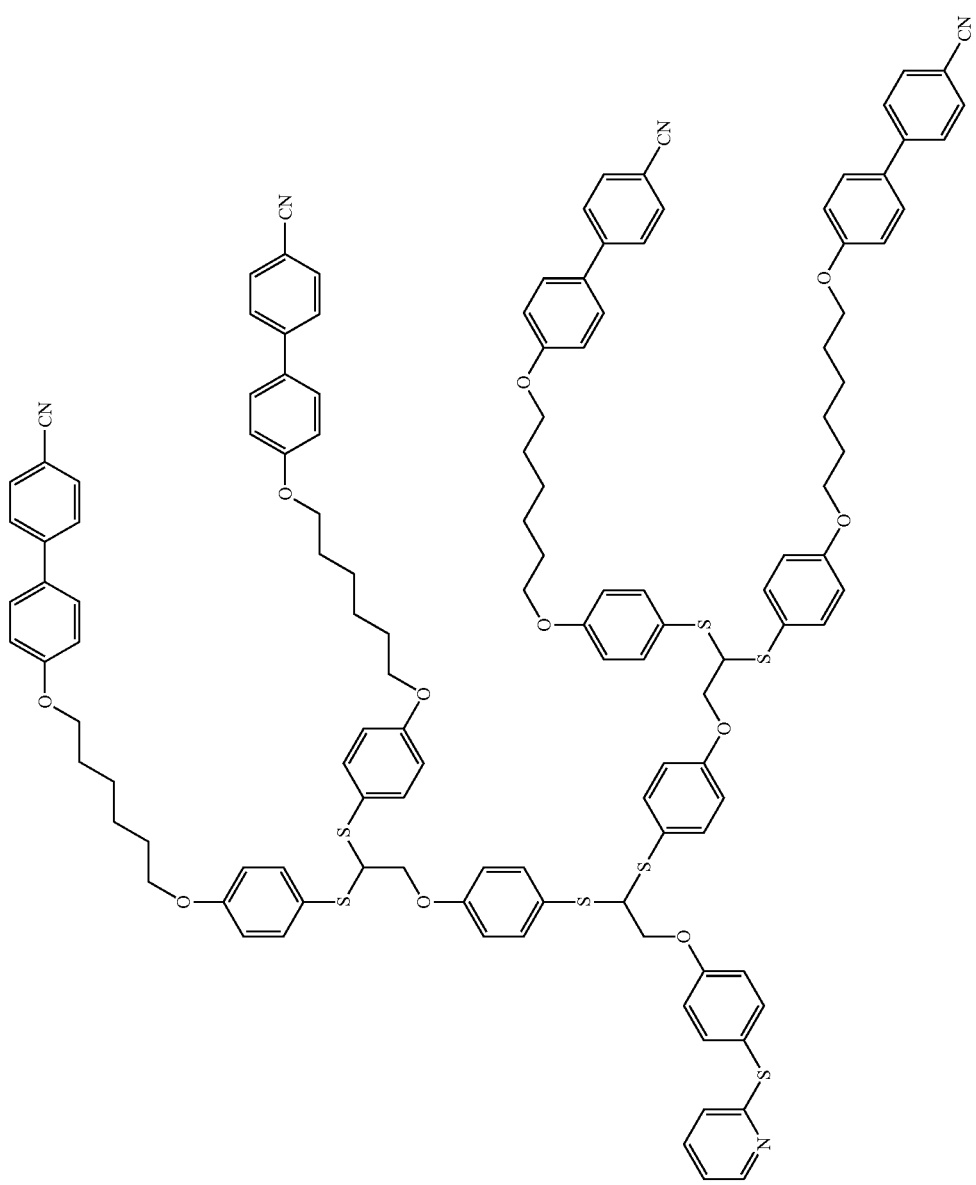

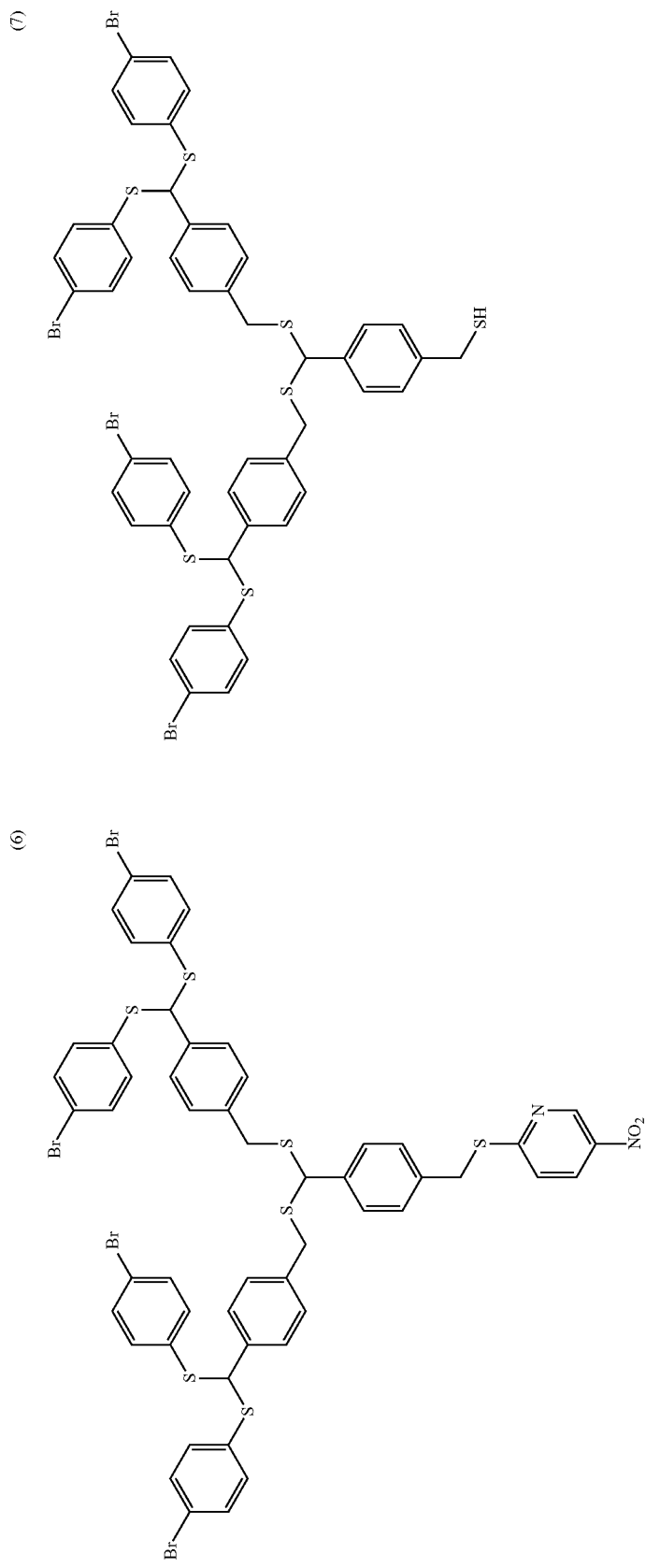

-continued
(8)
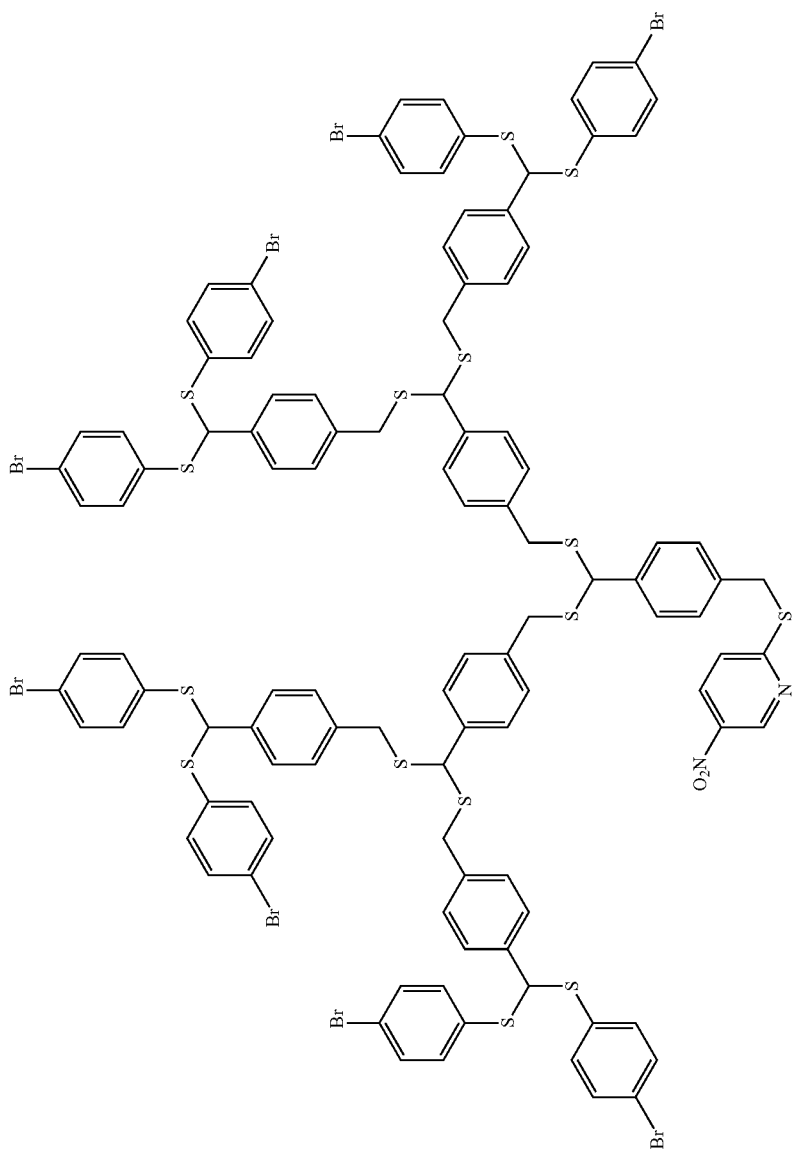

(9)
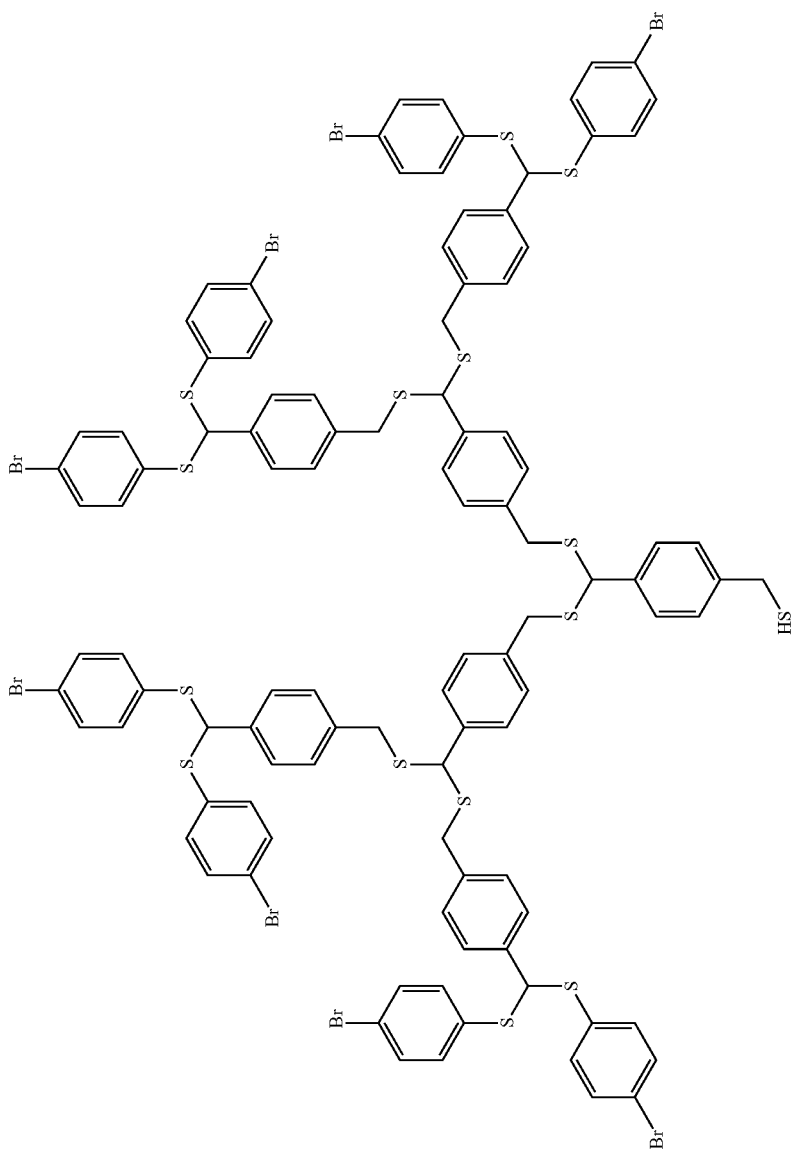

-continued
(10)
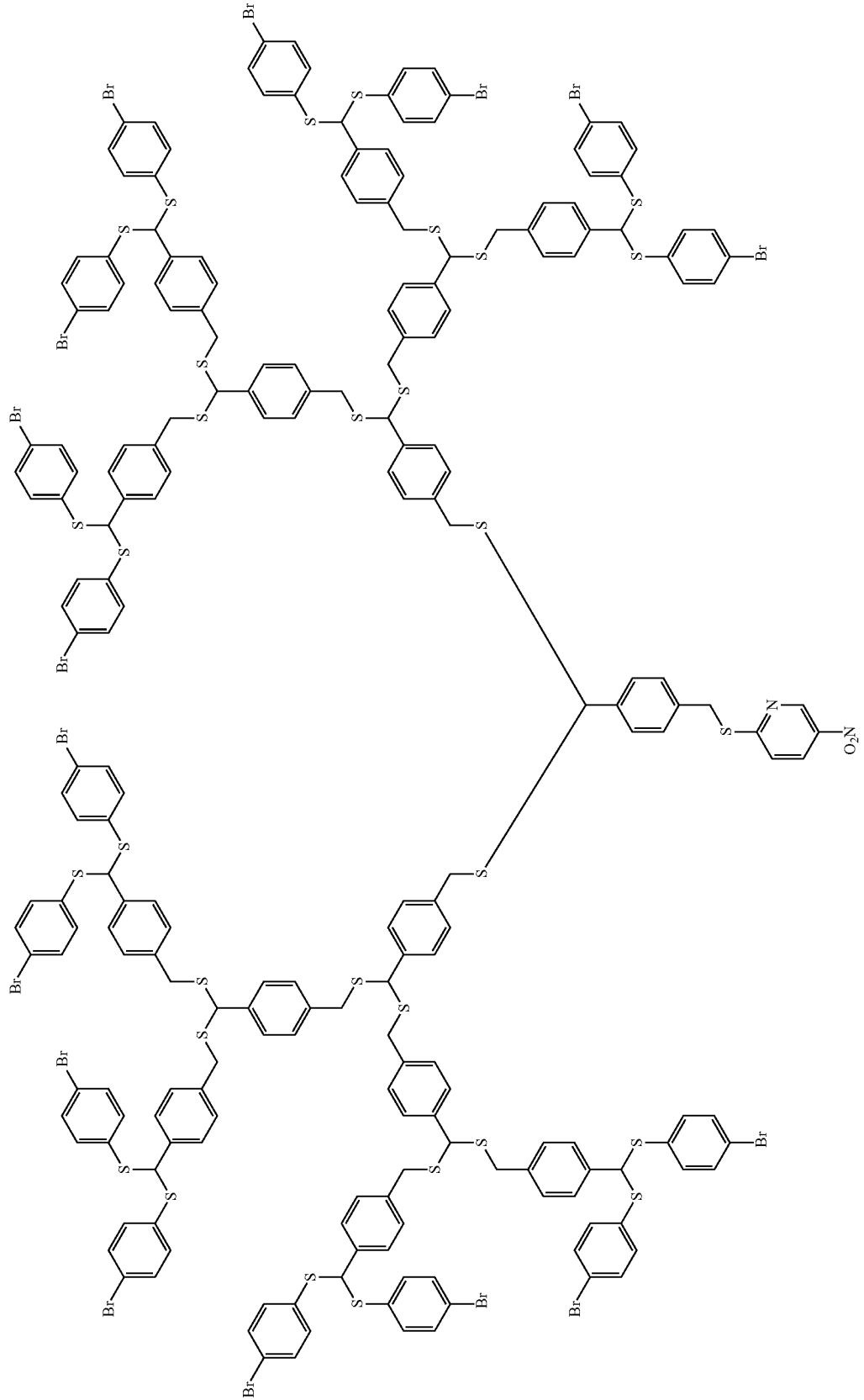

-continued
(11)
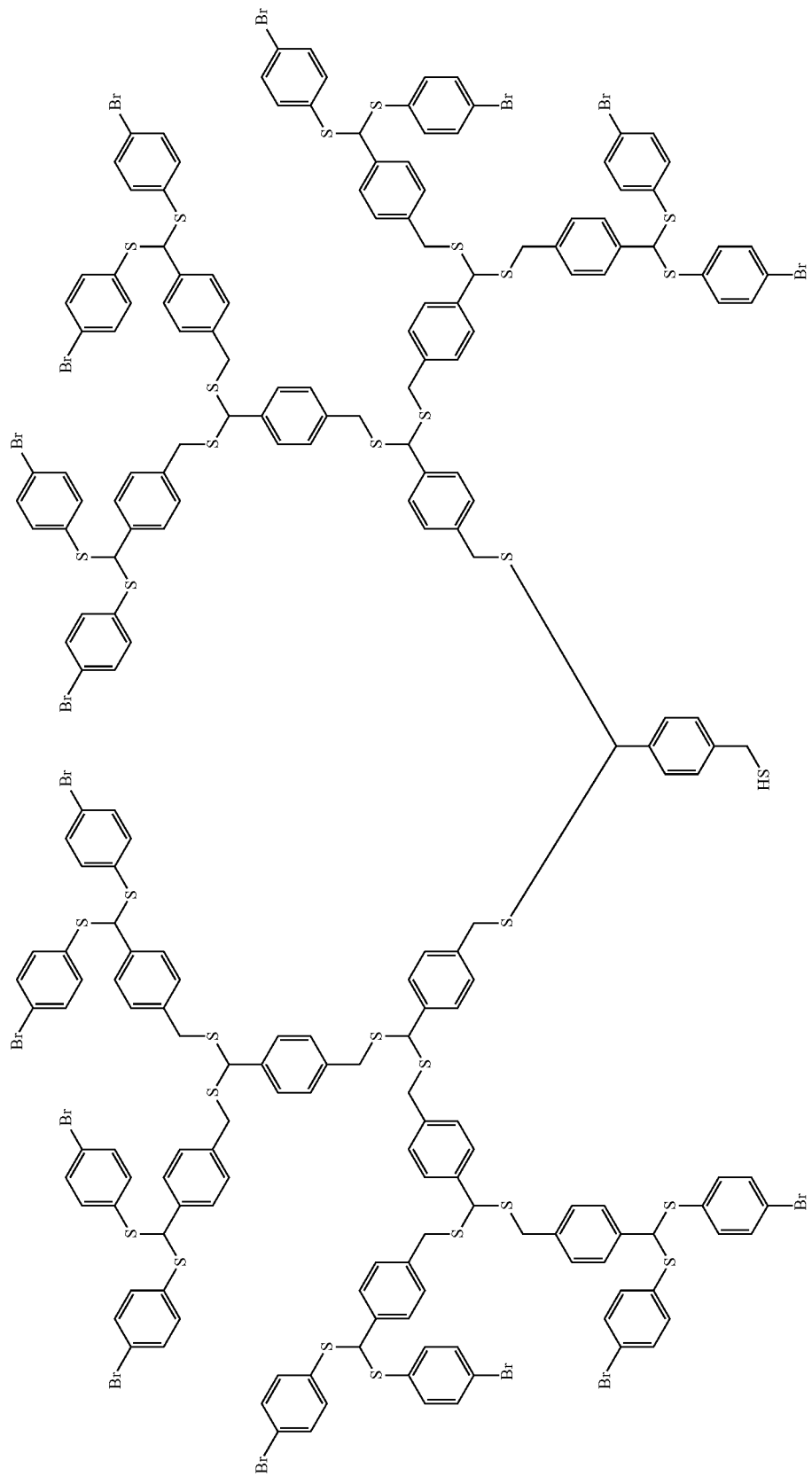

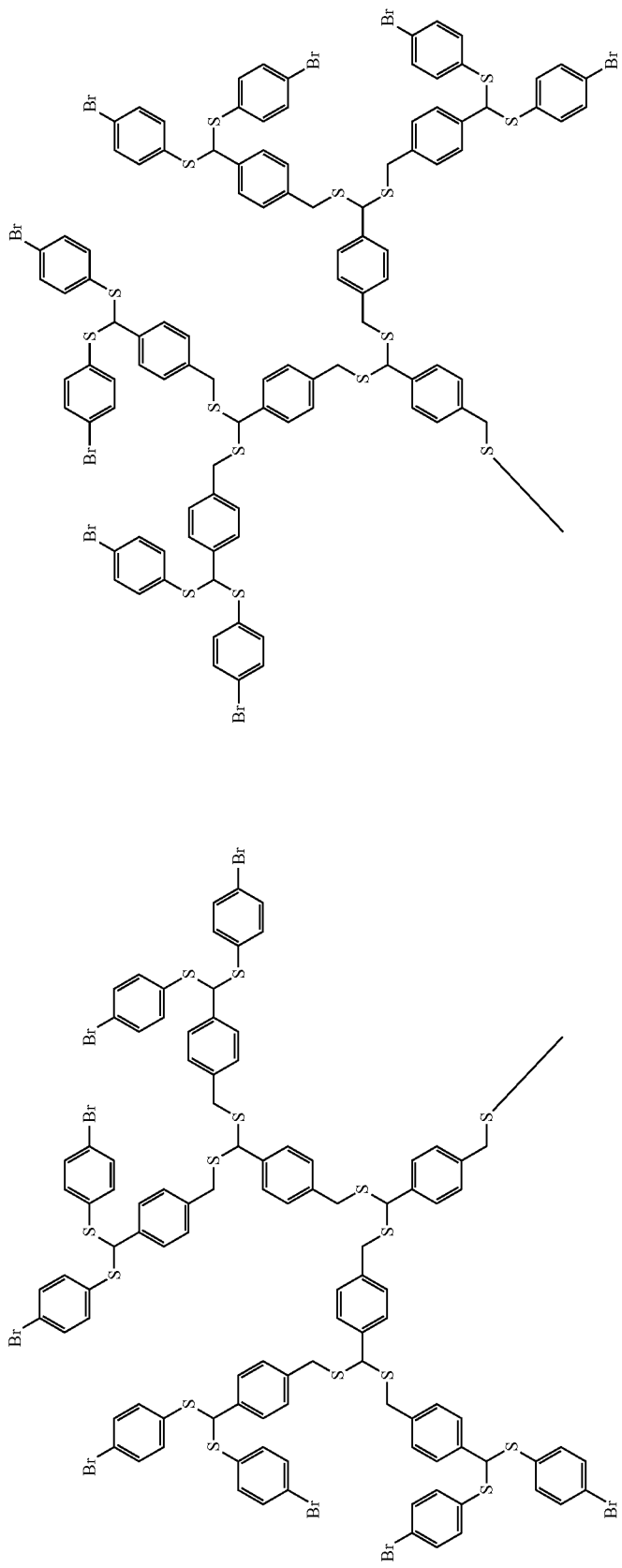

-continued
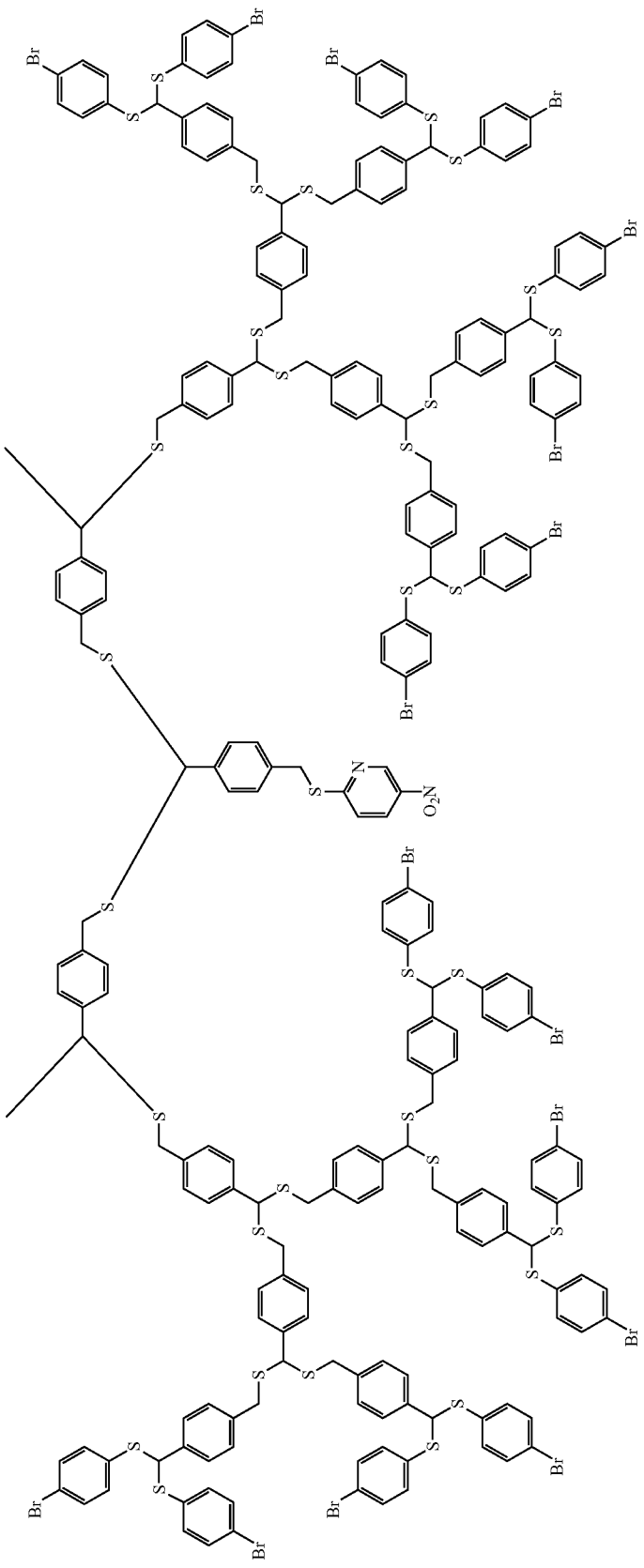

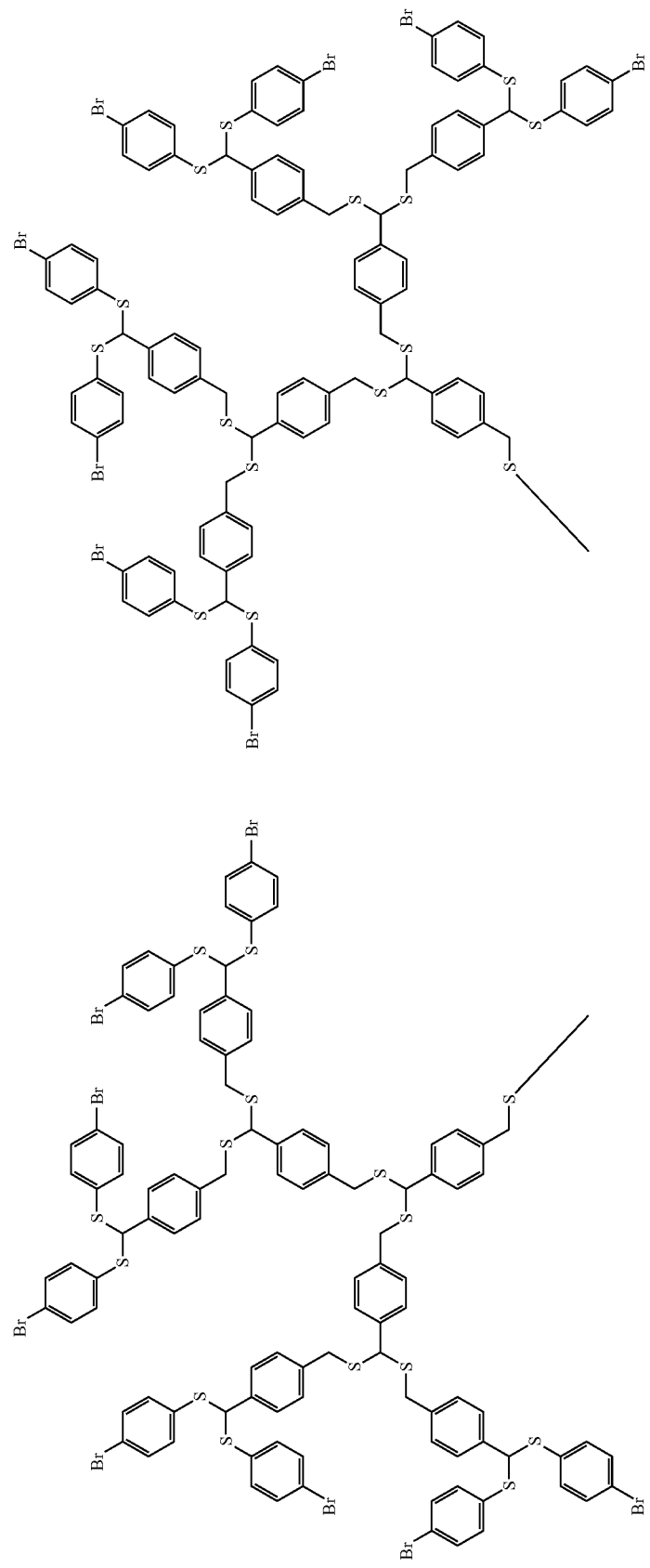
(13)

-continued
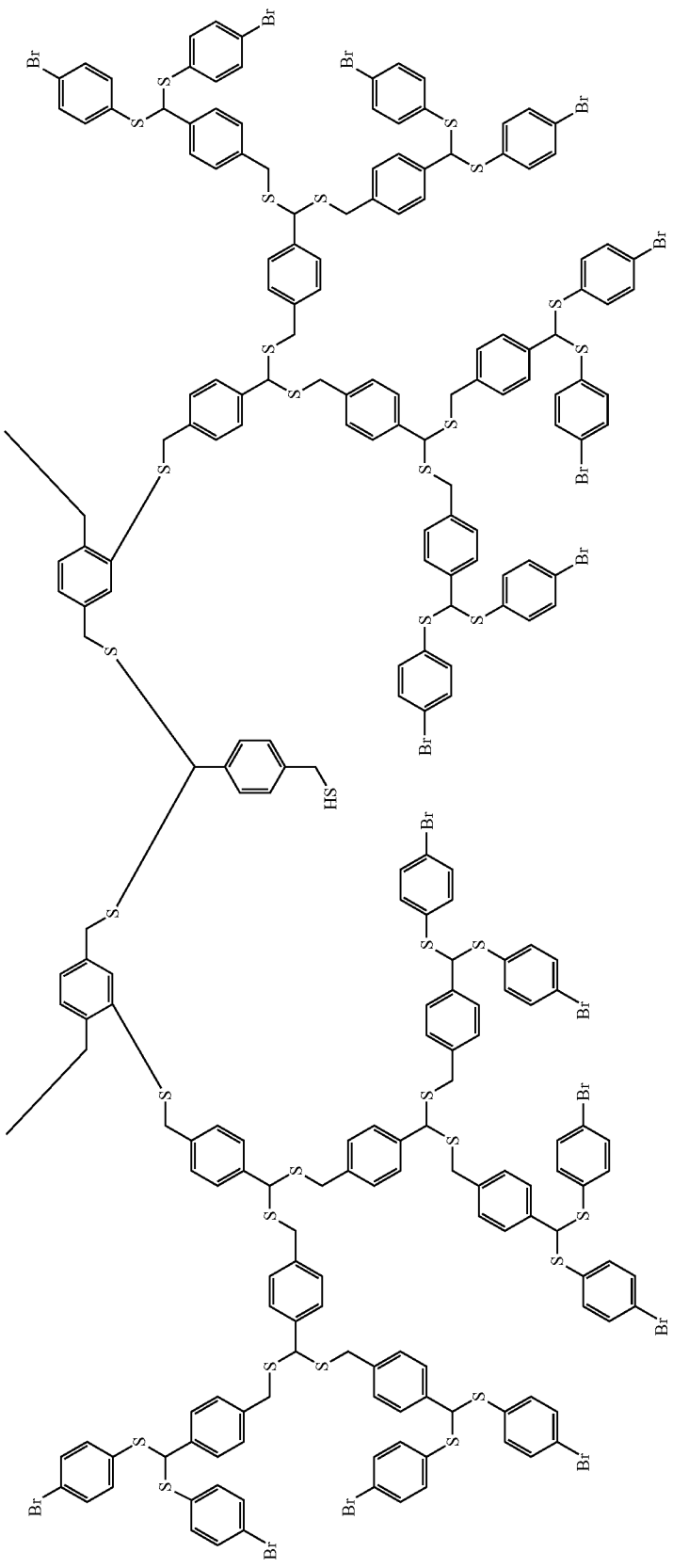

(14)
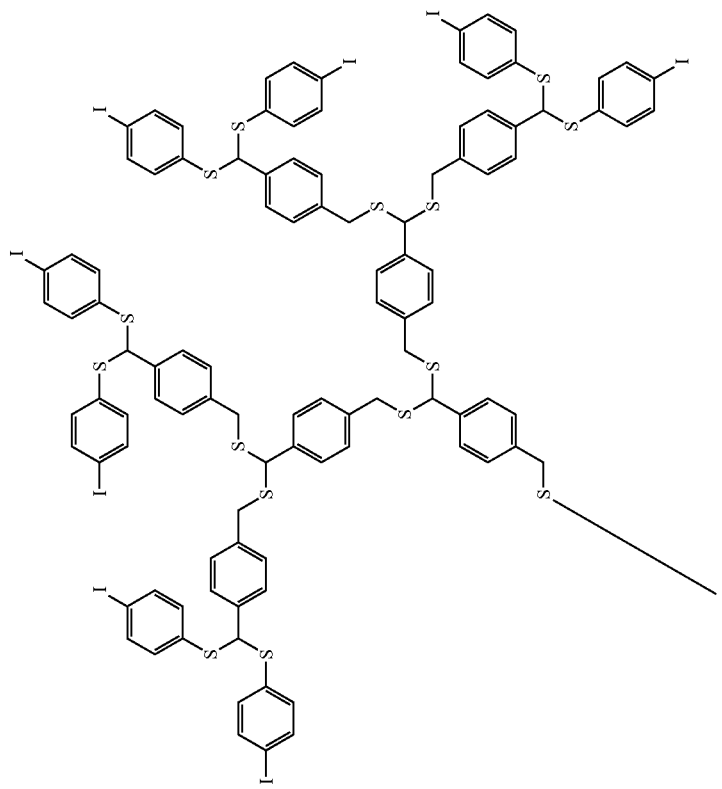
-continued
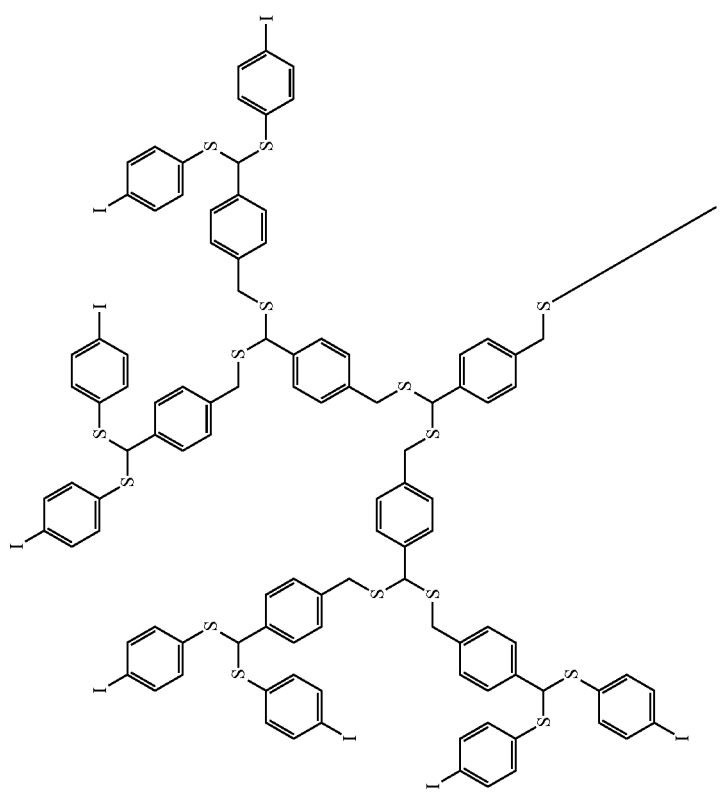

-continued
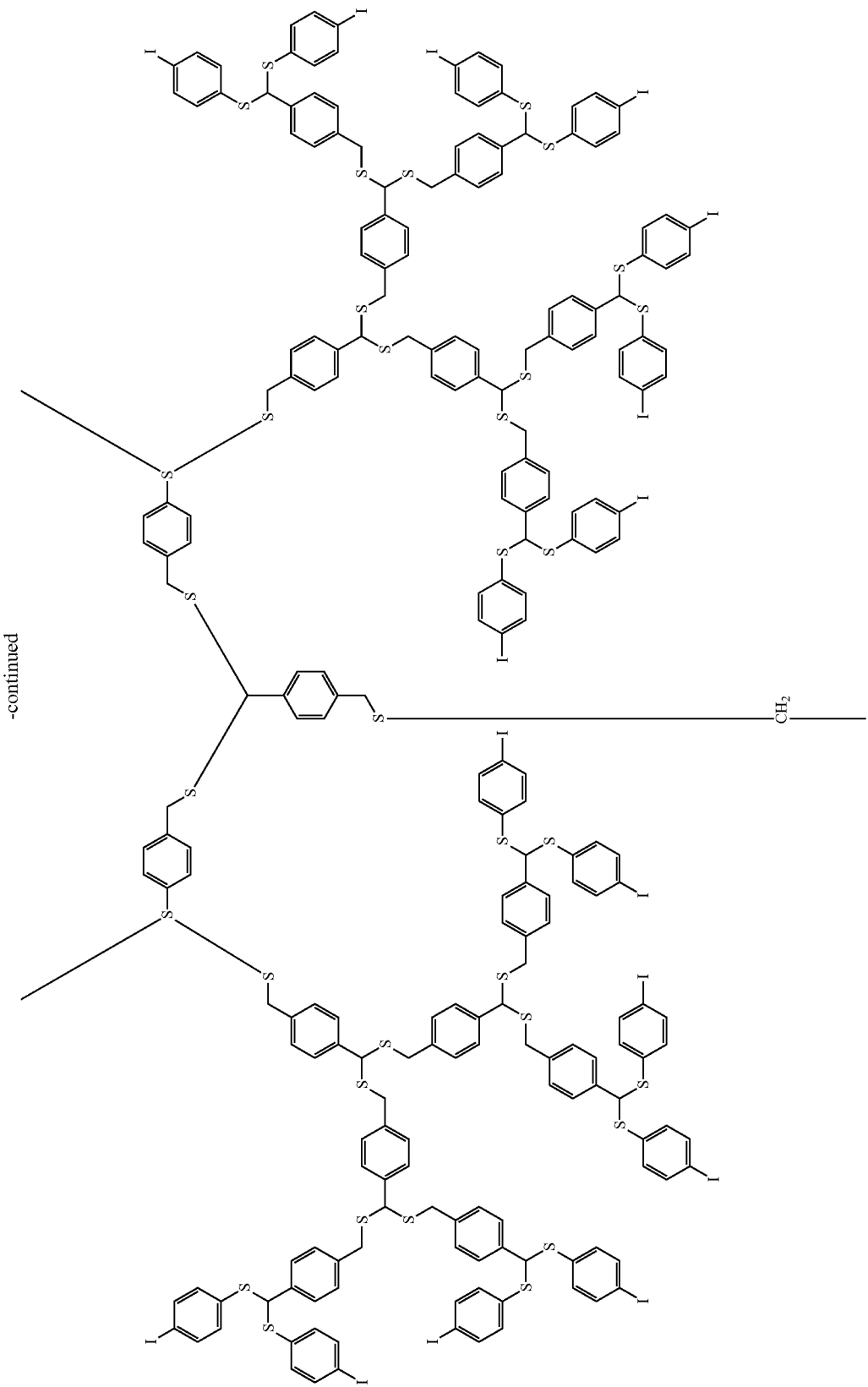

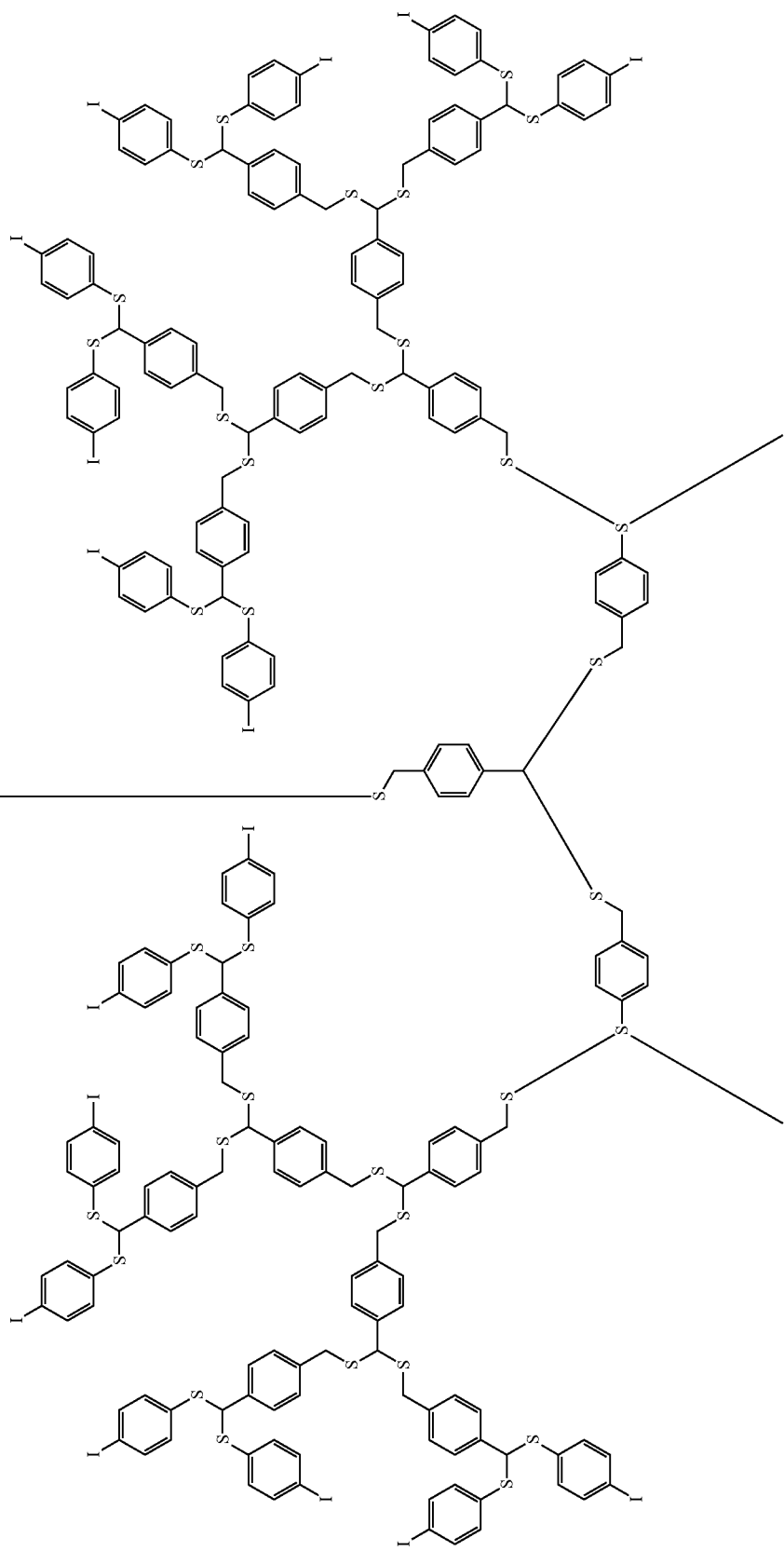
-continued

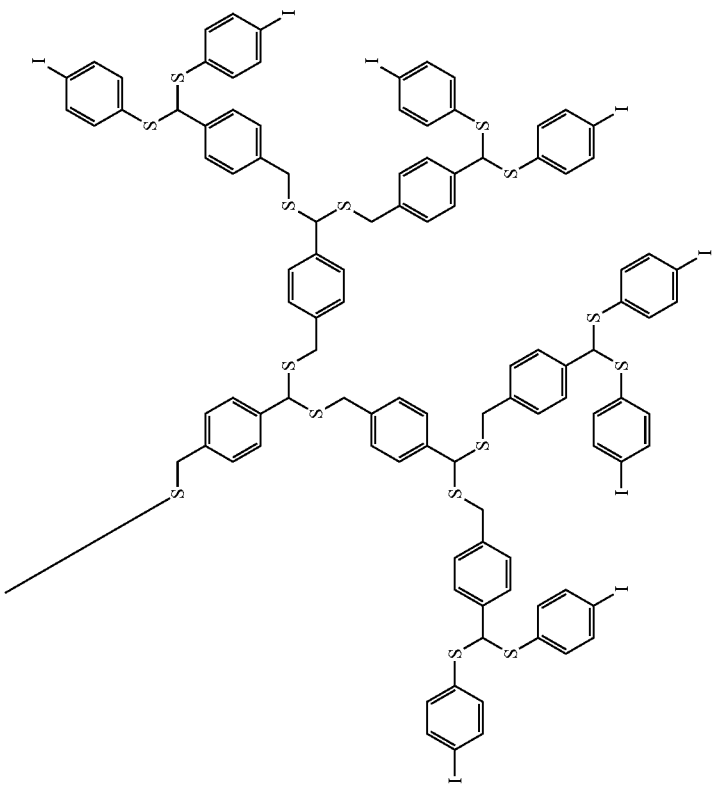
-continued
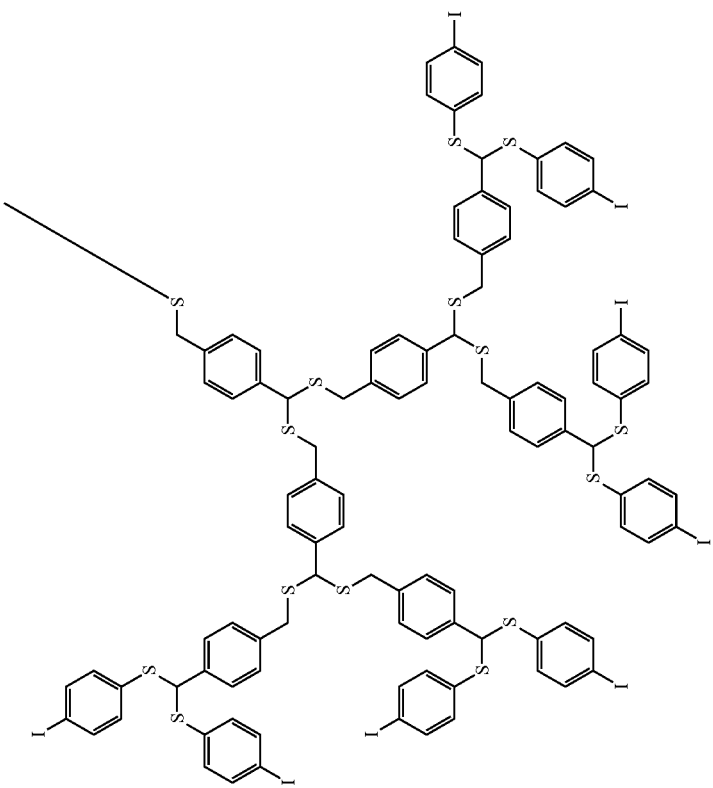

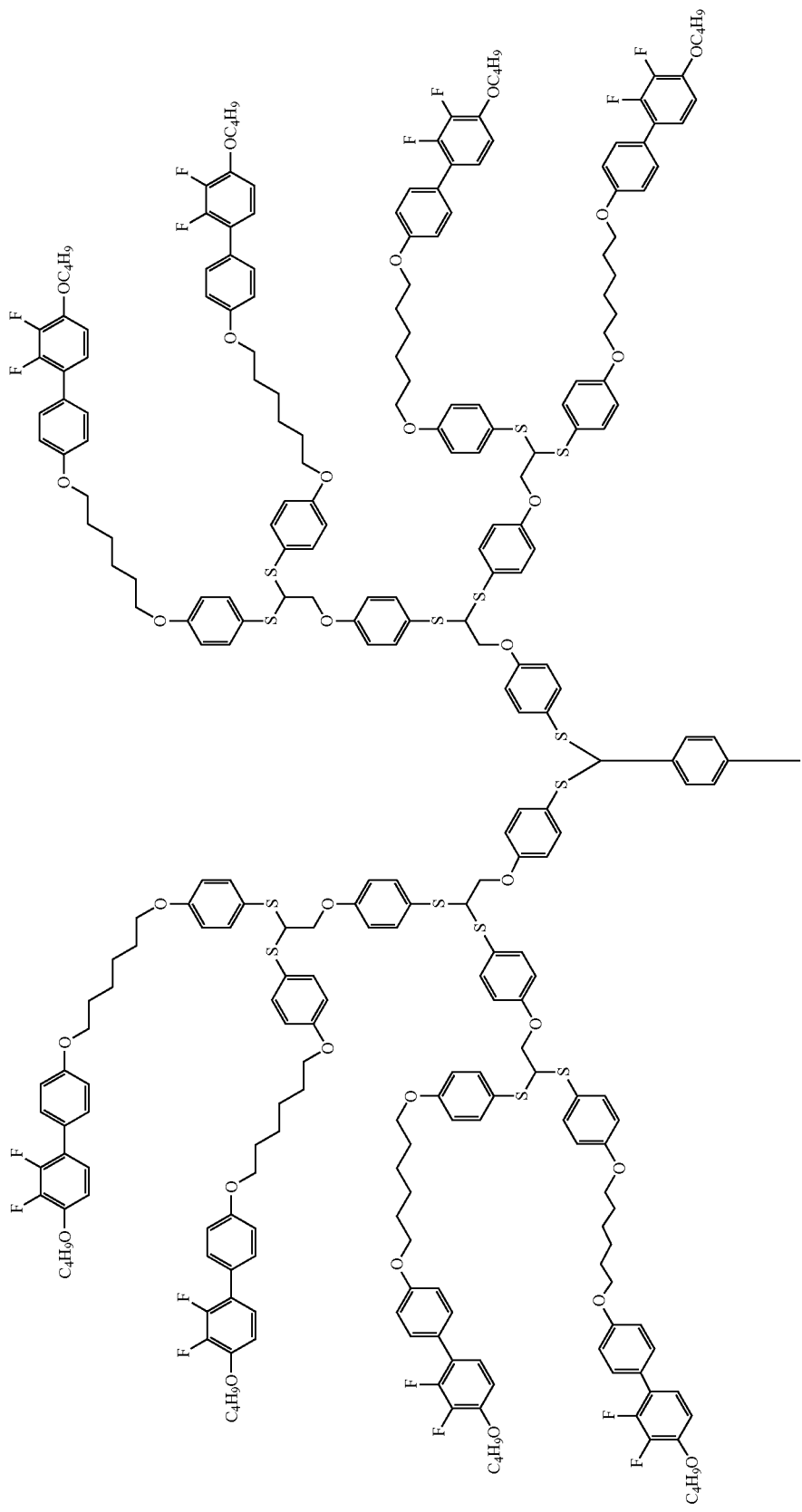
(15)

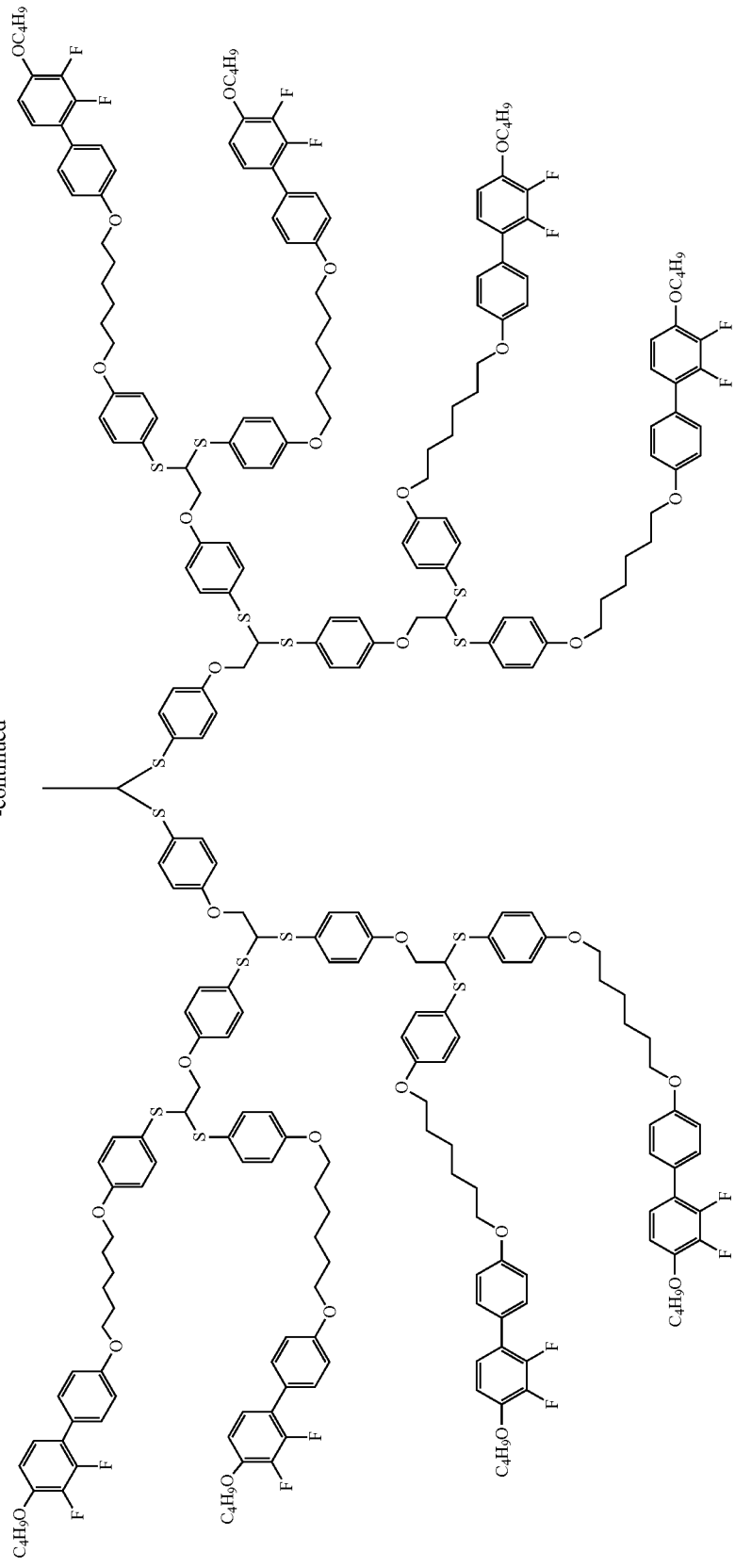

-continued
(16)
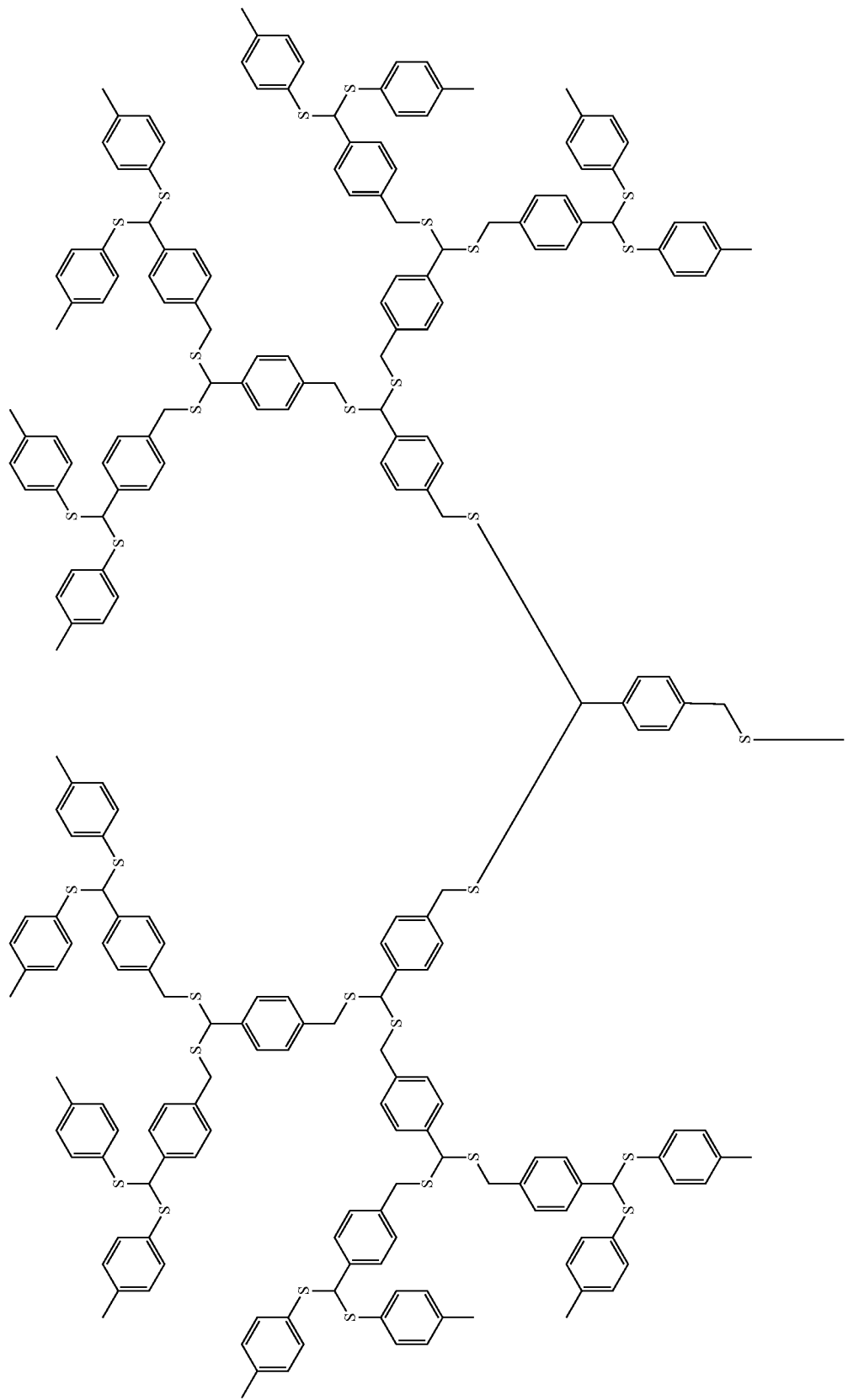

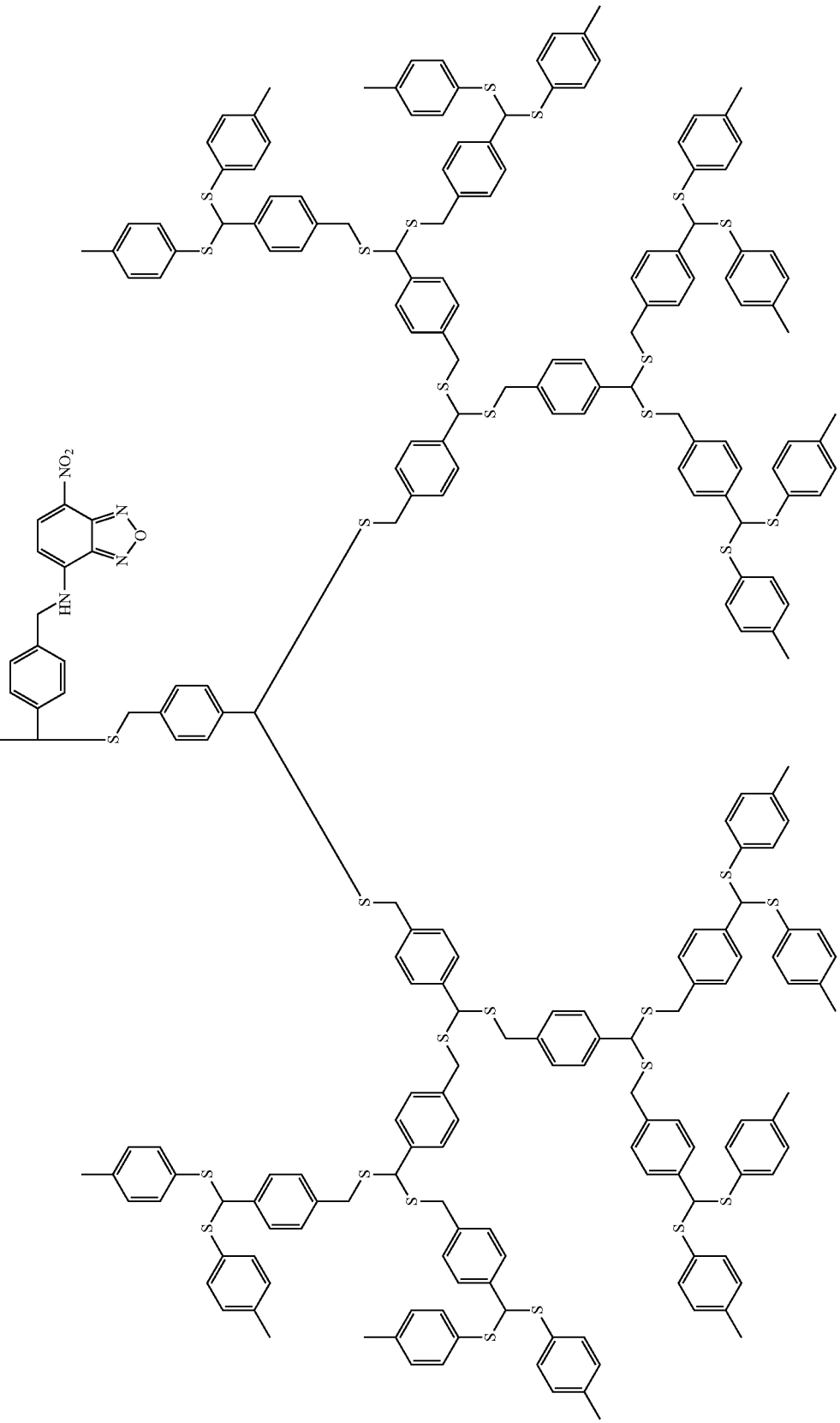

-continued
(17)
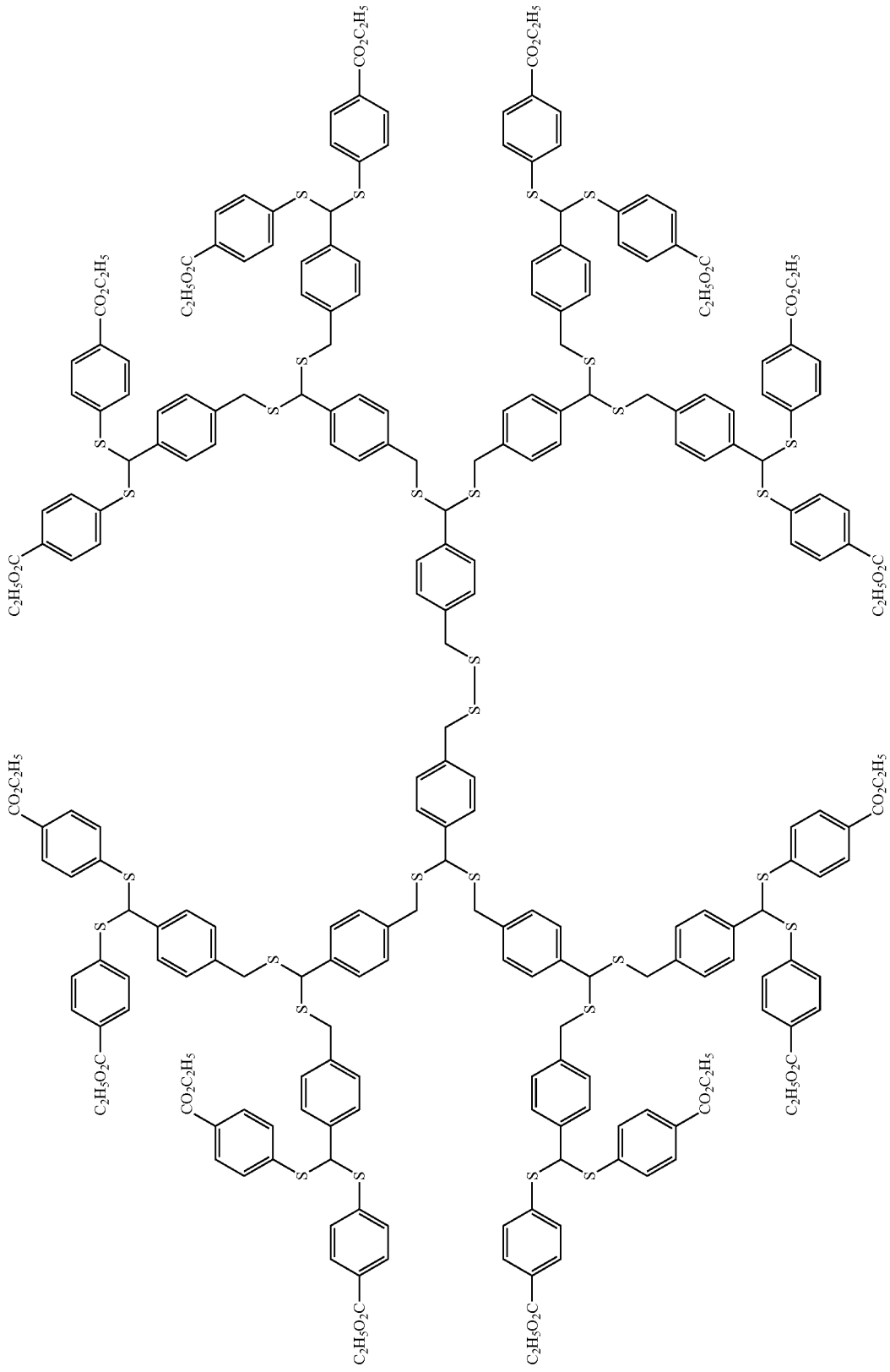

-continued
(18)
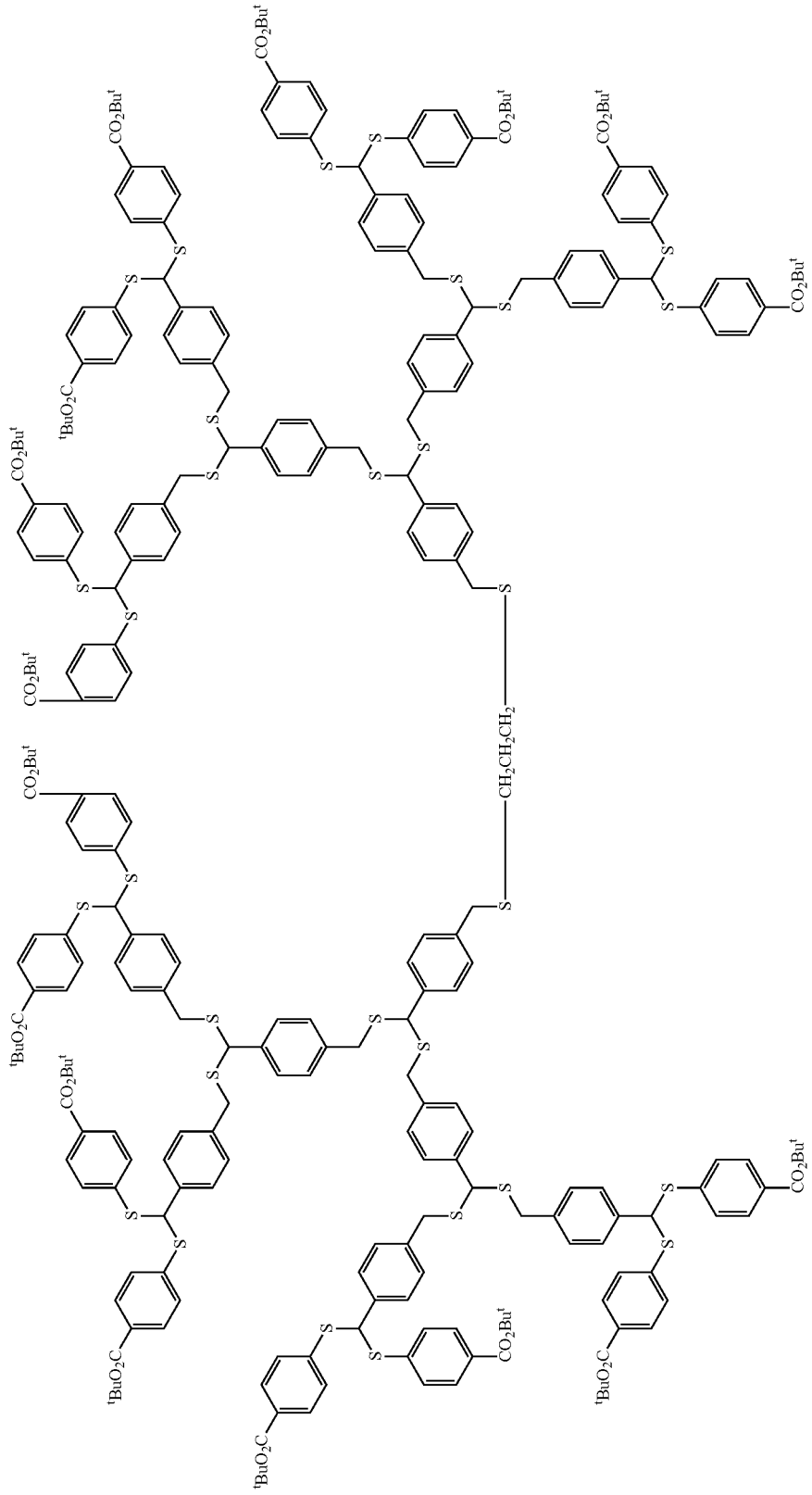

(19)
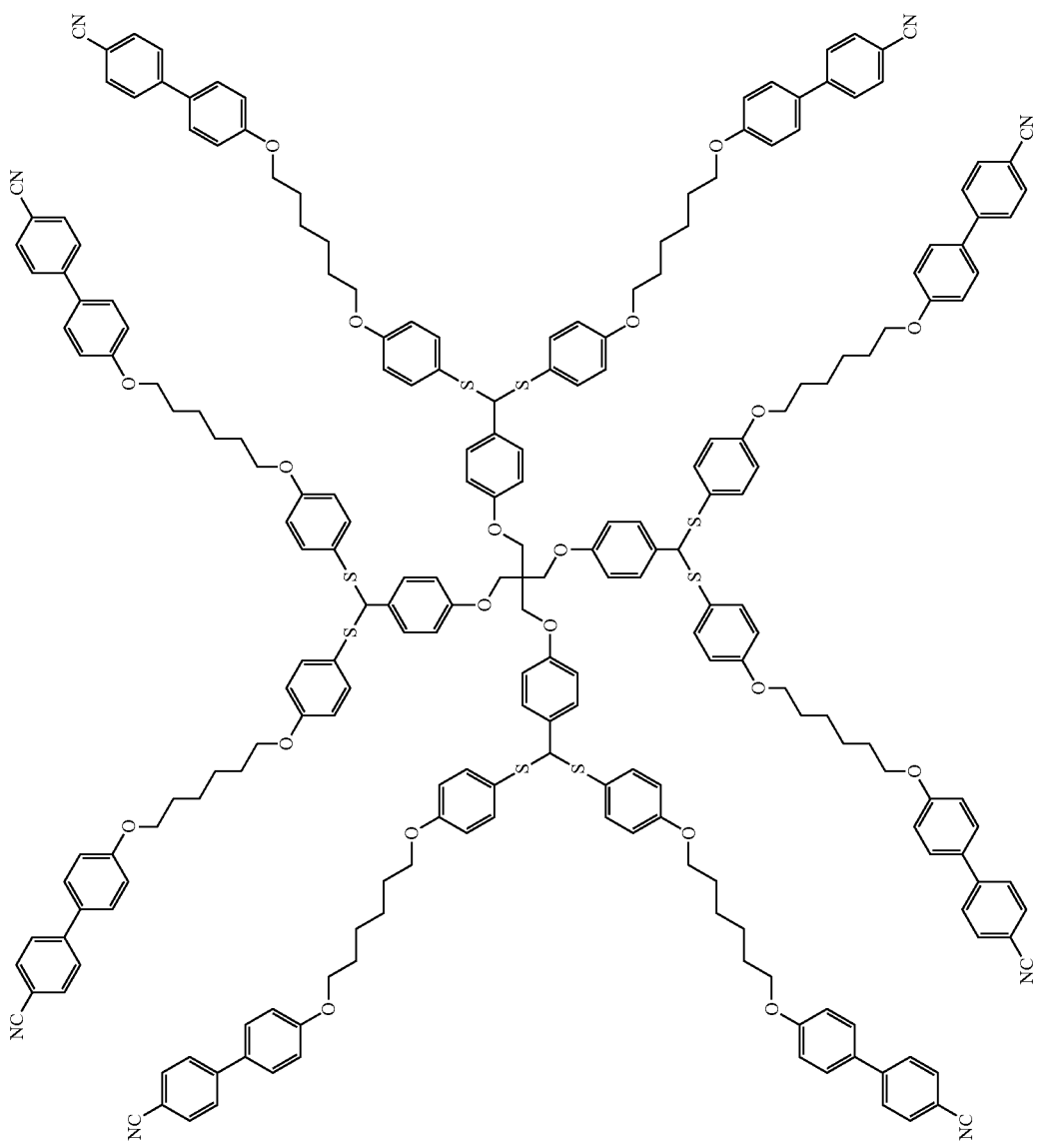

-continued
(20)
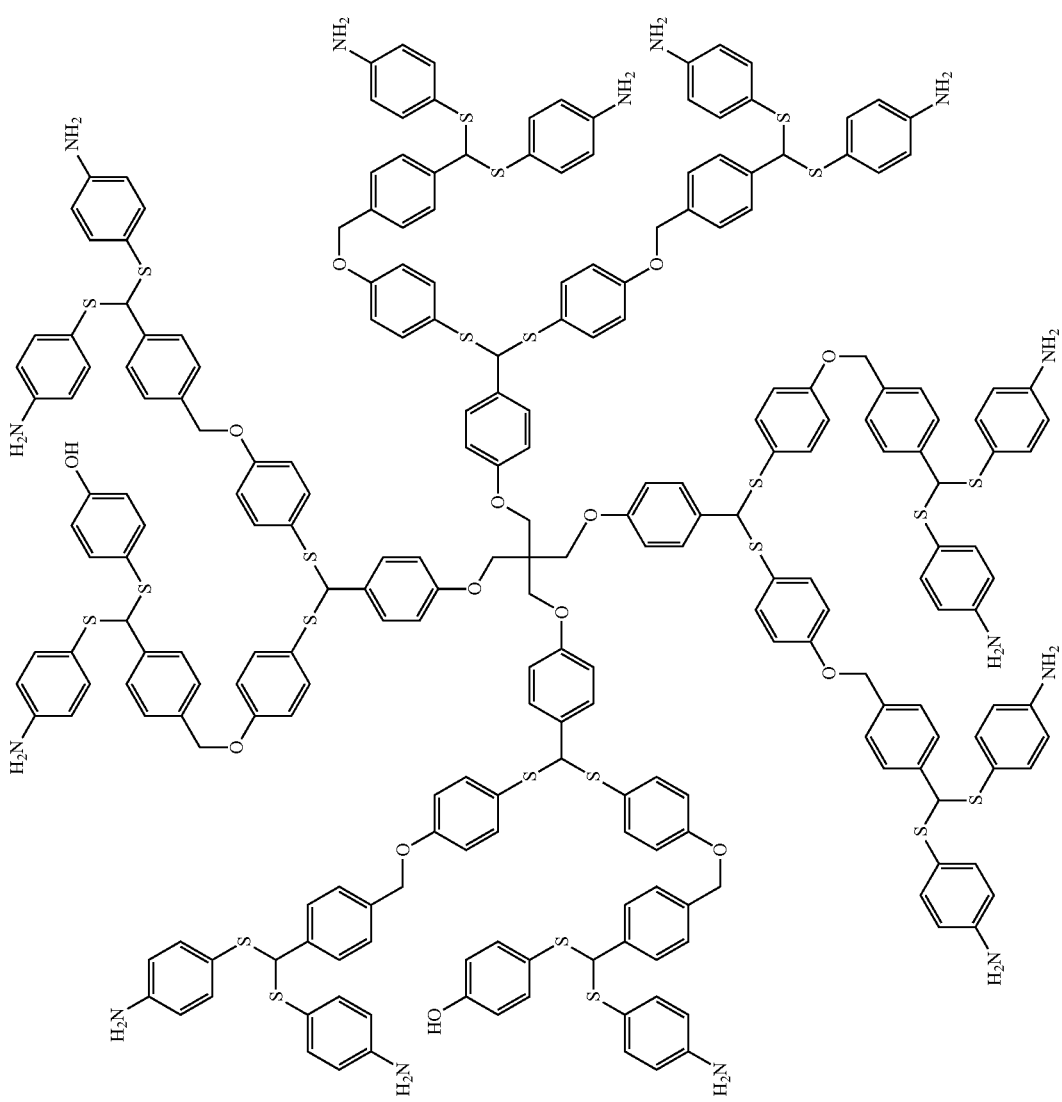

(21)
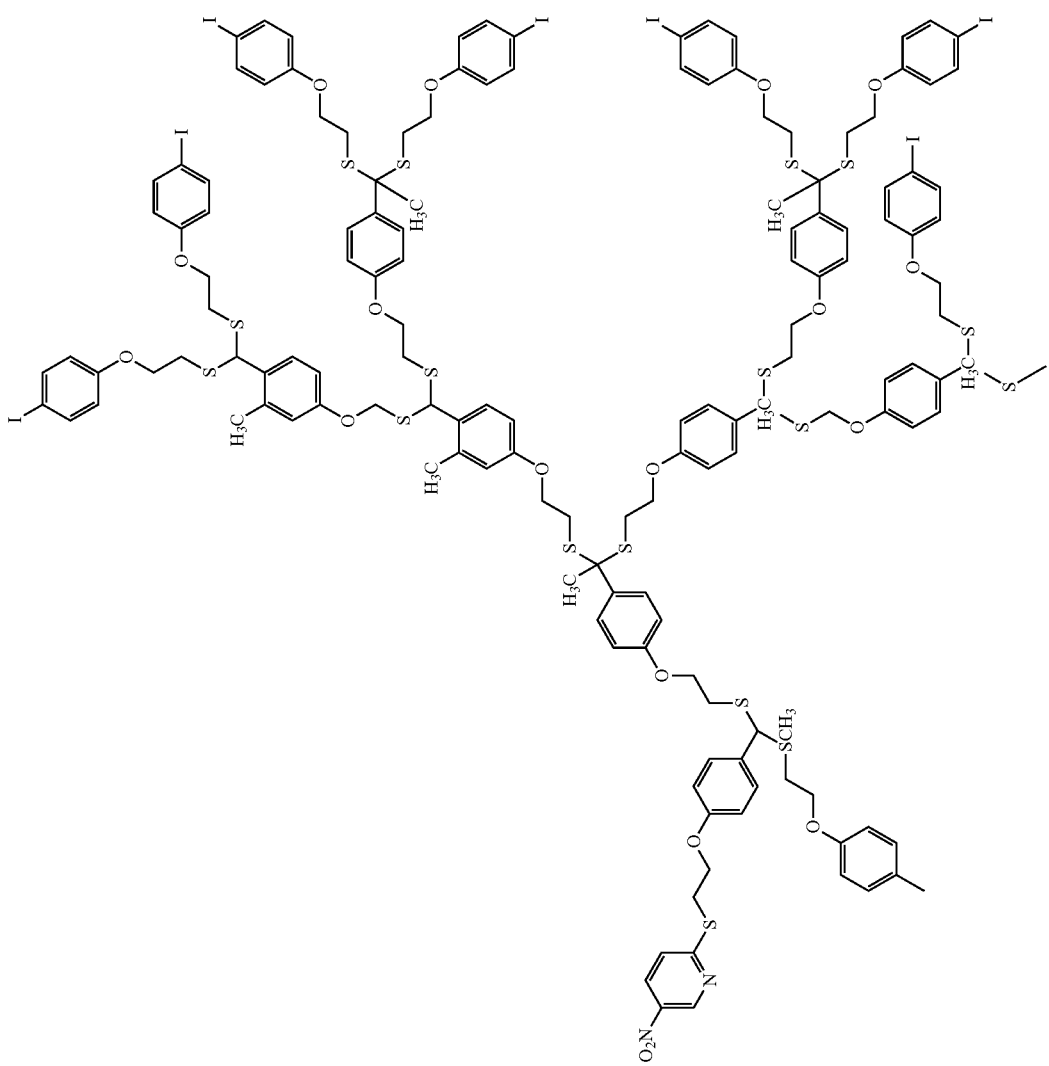

-continued
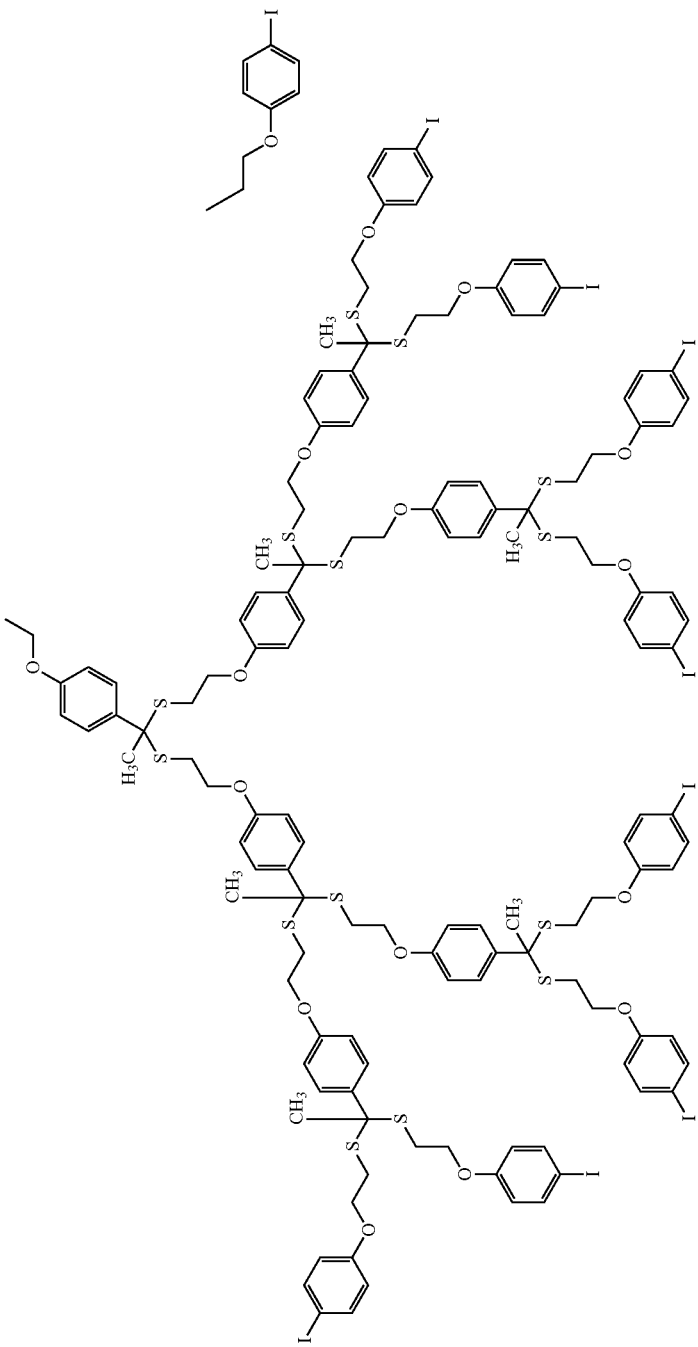

-continued
(22)
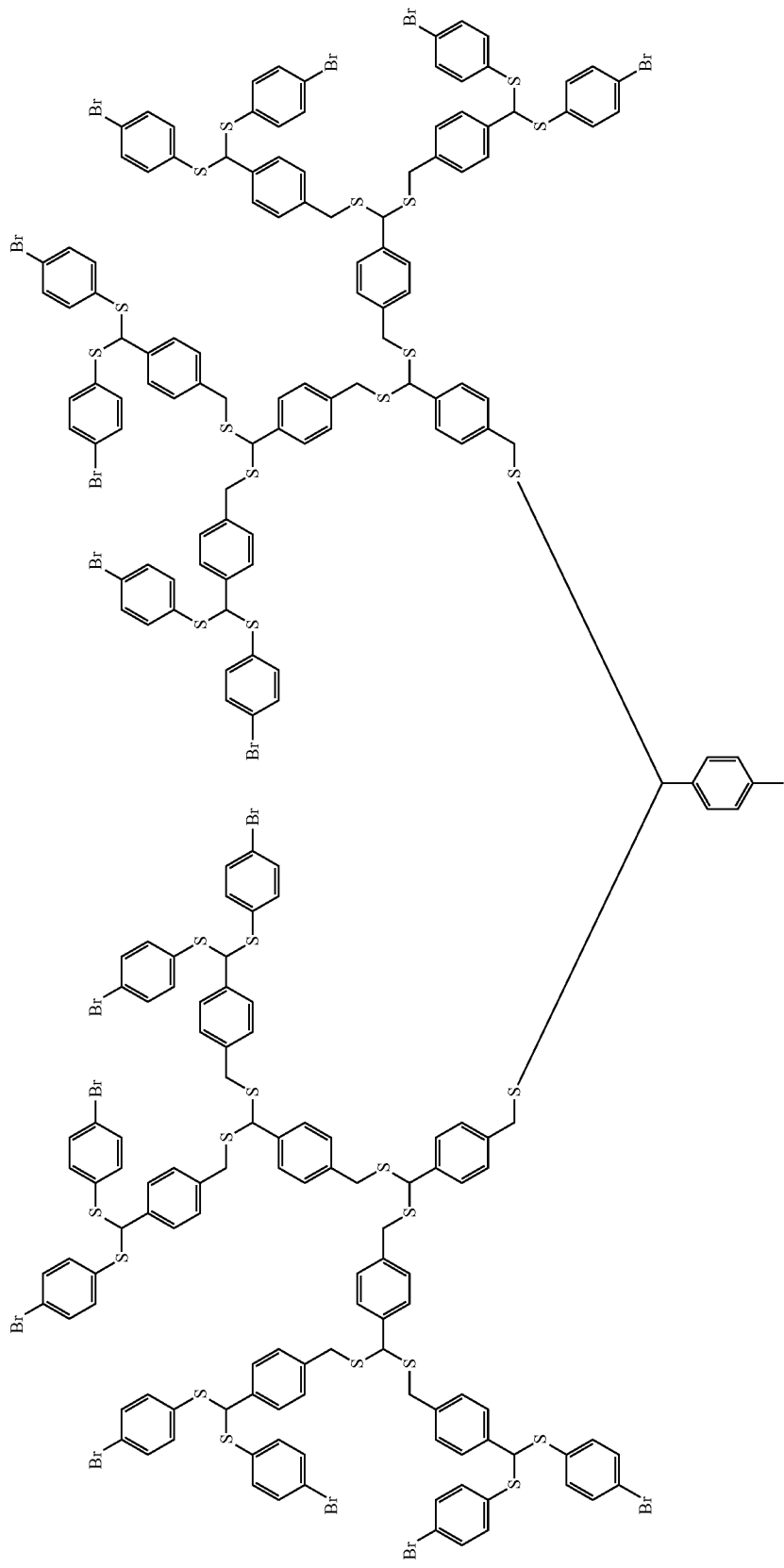

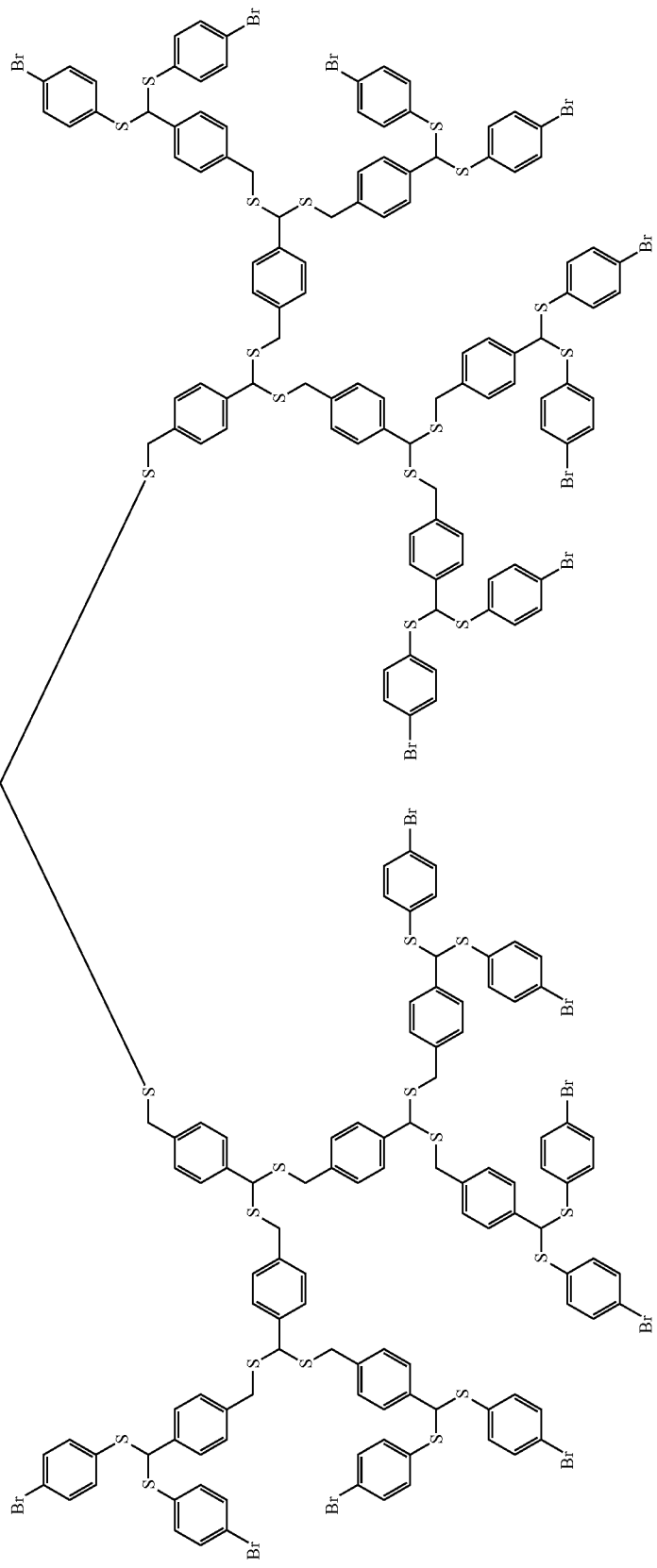
-continued

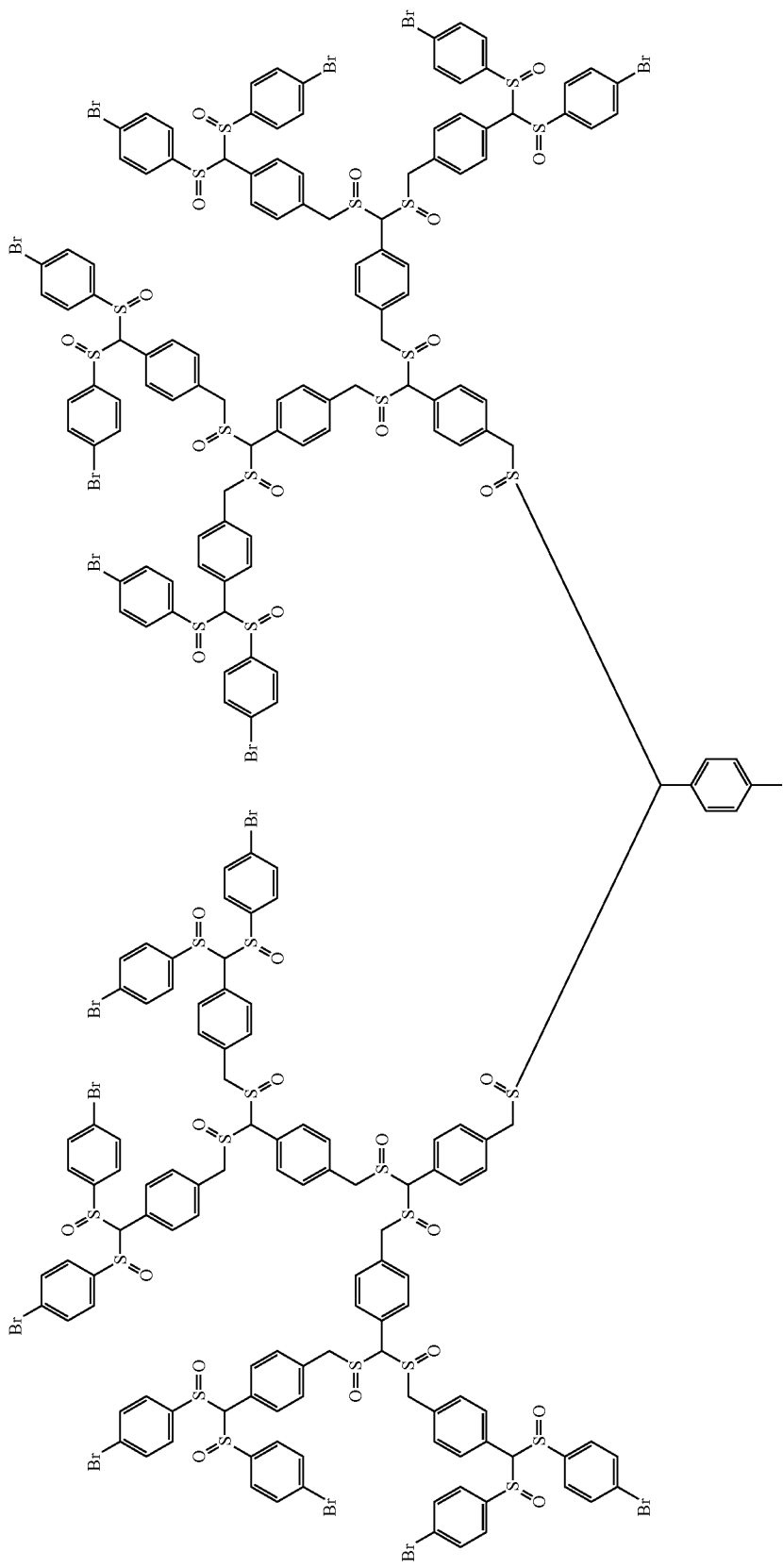
(23)

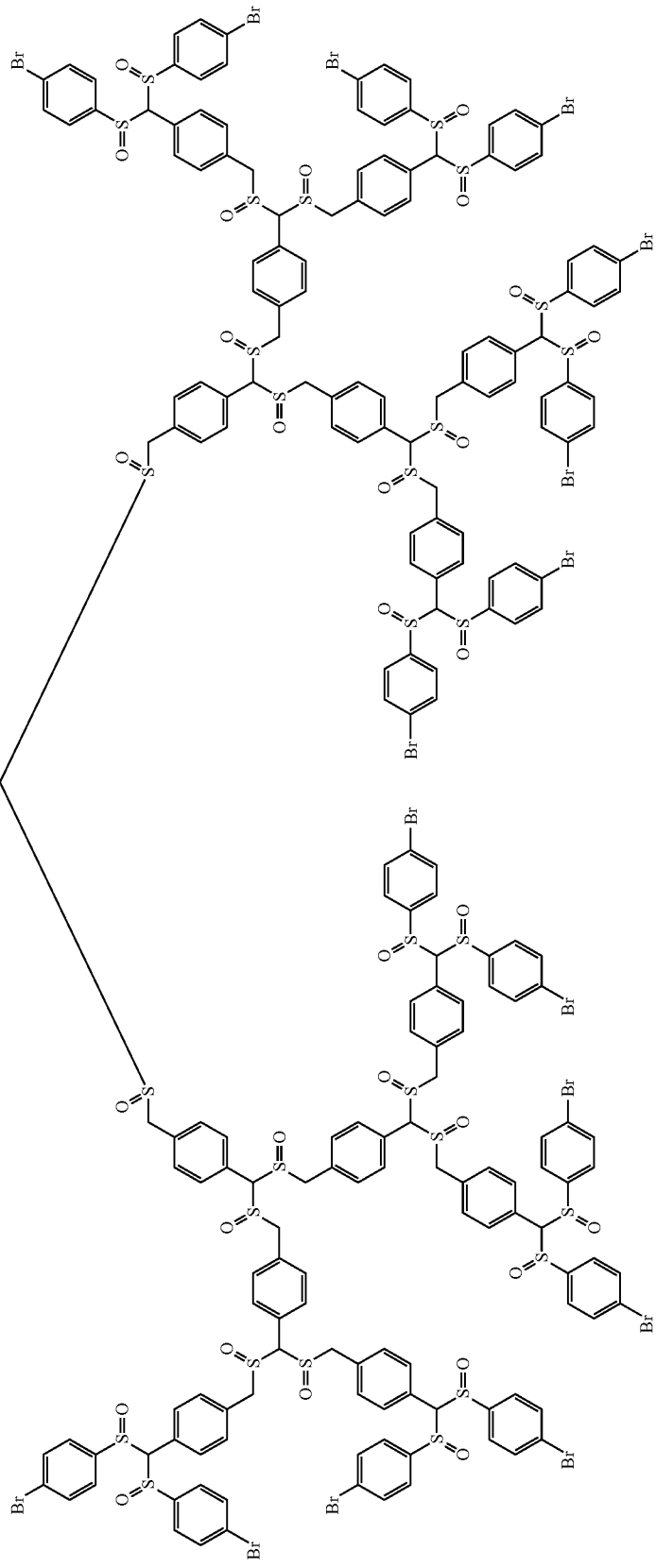

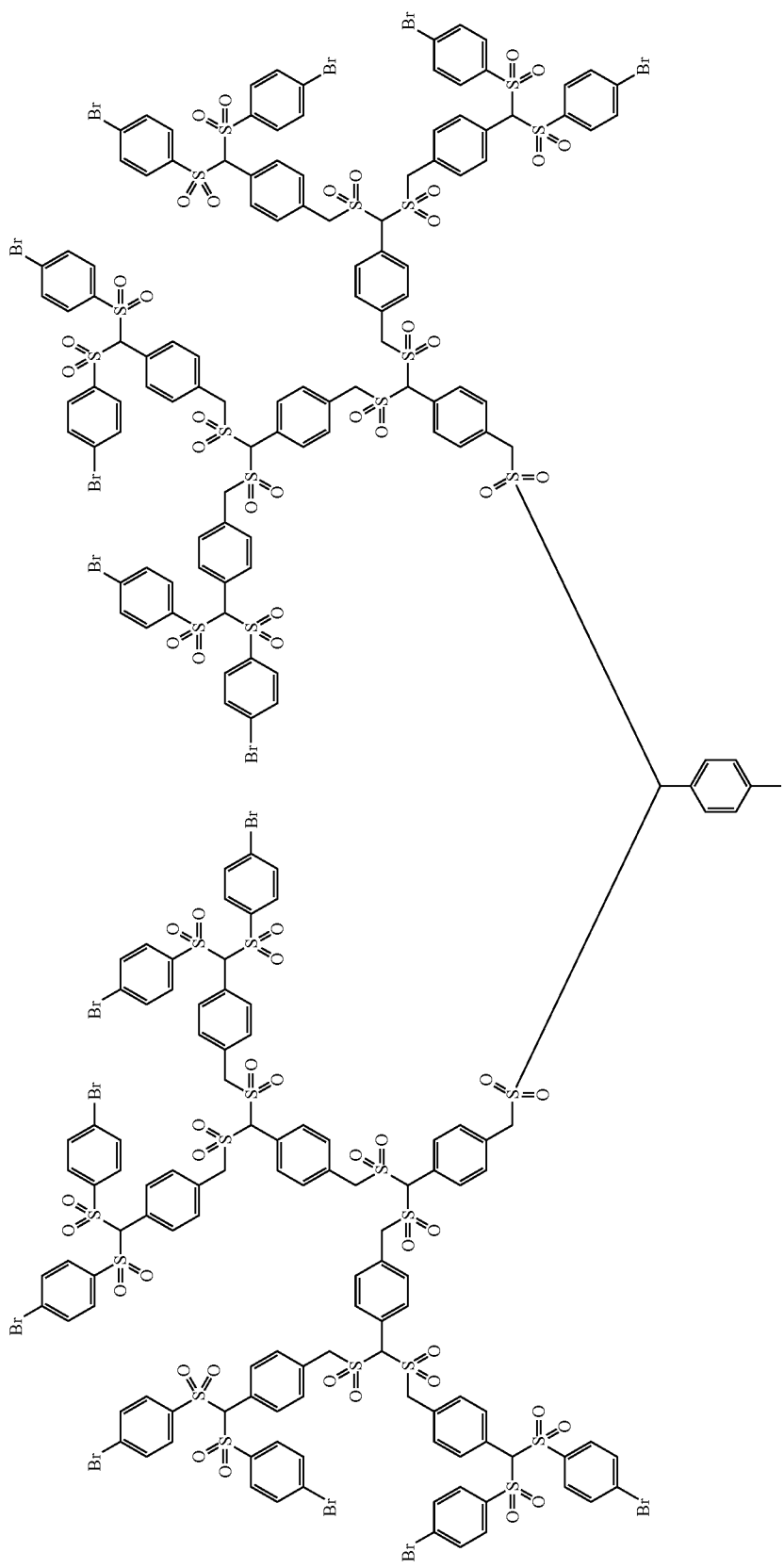

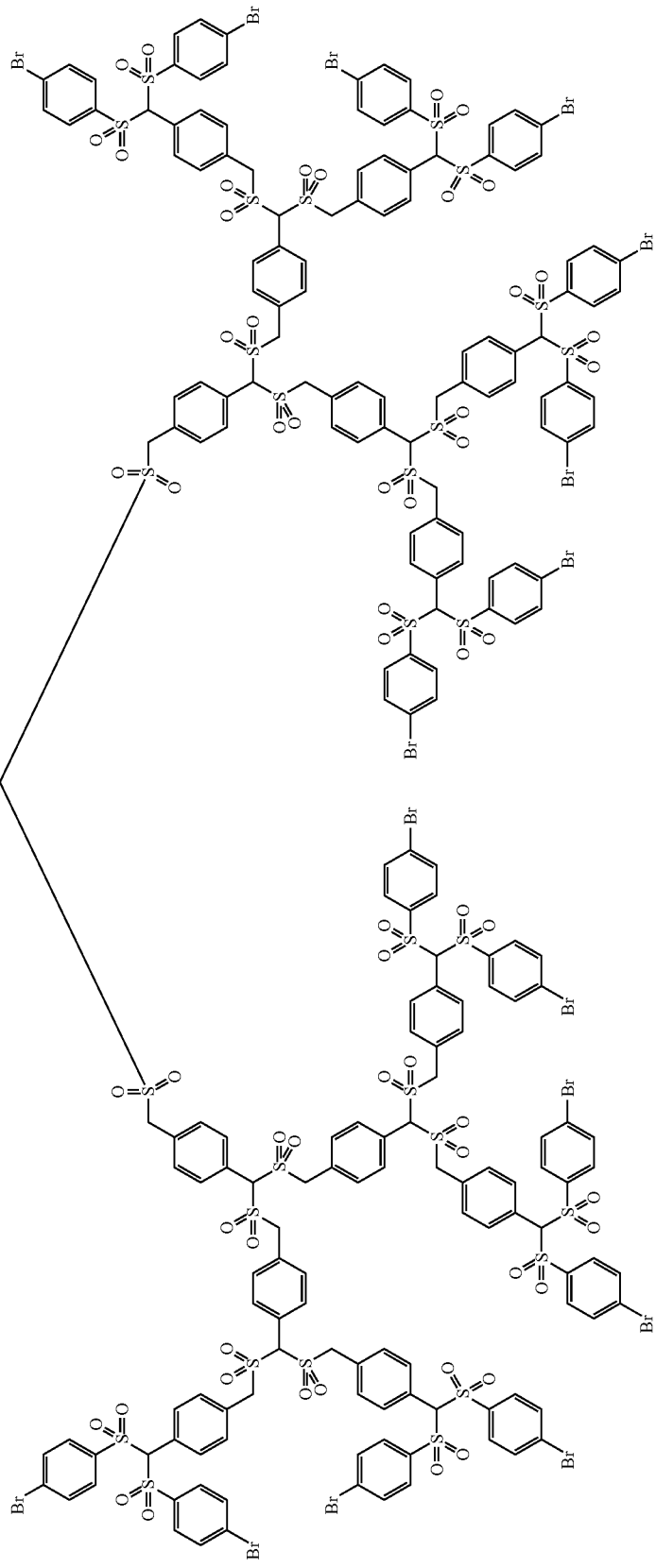
-continued

The synthesis method of the compound of the present invention is described hereinafter.

The compound of the present invention can be particularly effectively synthesized by a method called the "convergent method," among dendrimer synthesis methods.

Matters which are not referred to in the following description on this synthesis method are described in detail in Chemical Review, vol. 101, pp. 3819-3867 (2001), which is described on general synthesis methods of dendrimer and dendron. Reference documents cited therein also can be referred to herein.

First, the method of producing a dendron or dendrimer of the present invention according to the convergent method, is roughly described in below:

A first step is to subject a thiol having a functional group corresponding to a surface terminal to reaction with a carbonyl compound having a protected thiol moiety or an equivalent thereof, to form a thioacetal. A second step is to convert the protected thiol group of the resultant thioacetal to a thiol. The thus-obtained thiol compound is a thiol whose number of generation is higher by one than that of the thiol to be used in the first step. In the second step, the conversion may be attained by one step, or by two or more steps.

The first step and the second step are referred to as one cycle. When this cycle is carried out repeatedly, a dendron whose number of generation is larger can be synthesized. Carbonyl compounds having protected thiol moieties or equivalents thereof, each of which be used in the first steps in plural cycles, may be the same or different.

By oxidizing a sulfide, it can be converted to a sulfoxide or sulfone. As the method therefor, any usual oxidizing method can be used. For example, any of various oxidizing agents may be used, and examples of the oxidizing agent include hydrogen peroxide; hydroperoxides, e.g. t-butylhydroperoxide; peracids, e.g. m-chloroperbenzoic acid; persulfuric acids, e.g. oxone; N-oxides, e.g. N-methylmorpholine-N-oxide; metal (per)oxides, e.g. potassium permanganate; and perboric acid. It is preferred to use, as a solvent to be used in the method, water, a halogen-containing solvent, e.g. methylene chloride or chloroform, a carboxylic acid solvent, e.g. acetic acid or propionic acid, or an ether solvent, e.g. tetrahydrofuran or diethyl ether.

The dendron or dendrimer of the present invention can have a variety of functional groups on the terminal surface. If necessary, the group(s) can be formed, first by producing the dendron or dendrimer in the state the groups are protected, and then deprotecting the groups. The functional group may also be used to bond another compound to the dendron or dendrimer, according to a target function. Examples of the functional group include a mercapto group, a hydroxyl group, a halogen atom (e.g. fluorine, chlorine, bromine, and iodine), a hydrazino group, a cyano group, an isocyanato group, an isothiocyanato group, a thiocyanato group, a carboxyl group, a sulfo group, an acyl group, a formyl group, an amino group, an alkenyl group, and an alkynyl group.

The dendron or dendrimer of the present invention is soluble in an ordinary organic solvent, such as tetrahydrofuran, toluene, ethyl acetate, methylene chloride, and chloroform, and it is excellent in formability or workability. Thus, the compound of the present invention can widely be used for the above-mentioned usages or applications.

Some features of the compound of the present invention are described in the above, and the compound of the present invention can be used in a variety of applications or usages. As a function of a dendrimer or dendron, a great number of applications are suggested, for example, an application, in which a functional group is bonded to the terminal of the compound, and the function of the surface thereof is used; an application, in which a medicine, a drug, or the like is contained or capsulated in the compound, and use is made of the function of releasing the substance by action of stimulus, such as light or heat; an application, in which a dye or a fluorescent dye is contained or trapped in the compound, and use is made of the function of stabilizing the dye(s), decreasing interaction between the dyes, or arranging the dye(s) regularly. The compound of the present invention can be applied to any of the above applications or usages.

For example, Angew. Chem. Int. Ed. vol. 40, p. 74 (2001) describes a large number of methods, by using a dendrimer or dendron, to cause a functional compound to be contained or capsulated therein. The compound of the present invention can be applied to a variety of applications or usages, for example, the application thereof for charge transfer, as described in Journal of American Chemical Society, vol. 118, p. 3978 (1996), and ibid. vol. 121, p. 10658 (1999); the application for laser oscillation, as described in Applied Physics Letter, vol. 80, p. 7 (2002); the application to optical amplification function, as described in O Plus E, p. 998 (August, 1998); the application to a photo-curable resin containing a dye therein, as described in JP-A-2003-327645; the application to an organic EL light-emitting element or a liquid crystal display device, as described in JP-A-2003-277741; the application to an ink composition, as described in JP-A-6-57191; and the application to an ion conductive electrolyte, as described in JP-A-2003-327687. The core of the dendrimer of the present invention, the focal point of the dendron of the present invention, a functional group of the terminal (surface) of the dendrimer and dendron, and the style of the branch structure thereof can be appropriately selected, according to the above examples of applications or usages. Further, the scope of the present invention is not limited to the above-mentioned examples, and the present invention may be applied to a broader scope.

Next, the second embodiment of the present invention is described below.

The present inventor, having repeatedly made eager researches on the problems in the conventional methods, found that the method of the present invention as described in detail below, makes it possible to enhance the selectivity in synthesis of a dendron or dendrimer, and to decrease burden for the purification thereof.

Specifically, the present inventor noticed that in general a focal point moiety has a lower molecular mass than a dendron as a raw material and it can be more easily removed; and the inventor has considered that only the focal point moiety is caused to remain as a molecule species which should be substantially removed away in the reaction system, to carry out purification easily. Further, the present inventor has made various investigations about reaction conditions for causing such a condition, and conduct experiments, so as to attain the present invention.

In the method of the present invention, when a dendron or dendrimer has n branches, the growth of each of the branches is completed every generation one by one. Then, the formation of the next generation is advanced. It is preferable that, as a structure in which the number of grown branches is larger is formed, the rate of reaction for forming such a structure becomes larger, in each of the generations.

In the method of producing a dendron or a dendrimer, in which a (g+1)th generation is formed by forming n branches from a gth generation, a reaction satisfying the following formula (A), preferably a reaction satisfying the following formula (B) as well as formula (A), is utilized, to suppress occurrence of an intermediate(s):

$$k_1 < k_m \qquad \text{Formula (A)}$$

$$k_{m-1} < k_m < k_n \qquad \text{Formula (B)}$$

wherein n is an integer of 2 to 5, and g is an integer of 1 or more, m is an integer of 2 or more but less than n, and wherein $k_1$ represents a rate of growth reaction from the gth generation to the (g+1)th generation, in which only one branch has grown from the gth generation; and $k_m$ represents a rate of reaction from a structure in which (m−1) branches out of the n branches have grown to a structure in which m branches have grown, i.e. only one branch has grown from the former structure to the latter structure.

In this way, without producing any intermediate substantially, a target compound of said reaction can be obtained, thereby making it possible to cause a condition that only a focal point moiety remains in the reaction system as a molecule species which should be substantially removed away. As a result, the synthesis of the dendrimer or dendron can be significantly simplified. Herein, the wording "without producing any intermediate substantially" means that any intermediate is present only at a very low concentration (preferably 3% or less by mol to the raw material(s)) during the reaction.

In the present invention, the above-mentioned step (stage) of forming n branches is appropriately repeated, whereby a dendron or dendrimer having an arbitrary generation number can be produced.

The reaction in the present invention can be preferably represented by a scheme illustrated below. One preferable example of the present invention, preferably in the second embodiment, is a method of synthesizing a dendron or dendrimer, which satisfies the following condition:

$$k_1 < k_2 < \ldots < k_n$$

in a reaction for forming a branch structure of said dendron or dendrimer, as illustrated by the following formula (II):

Formula (II)

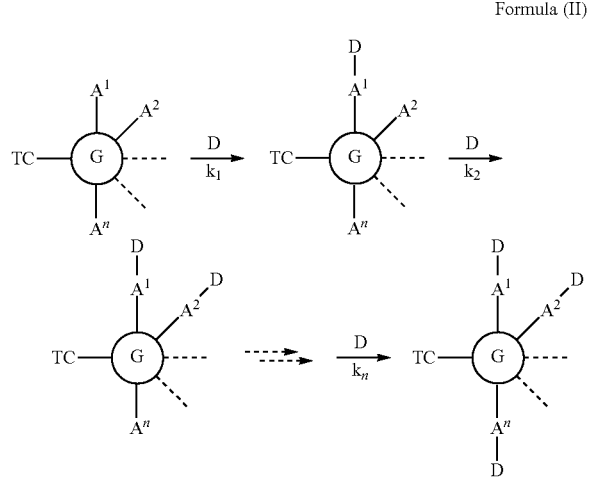

wherein, in formula (II), TC designates a linkage to a former generation in the direction to a focal point of the dendron, or it designates a linkage to a former generation in the direction of a core of the dendrimer; G represents a group containing at least one carbon atom; $A^1, A^2 \ldots$, and $A^n$ mean that G can form n bonds; n represents an integer of 2 to 5; $k_1, k_2 \ldots$, and $k_n$ represent rate constants of respective reactions; and D represents a monovalent group for forming a moiety at the surface terminal side of the dendron or dendrimer.

Examples of the reaction which satisfies the above-mentioned condition and can be applied to the present invention include the followings. The reactions are described, together with some concrete examples.

1) Substitution reaction, in which by a first substitution the electron-donating ability of a product after said first substitution is increased as compared to a starting substance, so that a second substitution in the said product and the subsequent reaction(s) thereto become speedier Examples of this reaction include acetalization reactions (e.g. thioacetalization reaction), and Friedel-Crafts reaction-type alkylation.

Concrete examples of this type are shown below.

Concrete examples

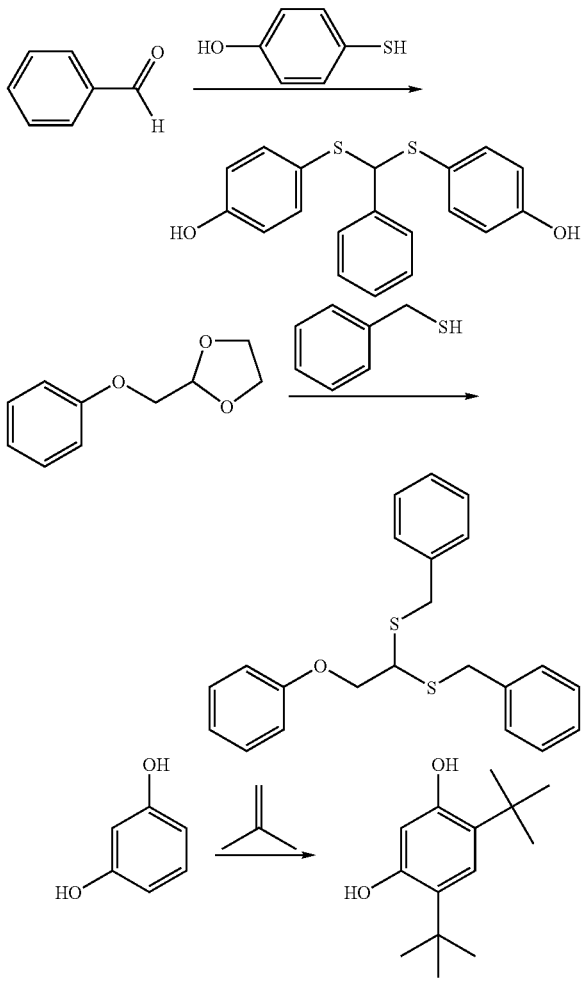

2) Substitution reaction, in which by a first substitution the electron-withdrawing ability of a product after said first substitution is increased as compared to a starting substance, so that a second substitution in the said product and the subsequent reaction(s) thereto become speedier Examples of this reaction include addition/elimination reaction in which electron-withdrawing ability is increased by substitution reaction (e.g. aromatic nucleophilic substitution reaction, or conjugated addition/elimination reaction).

Concrete examples of this type are shown below.

Concrete examples

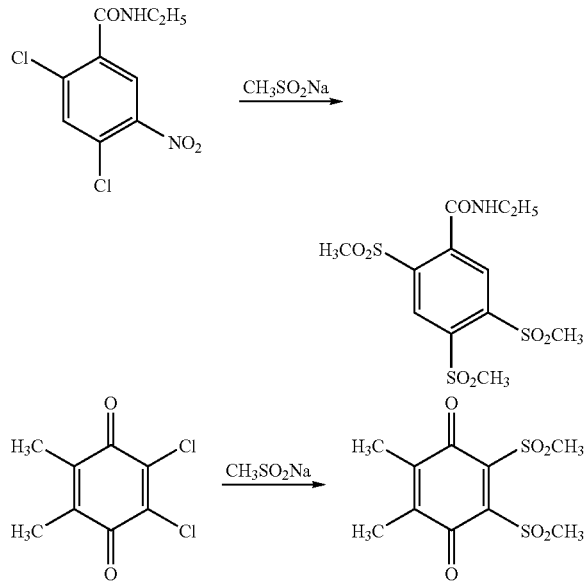

Among the above-mentioned reactions, acetalization reaction is particularly preferable for synthesizing a dendron or dendrimer, and thioacetalization reaction is most preferable therefor, from the viewpoint of chemical stability of the product and high usability in general purposes. In other words, reaction for forming a thioacetal by subjecting a thiol to reaction with a carbonyl compound or an equivalent thereof, can be used as reaction for forming a branch structure of a dendron or dendrimer.

It has not been hitherto known to use a thioacetal as a chemical structure for forming a branch structure as a recurring unit of a dendrimer or dendron. Accordingly, any compound obtained by this method of the present invention is entirely novel.

The method of forming a thioacetal is described hereinafter. In general, a thioacetal structure can be formed via a reaction of a carbonyl compound or an equivalent thereof with a thiol, in the presence of an acid catalyst. The structure can be formed under a basic condition also. In either case, it is possible to set reaction conditions for making the rate of reaction for bonding a second branch chemical structure of the same generation larger than the rate of reaction for bonding the next generation, to a first branch. In the case of the reaction in the presence of an acidic catalyst, the carbonyl compound is preferably an aldehyde (e.g. an aromatic aldehyde, or an aliphatic aldehyde), or a ketone (e.g. an aromatic ketone, or an aliphatic ketone). The carbonyl equivalent is preferably any (cyclic or non-cyclic) acetal thereof; any (cyclic or noncyclic) hemiacetal thereof, an imine, or the like. The acetal may be of a dialkoxy type or a diaryloxy type, and may be a symmetrical acetal or an asymmetrical acetal.

The thiol is preferably an aromatic thiol, an aliphatic thiol, a hetero aromatic thiol, or the like.

Preferable examples of the acid catalyst that can be used in the reaction include proton acids (e.g. sulfuric acid, methanesulfonic acid, p-toluenesulfonic acid, trifluoroacetic acid, trifluoromethanesulfonic acid, oxalic acid, hydrochloric acid, and hydrobromic acid); and Lewis acids (e.g. magnesium bromide, tellurium chloride, tungsten chloride, zirconium chloride, iodine, N-bromosuccinimide, indium chloride, indium trifluoromethanesulfonate, scandium trifluoromethanesulfonate, and boron trifluoride etherate).

The reaction may be conducted with no solvent, but a reaction solvent is generally used, and a halogen-containing solvent, such as methylene chloride, chloroform, or dichloroethane, can be used as the reaction solvent. Besides the above solvent, use may also be made, for example, of a low polar solvent, such as toluene, benzene, or xylene; an ether solvent, such as tetrahydrofuran, dioxane, or diethyl ether; an alcohol solvent, such as methanol, ethanol, isopropyl alcohol, t-butanol, or n-butanol; or an ester solvent, such as ethyl acetate, methyl acetate, or butyl acetate.

When a thioacetal is formed under a basic condition, any one of geminal dihalogen compounds is used as the carbonyl equivalent, and the formation can be attained by nucleophilic substitution reaction. Among the geminal dihalogen compounds, a benzylidene dihalogen compound can be preferably used. The halogen atom to be released in this case is preferably a chlorine, bromine or iodine atom, particularly preferably a bromine atom.

The base is preferably a base making it possible to dissociate thiol. Preferred examples thereof include inorganic bases, such as potassium carbonate, sodium carbonate, sodium hydrogencarbonate, sodium hydroxide, potassium hydroxide, cesium carbonate, and sodium hydride; as well as triethylamine, diazabicycloundecene (DBU), N-ethyldiisopropylamine, potassium t-butoxide, and sodium t-amyloxide.

The following may be used as a reaction solvent: e.g. an aprotic polar solvent, such as acetonitrile, dimethylformamide, dimethylacetoamide, dimethylsulfoxide, or sulfolane; an ether solvent, such as tetrahydrofuran, dioxane, or diethyl ether; an alcohol solvent, such as methanol, ethanol, isopropyl alcohol, t-butanol, or n-butanol; an ester solvent, such as ethyl acetate, methyl acetate, or butyl acetate. Preferably, an aprotic polar solvent is used.

The reaction can be conducted at an appropriately-set temperature under any one of the acid catalyst condition and the basic condition. In general, the reaction temperature is set preferably in the range of $-80$ to $200°$ C., more preferably in the range of $-50$ to $140°$ C.

The molar ratio in reaction of the thiol to the carbonyl compound or the equivalent thereof is generally about 2/1, and the molar ratio is preferably from 10/1 to 0.5/1, more preferably from 4/1 to 1/1, considering easy isolation of a target compound, and other factors.

Next, the third embodiment of the present invention is described below.

The present inventor noted that, in a thioacetal-forming reaction using a thiol and an excessive amount of a carbonyl compound (or an equivalent thereof), intermediates are hardly observed, and only the target compound (thioacetal) and the carbonyl compound as the raw material are present at the time of the completion of the reaction. The present inventor then further found out that this reaction can be used to synthesize a dendron or dendrimer, to largely simplify isolation and purification of the target compound.

Thus, the present inventor has repeated further investigations on the synthesis of a dendron or dendrimer, by repeat use of a thioacetal-forming reaction, and thereby clarified the following: A thioacetal structure is stable against strong acidity and strong basicity; however, when a thiol having thioacetal in its molecule is used to conduct a thioacetalization reaction, in a nonpolar solvent (a solvent most common for a thioacetalization reaction), such as methylene chloride, chloroform, or toluene, in the presence of an acid catalyst, a thioxy group for forming a thioacetal structure causes a scramble, so that reaction products may become a highly complicated mixture. I assume that this would be based on a mechanism similar to the mechanism described in Synlett, No. 6, pp. 984-986 (2002). When a thioacetal is formed by reaction of a thiol having no thioacetal structure with a carbonyl compound, the same product is given even if a scramble is caused. Accordingly, the above-mentioned scramble phenomenon is a problem peculiar to the case of using a thiol having a thioacetal structure. However, no method for solving this problem has been known hitherto. An important theme is to find out a new method for solving this.

The present inventor, having eagerly investigated, has found out that the kind of a reaction solvent produces a large effect on the reaction, and the present invention has been attained based on this finding.

The method of the present invention for producing a thioacetal compound, comprises the step of: subjecting a thiol compound having in the molecule thereof a thioacetal structure, to a reaction with a carbonyl compound or an equivalent thereof, in the presence of a catalyst, in a reaction solvent selected from ethers, esters, amides, sulfoxides, alcohols, nitriles, and sulfones, thereby to form a thioacetal structure.

A thiol compound having in the molecule thereof a thioacetal structure has at least one thiol group and at least one thioacetal structure. The thioacetal structure is represented by $R^1$—$C(SR^2)$—$R^3$. Preferably, $R^1$ and $R^3$ each independently represent a group selected from a hydrogen atom, an alkyl group, an aryl group, an alkenyl group, an alkynyl group, and a heterocyclic group. It is not permissible that $R^1$ and $R^3$ are hydrogen atoms simultaneously. $R^2$ is preferably a group selected from an alkyl group, an aryl, group, an alkenyl group, an alkynyl group, and a heterocyclic group. It is preferable that the thiol group is bonded to $R^1$ or $R^3$ and that it is present as an alkanethiol, an arylthiol, or a heterocyclic thiol.

The thiol compound having in the molecule thereof a thioacetal structure in the present invention may have any of various substituents or functional groups which do not take part in thioacetalization reaction. Examples of the substituent or functional group include an alcoholic hydroxyl group, a phenolic hydroxyl group, a halogen atom (e.g. fluorine, chlorine, bromine, or iodine), a nitro group, a sulfo group, a carboxyl group, an amino group, an amide bond, a sulfonamide bond, an ether bond, an ester bond, a urethane bond, a thioether bond, and a urea bond.

In the thioacetalization reaction in the present invention, the reaction mole ratio of the thiol compound having in the molecule thereof a thioacetal structure to the carbonyl compound (or equivalent thereof) is generally about 2/1, and it is preferably from 10/1 to 0.5/1, more preferably from 4/1 to 1/1, considering easiness of the isolation of a target compound.

The carbonyl compound is represented by $R^4$—CO—$R^5$. Preferably, $R^4$ and $R^5$ each independently represent a group selected from a hydrogen atom, an alkyl group, an aryl group, an alkenyl group, an alkynyl group, and a heterocyclic group. It is not permissible that $R^4$ and $R^5$ are hydrogen atoms simultaneously. The equivalent of the carbonyl compound is preferably represented by $R^4$—$CX_2$—$R^5$. $R^4$ and $R^5$ have the same meanings as described above. $X_2$ is preferably selected from an alkoxy group, an aryloxy group, a heteroaryloxy group, and a halogen atom. $X_2$ may be an imino group, a hydroxyimino group, an alkoxyimino group, a sulfonylimino group, an acylimino group, or an aminoimino group.

Preferable examples of the solvent that can be used in the present invention include ethers, such as diethyl ether, diisopropyl ether, t-butyl methyl ether, tetrahydrofuran, tetrahydropyran, dioxane, dioxolane, and anisole; esters, such as methyl acetate, ethyl acetate, butyl acetate, 2-methoxyethyl acetate, diethyl phthalate, and diethyl succinate; amides, such as dimethylformamide, and dimethylacetoamide; sulfoxides, such as dimethylsulfoxide; alcohols, such as methanol, ethanol, isopropyl alcohol, t-butyl alcohol, and n-butyl alcohol; nitriles, such as acetonitrile, propionitrile, and isobutyronitrile; and sulfones, such as dimethylsulfone. It is possible to use a mixed solvent of any combination of these solvents that can be used in the present invention; or a mixture in which at least one of the above solvents that can be used in the present invention is mixed with another solvent(s).

Among these solvents, ethers, esters, amides and nitriles are preferable, and ethers are more preferable, from the viewpoint for making the attainment of a large reaction rate and the suppression of the scramble phenomenon consistent with each other. In particular, cyclic ethers are preferable, and tetrahydrofuran is most preferable, from the viewpoint of the solubility of a dendrimer or dendron having a large molecular mass.

The amount of the solvent to be used in the present invention is not less than the amount making it possible to dissolve 5% by mass or more of all of the reaction agents. The amount is preferably 50% or more, more preferably from 100 to 10,000%, most preferably from 300 to 5,000% by volume to the above-mentioned thiol compound having a thioacetal structure.

The catalyst that can be used in the present invention is preferably an acidic catalyst. Preferable examples of the acidic catalyst include proton acids (e.g. sulfuric acid, methanesulfonic acid, p-toluenesulfonic acid, trifluoroacetic acid, trifluoromethanesulfonic acid, oxalic acid, hydrochloric acid, and hydrobromic acid), and Lewis acids (e.g. magnesium bromide, tellurium chloride, tungsten chloride, zirconium chloride, iodine, N-bromosuccinimide, indium chloride, indium trifluoromethanesulfonate, scandium trifluoromethanesulfonate, and boron trifluoride etherate).

The reaction temperature can be appropriately set in accordance with the solvent and catalyst to be used. It is preferable to make the temperature as low as possible, while a realistic reaction rate is kept, since scramble reaction, which is a side reaction, is apt to occur at a higher temperature. As a practical matter, the temperature is preferably from about −80 to 150° C., more preferably from −80 to 100° C., even more preferably from −40 to 70° C.

According to the present invention, it is possible to provide a novel dendrimer or dendron exhibiting a new function and/or physical property.

According to the present invention, it is possible to provide a effective method of producing a dendron or dendrimer which is easily purified.

According to the method of the present invention, the reaction product is a target dendron or dendrimer containing the starting compounds thereof and the generation of intermediates (products wherein the formation of branches is incomplete) is remarkably restrained. For the reason, the intermediates are restrained from being mixed or produced in the reaction solution. As a result, a burden on the purification of the compound is decreased. Thus, the present invention is preferable for being industrially carried out.

According to the present invention, a target thioacetal compound can be produced while any byproduct is restrained from being generated. As a result, a burden on purification of the target compound is largely decreased. Accordingly, when this production method is used, a dendron or dendrimer, which is a macromolecule, can be effectively produced.

The present invention will be described in more detail based on the following examples, but the invention is not intended to be limited thereto.

EXAMPLES

Example 1

Synthesis of Exemplified Compound (4)

Synthesis [1-1]: Synthesis of 4-(4-(6-bromohexyloxy)phenyl)benzonitrile 40 g of 4-(4-hydroxyphenyl)benzonitrile, 42 g of potassium carbonate, and 250 g of 1,6-dibromohexane were mixed. The resultant mixture was then caused to react in dimethylformamide at 100° C. for 5 hours. After cooled, the resultant was poured into 1 L of water and extracted with chloroform. The resultant was purified by silica gel column chromatography, and then recrystallized from chloroform/hexane, to give the target compound (yielded amount 39 g, and yield 54%).

Synthesis [1-2]: Synthesis of 2-(4-hydroxyphenylthio)pyridine

Under nitrogen atmosphere, 127 g of 4-hydroxythiophenol, 112 g of chloropyridine, and 140 g of potassium carbonate were mixed. To the mixture was added 250 mL of dimethylformamide. The resultant was stirred, heated to 75° C. and further heated at 10° C. for 5 hours. At the time when the reaction completed substantially, the resultant was poured into 1.5 L of water. The precipitated crystals were collected by filtration, washed with water, and dried (yielded amount 184 g, and yield 91.8%).

Synthesis [1-3]: Synthesis of 2-(4-((1,3-dioxolane-2-yl)methoxy)phenylthio)pyridine 30 g of 2-(4-hydroxyphenylthio)pyridine, 27.1 g of 2-bromomethyl-1,3-dioxolane, 31 g of potassium carbonate, and 120 mL of dimethylsulfoxide were mixed. A catalytic amount of sodium iodide was added to the mixture, and then the resultant mixture was caused to react on an oil bath of 95 to 100° C. temperature for 4 hours. Further, the temperature of the oil bath was raised to 120° C., to continue the reaction for 2 hours.

After the completion of the reaction, the system was cooled, and then 800 mL of water was added thereto, to precipitate a crystal. This crystal was collected by filtration, washed with water, and dried. Then, the dried crystal was dissolved into methanol, and subjected to natural filtration. Then, water was added to the filtrate, to precipitate a crystal. The resultant crystal was filtrated and washed with water, to yield 39 g of the target compound (yield 91.1 g).

Synthesis [1-4]: Synthesis of 2-(4-(2,2-bis(4-hydroxyphenylthio)ethoxy)phenylthio)pyridine Into methylene chloride were dissolved 30 g of 2-(4-((1,3-dioxolane-2-yl)methoxy)phenylthio)pyridine, 27.5 g of 4-hydroxythiophenol, and 32 g of p-toluenesulfonic acid, and then the resultant solution was heated under reflux. After the reaction was conducted for 2 days, the solvents were distilled off. Water and ethyl acetate were added thereto, and the solution was made into basicity with potassium carbonate, followed by extraction. The resultant organic phase was concentrated, to precipitate a crystal. This was collected by filtration, washed with a small amount of ethyl acetate, and dried, to give the target compound (yielded amount 38 g, and yield 76.2).

Synthesis [1-5]: Synthesis of 2-(4-(2,2-bis(4-(6-(4-(cyanophenyl)phenoxy)hexyloxy)phenylthio)ethoxy)phenylthio)pyridine 20 g of 2-(4-(2,2-bis(4-hydroxyphenylthio)ethoxy)phenylthio)pyridine and 31 g of 4-(4(6-bromohexyloxy)phenyl)benzonitrile were mixed. Thereto were added 25 g of potassium carbonate and a catalytic amount of sodium iodide, to conduct reaction in dimethylformamide at 85° C. After the completion of the reaction, water was added to the reaction liquid, to precipitate an oily substance. This was extracted with chloroform, and purified by column chromatography (yielded amount 37 g, and yield 85.8%).

Synthesis [1-6]: Synthesis of 2-(4-(2,2-bis(4-(6-(4-(cyanophenyl)phenoxy)hexyloxy)phenylthio)ethoxy)phenylthio)-1-methylpyridinium iodide Into 20 mL of chloroform was dissolved 10 g of 2-(4-(2,2-bis(4-(6-(4-(cyanophenyl)phenoxy)hexyloxy)phenylthio)ethoxy)phenylthio)pyridine, and then 10 mL of methyl iodide was added thereto. The resultant solution was then heated under reflux. After the completion of the reaction, the solvent and an excess amount of methyl iodide were removed by distillation under reduced pressure. The residue was dissolved in chloroform, and purified by silica gel column chromatography (yielded amount 7.5 g, and yield 65.9%).

Synthesis [1-7]: Synthesis of 4-(2,2-bis(4-(6-(4-(cyanophenyl)phenoxy)hexyloxy)phenylthio)ethoxy)benzenethiol Into tetrahydrofuran was dissolved 7 g of 2-(4-(2,2-bis(4-(6-(4-(cyanophenyl)phenoxy)hexyloxy)phenylthio)ethoxy)phenylthio)-1-methylpyridium iodide, and then 2 mL of hydrazine monohydrate was added thereto under the nitrogen atmosphere. The reaction was monitored with TLC. After it was confirmed that the original point components disappeared, 4 mL of acetic acid was added to the reaction liquid.

The resultant reaction mixture was concentrated, and then water and chloroform were added thereto, followed by extraction. The organic phase was purified by column chromatography, to give an oily substance. This oily substance was allowed to stand, to solidify into a wax-like substance (yield amount 4.0 g, and yield 70.2%).

Synthesis [1-8]: Synthesis of tetrakis(3-formylphenoxymethyl)methane 5 g of pentaerythrityl tetrabromide, 9.5 g of 3-hydroxybenzaldehyde, 11 g of potassium carbonate, and a catalytic amount of sodium iodide were mixed. Thereto was added dimethylformamide, to conduct reaction at 130° C. for 6 hours. After cooled, water was added thereto, and the thus-precipitated crystal was collected by filtration. Dimethylformamide was added to this crystal, and the resultant solution was filtrated. Then, methanol was added to the filtrate, and the precipitated crystal was collected by filtration (yield amount 6.1 g, and yield 85.6%).

Synthesis [1-9]: Synthesis of Exemplified Compound (4)

Into dichlorormethane were dissolved 72 mg of tetrakis(3-formylphenoxymethyl)methane and 1 g of 4-(2,2-bis(4-(6-(4-(cyanophenyl)phenoxy)hexyloxy)phenylthio)ethoxy) benzenethiol, and then thereto was added p-toluenesulfonic acid as a catalyst. The resultant solution was heated under reflux. After it was confirmed by TLC that spots were converged, the reaction was finished. The resultant was purified by silica gel column chromatography, to give a colorless solid not showing a definite melting point (yield amount 120 mg, and yield 11.3%).

NMR data (CDCl$_3$): δH 6.6-7.75 (240H, m), 5.12 (4H, s), 4.38 (8H, t), 4.10 (16H, d), 3.80-4.10 (72H, m), 1.66-1.90 (64H, b), 1.40-1.65 (64H, b)

Example 2

Synthesis of Exemplified Compound (6)

Synthesis [2-1]: Synthesis of 2-(4-formylphenyl)-1,3-dioxolane

To 134 g of terephthalaldehyde and 62 g of ethylene glycol, was added 400 mL of toluene, and then was added thereto 2 g of p-toluenesulfonic acid, to conduct dehydration reaction under azeotropic conditions. After the time when the reaction of water stopped in the reaction, the reaction liquid was heated under reflux for another 2 hours, followed by cooling. The resultant reaction liquid was poured into an aqueous sodium bicarbonate solution. The organic phase was concentrated, and then purified by silica gel column chromatography (yield amount 122 g, and yield 68.5%).

Synthesis [2-2]: Synthesis of 2-(4-hydroxymethylphenyl)-1,3-dioxolane

To 100 g of 2-4-formylphenyl)1,3-dioxolane were added 300 mL of water and 500 g of ice, followed by stirring. Thereto was added sodium borohydride little by little. After it was confirmed by TLC that the raw materials disappeared, the resultant solution was extracted with ethyl acetate 2 times, and dried with anhydrous magnesium sulfate. The solvent was then distilled off. The residue was purified by silica gel column chromatography, to give the target compound (yield amount 95 g, and yield 93.8%).

Synthesis [2-3]: Synthesis of 4-chloromethylbenzaldehyde

To 80 g of 2-(4-hydroxymethylphenyl)-1,3-dioxolane was added 300 mL of concentrated hydrochloric acid, and then the solution was heated under reflux for 24 hours. After the solution was cooled, the precipitated crystal was collected by filtration, washed with water, and then dried at room temperature. The resultant was recrystallized from methanol/water (yield amount 47 g, and yield 68.4%).

Synthesis [2-4]: Synthesis of 4-((5-nitropyridine-2-yl)thiomethyl)benzaldehyde To 40 mg of 2-mercapto-5-nitropyridine was added 200 mL of acetone, and the solution was stirred while cooled with water. To this reaction solution were added 43.6 of 4-chloromethylbenzaldehyde and 45 g of potassium carbonate, to conduct reaction. After the completion of the reaction, 1 L of water was added to the solution. The precipitated crystal was collected by filtration, washed with water, washed with methanol, and dried (yield amount 65.5 g, and yield 93.3%).

Synthesis [2-5]: Synthesis of 2-((4-bis(4-bromophenylthio)methyl)phenylmethylthio)-5-nitropyridine Into dichloromethane was dissolved 61.1 g of 4-((5-nitropyridine-2-yl)thiomethyl)benzaldehyde, and then thereto were added 100 g of 4-bromobenzenethiol and 6 g of p-toluenesulfonic acid, to conduct reaction at room temperature for 4 days. Then, water was added to the reaction mixture, followed by extraction. The organic phase was concentrated, and then ethyl acetate and hexane were added thereto, to give a crystal (yield amount 129.0 g, and yield 77.0%).

Synthesis [2-6]: Synthesis of 4-(bis(4-bromophenylthio))methylphenylmethanethiol Under the atmosphere of nitrogen, 70 g of 2-((4-bis(4-bromophenylthio)methyl)phenylmethylthio)-5-nitropyridine was dissolved into dimethylformamide, and then 25 mL of hydrazine hydrate was added thereto, to conduct reaction at 70° C. After the completion of the reaction, the solution was cooled. Thereto was added 30 mL of acetic acid, and then added water and ethyl acetate, followed by extraction. The organic phase was washed with water, and dried with anhydrous magnesium sulfate. The organic phase was concentrated, and the residue was purified by silica gel column chromatography, to yield the target compound (yield amount 39.2 g, and yield 69.3%).

Synthesis [2-7]: Synthesis of Exemplified Compound (6)

Into dichloromethane was dissolved 12 g of 4-(bis(4-bromophenylthio))methylphenylmethanethiol, and then thereto was added 2 g of the benzaldehyde synthesized in Synthesis [2-4]. The solution was stirred at room temperature. A catalytic amount of methanesulfonic acid was added to this solution. The advance of the reaction was confirmed by liquid chromatography, and then the reaction was stopped. Water was added thereto, followed by extraction. Then, the resultant was purified by silica gel column chromatography, to yield the target compound as a colorless solid not showing a definite melting point (yield amount 2.1 g, and yield 22.5%).

NMR data (CDCl$_3$): δH 9.27 (1H, d), 8.23 (1H, dd), 7.03-7.41 (29H, m), 5.34 (2H, s), 4.50 (2H, s), 4.32 (1H, s), 3.72 (2H, d), 3.48 (2H, d)

Example 3

Synthesis of Exemplified Compound (6)

In the same manner as in the Syntheses [2-1] to [2-6] in Example 2, 4-(bis(4-bromophenylthio))methylphenylmethanethiol was prepared. Into tetrahydrofuran was dissolved 12 g (23.4 mmol) of 4-(bis(4-bromophenylthio))methylphenylmethanethiol. Thereto was added 3.85 g (14.1 mmol: 1.2 equivalents) of the aldehyde synthesized in Synthesis [2-4], followed by stirring at −5° C. Thereto was added a catalytic amount of methanesulfonic acid. The advance of the reaction was confirmed by liquid chromatography, and the reaction was stopped. Water was added to the solution to conduct extraction, and then the resultant was purified by silica gel column chromatography, to give the target compound as a colorless solid not showing a definite melting point (yield amount 9.1 g, and yield 60.7%).

The NMR data (CDCl$_3$) of the thus-obtained target compound was the same as in the Synthesis [2-7] in Example 2.

According to this example, the target compound and the starting aldehyde were present after the completion of the reaction even if the excessive amount of the aldehyde was reacted with the thiol. However, the starting thiol was wholly consumed by the reaction, and was not observed after the reaction.

Example 4

Synthesis of Exemplified Compound (6)

In the same manner as in the Syntheses [2-1] to [2-6] in Example 2, 4-(bis(4-bromophenylthio))methylphenylmethanethiol was prepared. Into 3 mL of a solvent, as shown in Table 1, was admixed 120 mg of 4-(bis(4-bromophenylthio))methylphenylmethanethiol, and then thereto was added 38.5 mg (1.2 equivalents) of the aldehyde synthesized in Synthesis [2-4], followed by stirring at −10° C. Thereto was added a catalyst (in a catalytic amount), as shown in Table 1. The advance of the reaction was monitored with high-speed liquid chromatography, to measure the yield (conversion ratio) of the target compound when the raw material thiol disappeared. The results are shown in Table 1.

The NMR data (CDCl$_3$) of the thus-obtained target compound was the same as in the Synthesis [2-7] in Example 2.

TABLE 1

| Experiment No. | Solvent | Catalyst | Yield of the target compound (%) |
|---|---|---|---|
| 1 (Comparative example) | Methylene chloride | Methanesulfonic acid | 35.0 |
| 2 (Comparative example) | Methylene chloride | In(OTf)$_3$ | 45.1 |
| 3 (This invention) | THF | Methanesulfonic acid | 80.8 |
| 4 (This invention) | THF | In(OTf)$_3$ | 80.0 |
| 5 (This invention) | Ethyl acetate | Methanesulfonic acid | 63.2 |

(Note)
In(OTf)$_3$: Indium (III) trifluoromethanesulfonate
THF: Tetrahydrofuran

As is apparent from the results shown in Table 1, in the test Nos. 3 to 5 in which an ether or ester was used as a reaction solvent, the Exemplified compound (6) could be produced in a remarkably higher yield.

Example 5

Synthesis of Exemplified Compound (7)

Into 50 mL of dimethylformamide was dissolved 10 g of the Exemplified compound (6) synthesized in Synthesis [2-7], and then thereto was added 8 g of hydrazine hydrate. Under the atmosphere of nitrogen, the solution was heated to 100° C. The completion of the reaction was confirmed by TLC, and the reaction was stopped. Thereto were added water and ethyl acetate, to conduct extraction. Then, the organic phase was concentrated and purified by silica gel column chromatography, to give the target compound as a colorless solid not showing a definite melting point (yield amount 5.5 g, and yield 60.8%).

NMR data (CDCl$_3$): δH 7.0-7.4 (28H, m), 5.38 (2H, s), 4.35 (1H, s), 3.68-3.8 (4H, m), 3.50 (2H, d), 1.76 (1H, t)

Example 6

Synthesis of Exemplified Compound (8)

Into tetrahydrofuran was dissolved 4.5 g of the Exemplified compound (7) prepared in Example 5, and then thereto was added 0.56 g of the benzaldehyde synthesized in Synthesis [2-4]. The solution was stirred at 5° C. A catalytic amount of methanesulfonic acid was added to this solution. The advance of the reaction was confirmed by liquid chromatography, and then the reaction was stopped. Water was added thereto, followed by extraction. Then, the organic phase was purified by silica gel column chromatography, to yield the target compound as a colorless solid not showing a definite melting point (yield amount 0.8 g, and yield 16.0%).

NMR data (CDCl$_3$): δH 9.24 (1H, d), 8.20 (1H, dd), 7.0-7.4 (61H, m), 5.35 (4H, s), 4.58 (1H, s), 4.47 (2H, s), 4.35 (2H, s), 3.68-3.80 (6H, m), 3.58 (2H, d), 3.49 (4H, d)

Example 7

Synthesis of Exemplified Compound (8)

Into tetrahydrofuran was dissolved 4.5 g (3.88 mmol) of the Exemplified compound (7) obtained in Example 5, and then thereto was added 0.64 g (2.04 mmol: 1.2 equivalents) of the aldehyde synthesized in Synthesis [2-4]. The solution was stirred at −10° C. Thereto was added a catalytic amount of methanesulfonic acid. The advance of the reaction was confirmed by liquid chromatography, to stop the reaction. Thereto was added water, to conduct extraction. Then, the organic phase was purified by silica gel column chromatography, to give the target compound as a colorless solid not showing a definite melting point (yield amount 3.3 g, and yield 66.1%).

The NMR data (CDCl$_3$) of the thus-obtained target compound was the same as in Example 6.

According to this example, the target compound and the starting aldehyde were present in the reaction mixture after the completion of the reaction even if the excessive amount of the aldehyde was reacted with the thiol. However, the starting thiol was wholly consumed by the reaction, and was not observed after the reaction.

Further, the synthesis was conducted in the same manner as in the above, except for using methylene chloride or chloroform instead of tetrahydrofuran. As a result, the reaction was complicated and various byproducts were intermingled, and thus it was difficult to isolate the target compound. From this fact, the advantageous effect of the present invention is apparent. Further, it is understood that the method of the present invention is significantly useful for the synthesis of a dendrimer or dendron.

Example 8

Synthesis of Exemplified Compound (9)

Into 5 ml of dimethylformamide was dissolved 1 g of the Exemplified compound (8) obtained in Example 6, and then thereto was added 1 g of hydrazine hydrate. Under the atmosphere of nitrogen, the solution was heated to 100° C. The completion of the reaction was confirmed by TLC, and the reaction was stopped. Thereto were added water and chloroform, to conduct extraction. Then, the organic phase was concentrated and purified by silica gel column chromatography, to give the target compound as a colorless solid not showing a definite melting point (yield amount 0.45 g, and yield 47.2%).

NMR data (CDCl$_3$): δH 7.05-7.38 (60H, m), 5.33 (4H, s), 4.57 (1H, s), 4.35 (2H, s), 3.65-3.8 (8H, m), 3.60 (2H, d), 3.48 (4H, d), 1.77 (1H, t)

Example 9

Synthesis of Exemplified Compound (10)

Into tetrahydrofuran was dissolved 1.6 g of the Exemplified compound (9) synthesized in Example 8, and then thereto was added 0.1 g of the benzaldehyde synthesized in Synthesis [2-4]. The solution was stirred at 5° C. A catalytic amount of indium trifluoromethanesulfonate was added to this solution. The advance of the reaction was confirmed by liquid chromatography, and then the reaction was stopped. Water was added thereto, followed by extraction. Then, the organic phase was purified by silica gel column chromatography, to yield the target compound as a colorless solid not showing a definite melting point (yield amount 0.80 g, and yield 47.5%).

NMR data (CDCl$_3$): δH 9.22 (1H, d), 8.15 (1H, dd), 7.0-7.4 (125H, m), 5.36 (8H, s), 4.60 (2H, s), 4.56 (1H, s), 4.45 (2H, s), 4.35 (4H, s), 3.65-3.80 (14H, m), 3.58 (4H, d), 3.55 (2H, d), 3.46 (8H, d)

Example 10

Synthesis of Exemplified Compound (10)

Into 30 ml of tetrahydrofuran was dissolved 1.0 g (0.408 mmol) of the Exemplified compound (9) synthesized in Example 8, and then thereto was added 0.084 g (0.306 mmol: 1.5 equivalents) of the aldehyde synthesized in Synthesis [2-4], to form a solution. The resultant solution was stirred at −5° C. Thereto, was added 2 mL of methanesulfonate, to start a reaction. The advance of the reaction was confirmed by TLC, and then the reaction was stopped. Water was added thereto, followed by extraction. Then, the organic phase was purified by silica get column chromatography, to yield the target compound as a colorless solid not showing a definite melting point (yield amount 0.46 g, and yield 43.7%).

The NMR data (CDCl$_3$) of the thus-obtained target compound was the same as in Example 9.

According to this example, the target compound and the starting aldehyde were present in the reaction mixture after the completion of the reaction even if the excessive amount of the aldehyde was reacted with the thiol. However, the starting thiol was wholly consumed by the reaction, and was not observed after the reaction. Further, it is understood from this example that the method of the present invention is quite useful for the synthesis of a dendrimer or dendron.

Example 11

Synthesis of Exemplified Compound (11)

Into 3 mL of dimethylformamide was dissolved 0.4 g of the Exemplified compound (10) synthesized in Example 9, and then thereto was added 0.8 g of methyl hydrazine. Under the atmosphere of nitrogen, the solution was heated to 100° C. The completion of the reaction was confirmed by TLC, and the reaction was stopped. Thereto were added water and chloroform, to conduct extraction. Then, the organic phase was concentrated and purified by silica gel column chromatography, to give the target compound as a colorless solid not showing a definite melting point (yield amount 0.27 g, and yield 69.1%).

NMR data (CDCl$_3$): δH 7.0-7.4 (124H, m), 5.35 (8H, s), 4.60 (2H, s), 4.54 (1H, s), 4.35 (4H, s), 3.65-3.80 (16H, m), 3.57 (4H, d), 3.55 (2H, d), 3.46 (8H, d), 1.72 (1H, t)

Reference Examples

An example of function of the compound of the present invention is described in below, but the scope of the invention is not limited thereto.

According to the above-mentioned synthetic method(s), the following Compounds (NBD-1), (NBD-2), (NBD-3), and (NBD-4) were synthesized.

(NBD-1)
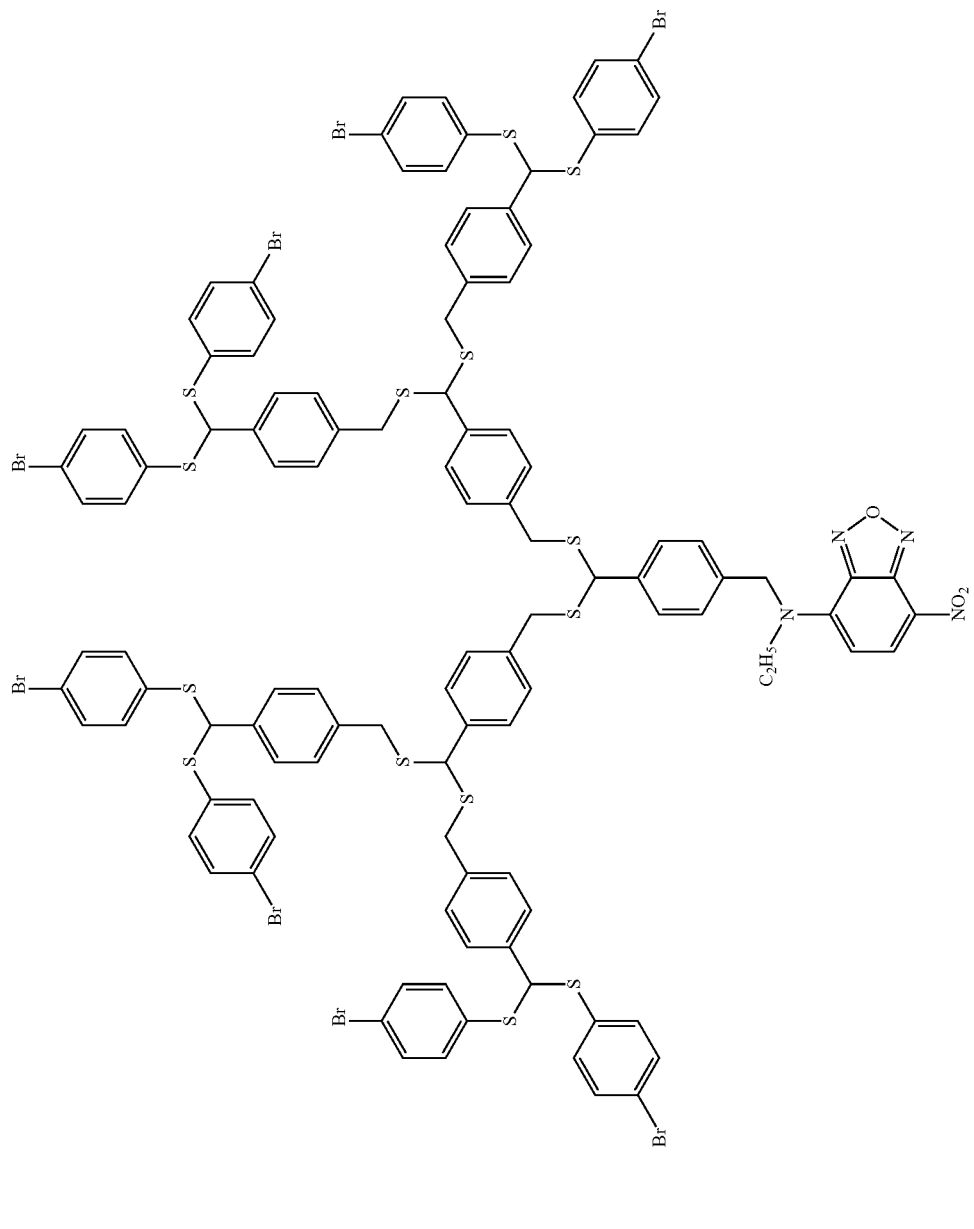
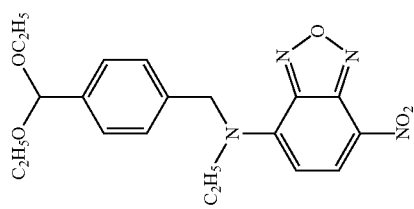

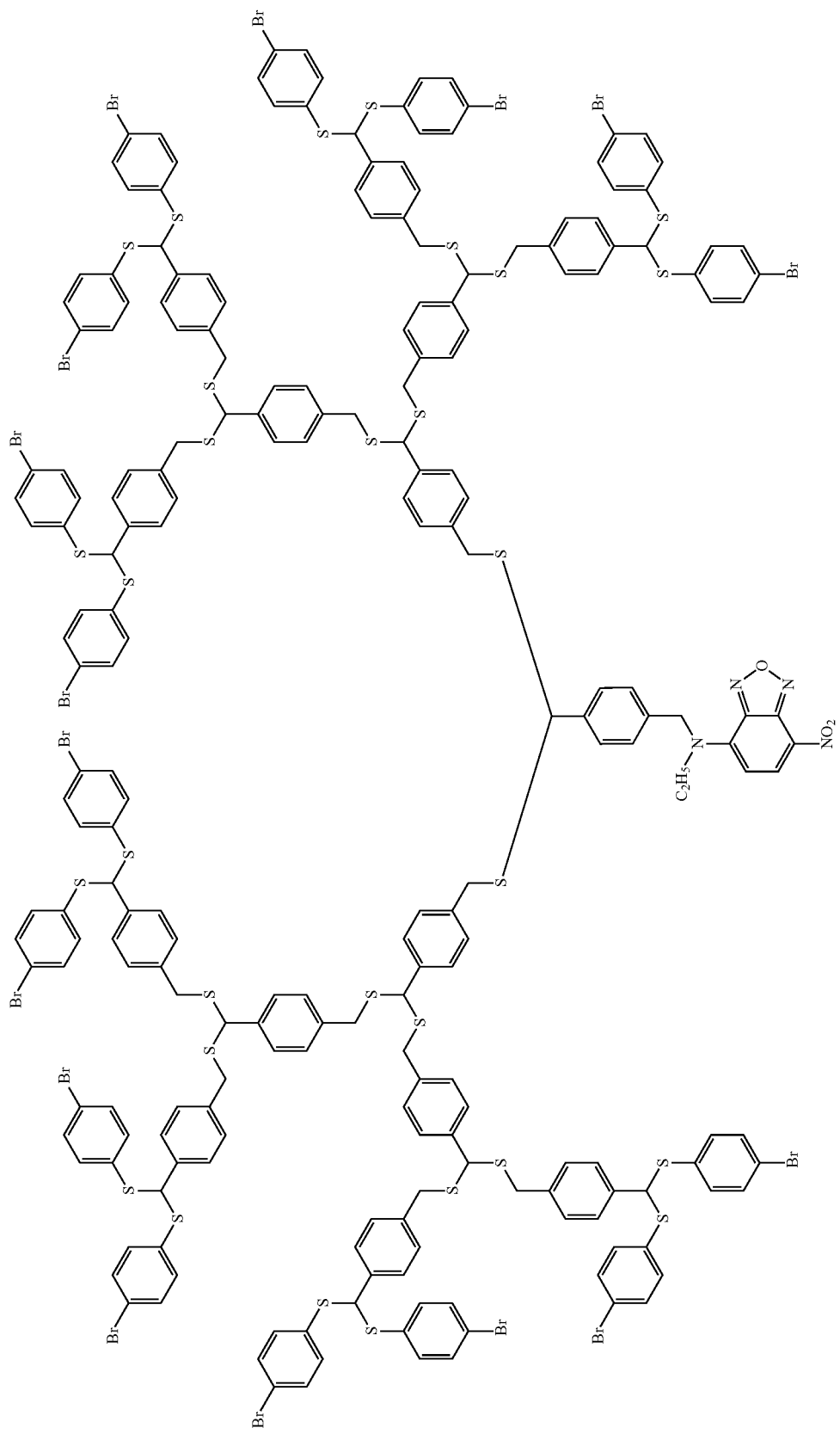
(NBD-3)

(NBD-4)
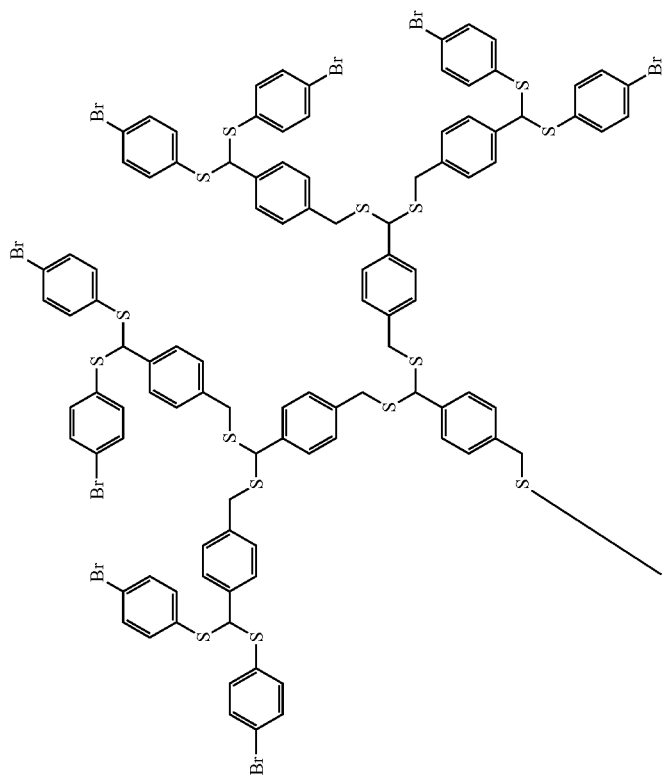
-continued
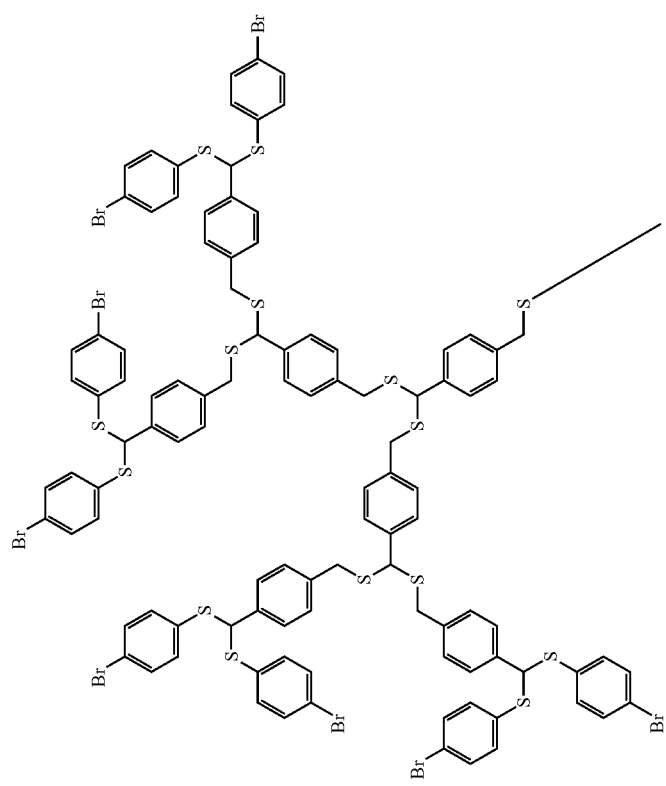

-continued
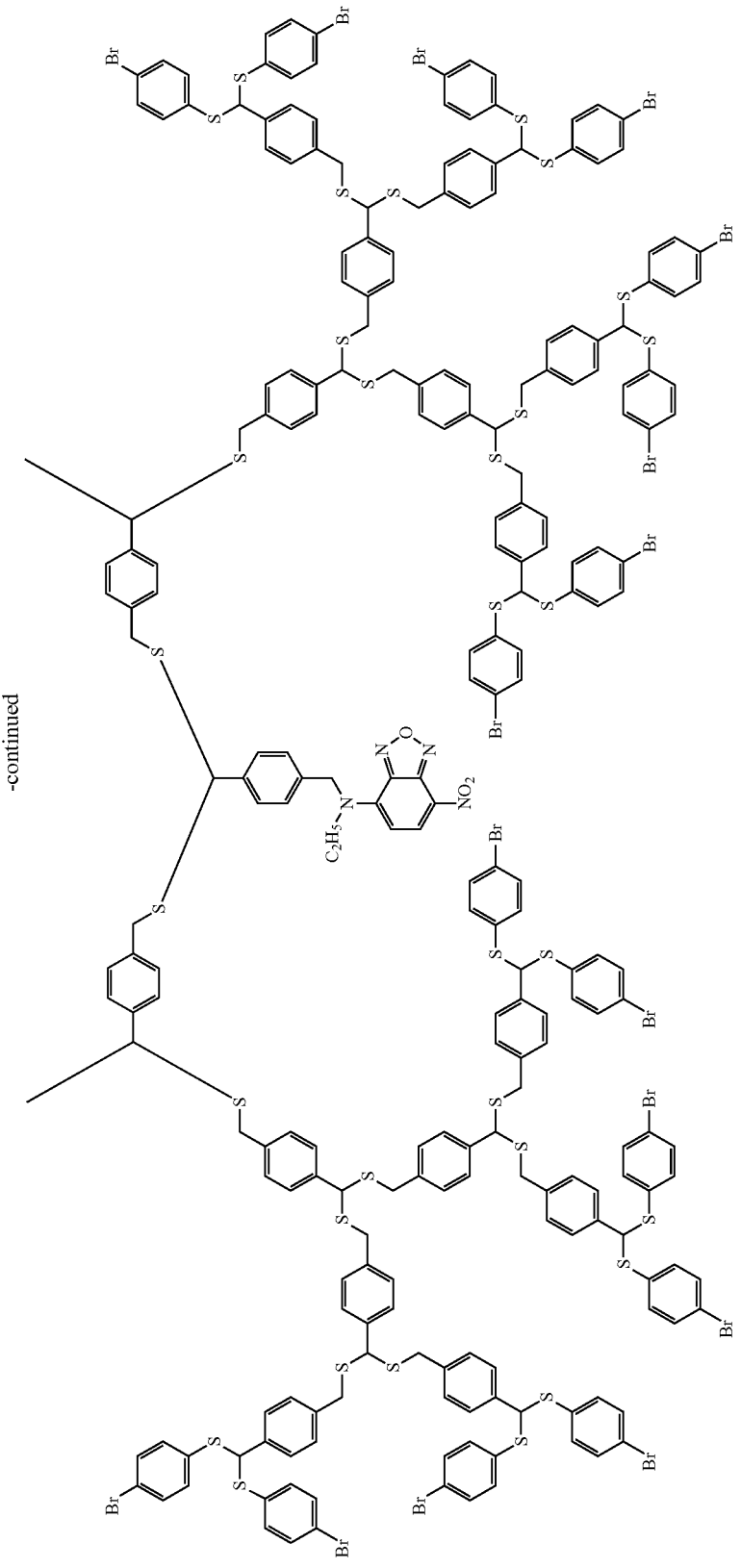

The thus-prepared Compound (NBD-1) was dissolved into tetrahydrofuran, to prepare a $5 \times 10^{-5}$ M tetrahydrofuran solution. Similarly, $5 \times 10^{-5}$ M tetrahydrofuran solutions of (NBD-2), (NBD-3) or (NBD4) were prepared, respectively. Fluorescence from these solutions was observed. Separately, the Compound (NBD-1), (NBD-2), (NBD-3), or (NBD4) was dissolved into tetrahydrofuran, to prepare 5% tetrahydrofuran solutions, respectively. Any one of the solution was applied and developed onto a glass plate, followed by drying, to form a thin film. The thus-prepared film was irradiated with ultraviolet ray of wavelength 365 nm, and then fluorescence therefrom was observed. The results are shown in Table 2.

TABLE 2

|  | Fluorescence from solution | Fluorescence from solid |
|---|---|---|
| (NBD-1) (Comparative example) | Strong green fluorescence | Not observed |
| (NBD-2) | Strong green fluorescence | Weak orange fluorescence |
| (NBD-3) | Strong green fluorescence | Yellowish green fluorescence |
| (NBD-4) | Strong green fluorescence | Strong green fluorescence |

It can be understood from the results shown in the above table that the compound of the present invention has a remarkably large effect for preventing a density quenching of fluorescent dyes. It can also be understood that, by using this effect, the compound of the present invention may be applied to various applications or usages, such as a wavelength conversion device.

INDUSTRIAL APPLICABILITY

The dendrimer or dendron of the present invention may be used in a very wide field, including drug delivery system, gene introduction, energy-trapping optically-active molecules, catalysts, molecular mass/molecular size standard materials, sensor/nano-scale science, and the like. Further, the compound of the present invention may be applied to various applications or usages, such as a wavelength conversion device.

Further, the method of the present invention is preferable to give the target dendrimer or dendron, or a thioacetal that can be preferably used to produce a dendrimer or dendron, quite efficiently, with less burden to purify the target product after the reaction.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2004-095408 filed in Japan on Mar. 29, 2004, Patent Application No. 2004-096073 filed in Japan on Mar. 29, 2004, and Patent Application No. 2004-096080 filed in Japan on Mar. 29, 2004, each of which is herein entirely incorporated by reference.

The invention claimed is:
1. A dendron, having, as a recurring unit of each branch, a structure represented by formula (I):

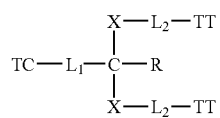

Formula (I)

wherein TC designates a linkage to a former generation in the direction to a focal point of the dendron; TT's each designate a linkage to a next generation in the direction to a terminal of the dendron; X is —S—, —SO—, or —SO$_2$—; L$_1$ and L$_2$'s each independently represent a divalent linking group selected from the group consisting of —CH$_2$—, —CH$_2$CH$_2$—, —CH$_2$CH$_2$CH$_2$—, 1,2-phenylene, 1,3-phenylene, 1,4-phenylene, α,2-tolylene, α,3-tolylene, α,4-tolylene, o-xylylene, m-xylylene, p-xylylene, and a divalent group wherein any one of these divalent groups is combined with —O—, —S—, —P=O(R$_1$)—, —N(R$_1$)—, —CO—, —SO—, —SO$_2$— or —Si(R$_1$)(R$_2$)— wherein R$_1$ and R$_2$ each independently represents a hydrogen atom or a substituent; R represents a hydrogen atom; and in the recurring units, X's may be the same or different, L$_1$'s may be the same or different, and L$_2$'s may be the same or different, wherein the dendron has a focal point selected from the group consisting of a chain or cyclic saturated hydrocarbon, a chain or cyclic unsaturated hydrocarbon, an aromatic hydrocarbon, a non-aromatic heteroring, an aromatic heteroring, and the focal point may have a substituent selected from the group consisting of a mercapto group, a hydroxyl group, a cyano group, a nitro group, a halogen atom, a hydrazino group, an azo group, an isocyanato group, an isothiocyanato group, a thiocyanato group, a carboxyl group, a sulfo group, an acyl group, a formyl group, an alkoxycarbonyl group, a carbamoyl group, a sulfamoyl group, an alkoxysulfonyl group, a sulfonyl group, an amino group, an acylamino group, a sulfonylamino group, a sulfenyl group, a sulfinyl group, an alkoxy group, an alkyl group, an alkenyl group, an alkynyl group, an aryl group, a silyl group, a silyloxy group, and a heterocyclic group and the dendron has a generation number of from 2 to 20.

2. The dendron according to claim 1, wherein the divalent group represented by X in formula (I) is —S—.

3. The dendron according to claim 1, whose terminal surface has a functional group selected from a mercapto group, a hydroxyl group, a halogen atom, a hydrazino group, a cyano group, an isocyanato group, an isothiocyanato group, a thiocyanato group, a carboxyl group, a sulfo group, an acyl group, a formyl group, an amino group, an alkenyl group, or an alkynyl group, each of which may be in a protected form.

4. A dendrimer, having, as a recurring unit of each branch, a structure represented by formula (I):

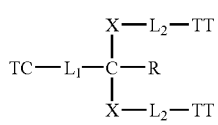

Formula (I)

wherein TC designates a linkage to a former generation in the direction to a core of the dendrimer; TT's each designate a linkage to a next generation in the direction to a terminal of the dendrimer; X is —S—, —SO—, or —SO$_2$—; L$_1$ and L$_2$'s each independently represent a divalent linking group selected from the group consisting of —CH$_2$—, —CH$_2$CH$_2$—, —CH$_2$CH$_2$CH$_2$—, 1,2-phenylene, 1,3-phenylene, 1,4-phenylene, α,2-tolylene, α,3-tolylene, α,4-tolylene, o-xylylene, m-xylylene, p-xylylene, and a divalent group wherein any one of these divalent groups is combined with —O—, —S—, —P=O(R$_1$)—, —N(R$_1$)—, —CO—, —SO—, —SO$_2$— or —Si(R$_1$)(R$_2$)— wherein R$_1$ and R$_2$ each independently represents a hydrogen atom or a substituent; R represents a hydrogen atom; and in the recurring units, X's may be the same or different, L$_1$'s may be the same or different, and L$_2$'s may be the same or different, wherein the dendrimer has a core selected from the group consisting of a chain or cyclic saturated hydrocarbon, a chain or cyclic unsaturated hydrocarbon, an aromatic hydrocarbon, a non-aromatic heteroring, an aromatic heteroring, and the focal point may have a substituent selected from the group consisting of a mercapto group, a hydroxyl group, a cyano group, a nitro group, a halogen atom, a hydrazino group, an azo group, an isocyanato group, an isothiocyanato group, a thiocyanato group, a carboxyl group, a sulfo group, an acyl group, a formyl group, an alkoxycarbonyl group, a carbamoyl group, a sulfamoyl group, an alkoxysulfonyl group, a sulfonyl group, an amino group, an acylamino group, a sulfonylamino group, a sulfenyl group, a sulfinyl group, an alkoxy group, an alkyl group, an alkenyl group, an alkynyl group, an aryl group, a silyl group, a silyloxy group, and a heterocyclic group and the dendrimer has a generation number of from 2 to 20.

5. The dendrimer according to claim 4, wherein the divalent group represented by X in formula (I) is —S—.

6. The dendrimer according to claim 4, whose terminal surface has a functional group selected from a mercapto group, a hydroxyl group, a halogen atom, a hydrazino group, a cyano group, an isocyanato group, an isothiocyanato group, a thiocyanato group, a carboxyl group, a sulfo group, an acyl group, a formyl group, an amino group, an alkenyl group, or an alkynyl group, each of which may be in a protected form.

7. A method of producing the dendron of claim 1, which is a convergent method in which n branches are formed from a gth generation, so as to form a (g+1)th generation, in which n is an integer of 2 to 5 and g is an integer of 1 or more, which comprises the step of:
carrying out a reaction, to form the branches, the reaction satisfying a relationship of:

$$k_1 < k_m$$

wherein m is an integer of 2 or more but less than n; $k_1$ represents a rate of growth reaction from the gth generation to the (g+1)th generation, in which only one branch has grown from the gth generation; and $k_m$ represents a rate of reaction from a structure in which (m−1) branches out of the n branches have grown to a structure in which m branches have grown.

8. The method according to claim 7, wherein the step of forming branches is carried out repeatedly.

9. The method according to claim 7, wherein the reaction rate $k_m$ further satisfy a relationship of:

$$k_{m-1} < k_m < k_n$$

wherein $k_{m-1}$ represents a rate of reaction from a structure in which (m−2) branches out of the n branches have grown to a structure in which (m−1) branches have grown, and $k_n$ represents a rate of reaction from a structure in which (n−1) branches out of the n branches have grown to a structure in which n branches have grown.

10. The method according to claim 9, wherein the step of forming branches is carried out repeatedly.

11. The method according to claim 7, which satisfies the following condition:

$$k_1 < k_2 < \ldots < k_n$$

in a reaction for forming a branch structure of said dendron or dendrimer, as represented by formula (II):

Formula (II)

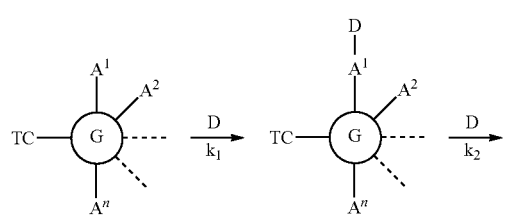

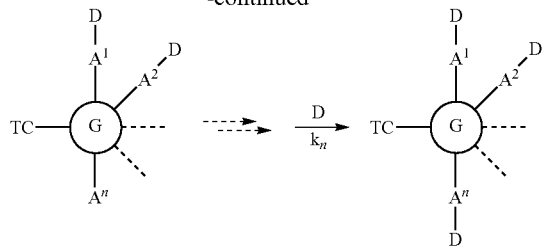

wherein, in formula (II), TC designates a linkage to a former generation in the direction to a focal point of the dendron, or TC designates a linkage to a former generation in the direction of a core of the dendrimer; G represents a group containing at least one carbon atom; $A^1$, $A^2, \ldots$, and $A^n$ mean that G can form n bonds; n represents an integer of 2 to 5; $k_1, k_2, \ldots$, and $k_n$ represent rate constants of respective reactions; and D represents a monovalent group for forming a moiety at a surface terminal side of the dendron or dendrimer.

12. A method of producing the dendron of claim 2, comprising:
subjecting a thiol to a reaction with a carbonyl compound or an equivalent thereof, to form a thioacetal, thereby forming a branch structure of said dendron or said dendrimer.

13. A method of producing the dendrimer of claim 5, comprising the step of:
producing a thioacetal structure by a method of producing a thioacetal compound comprising subjecting a thiol compound having in the molecule thereof a thioacetal structure, to a reaction with a carbonyl compound or an equivalent thereof, in the presence of a catalyst, in a reaction solvent selected from ethers, esters, amides, sulfoxides, alcohols, nitriles, and sulfones, thereby to form a thioacetal structure.

14. The method according to claim 13, wherein the thiol compound having in the molecule thereof a thioacetal structure has at least one thiol group and at least one thioacetal structure represented by $R^1$—$C(SR^2)_2$—$R^3$, in which $R^1$ and $R^3$ each independently represent a hydrogen atom, an alkyl group, an aryl group, an alkenyl group, an alkynyl group, or a heterocyclic group, provided that $R^1$ and $R^3$ are not hydrogen atoms simultaneously; and $R^2$ is an alkyl group, an aryl group, an alkenyl group, an alkynyl group, or a heterocyclic group.

15. The method according to claim 13, wherein the carbonyl compound is represented by $R^4$—CO—$R^5$, in which $R^4$ and $R^5$ each independently represent a hydrogen atom, an alkyl group, an aryl group, an alkenyl group, an alkynyl group, or a heterocyclic group, provided that $R^4$ and $R^5$ are not hydrogen atoms simultaneously; and wherein the equivalent of the carbonyl compound is represented by $R^4$—$CX_2$—$R^5$, in which $R^4$ and $R^5$ have the same meanings as defined in the above; and $X_2$ is an alkoxy group, an aryloxy group, a heteroaryloxy group, a halogen atom, an imino group, a hydroxyimino group, an alkoxyimino group, a sulfonylimino group, an acylimino group, or an aminoimino group.

16. The method according to claim 13, wherein the solvent is a cyclic ether.

17. A method of producing the dendron of claim 2, comprising the step of:
producing a thioacetal structure by a method of producing a thioacetal compound comprising subjecting a thiol compound having in the molecule thereof a thioacetal structure, to a reaction with a carbonyl compound or an equivalent thereof, in the presence of a catalyst, in a reaction solvent selected from ethers, esters, amides, sulfoxides, alcohols, nitriles, and sulfones, thereby to form a thioacetal structure.

18. The method according to claim 17, wherein the solvent is a cyclic ether.

19. A method of producing the dendrimer of claim 5, comprising:
subjecting a thiol to a reaction with a carbonyl compound or an equivalent thereof, to form a thioacetal, thereby forming a branch structure of said dendron or said dendrimer.

20. The method according to claim 17, wherein the thiol compound having in the molecule thereof a thioacetal structure has at least one thiol group and at least one thioacetal structure represented by $R^1$—$C(SR^2)_2$—$R^3$, in which $R^1$ and $R^3$ each independently represent a hydrogen atom, an alkyl group, an aryl group, an alkenyl group, an alkynyl group, or a heterocyclic group, provided that $R^1$ and $R^3$ are not hydrogen atoms simultaneously; and $R^2$ is an alkyl group, an aryl group, an alkenyl group, an alkynyl group, or a heterocyclic group.

21. The method according to claim 17, wherein the carbonyl compound is represented by $R^4$—CO—$R^5$, in which $R^4$ and $R^5$ each independently represent a hydrogen atom, an alkyl group, an aryl group, an alkenyl group, an alkynyl group, or a heterocyclic group, provided that $R^4$ and $R^5$ are not hydrogen atoms simultaneously; and wherein the equivalent of the carbonyl compound is represented by $R^4$—$CX_2$—$R^5$, in which $R^4$ and $R^5$ have the same meanings as defined in the above; and $X_2$ is an alkoxy group, an aryloxy group, a heteroaryloxy group, a halogen atom, an imino group, a hydroxyimino group, an alkoxyimino group, a sulfonylimino group, an acylimino group, or an aminoimino group.

* * * * *